United States Patent
Renauld-Mongenie et al.

(10) Patent No.: US 10,232,029 B2
(45) Date of Patent: Mar. 19, 2019

(54) **COMPOSITIONS COMPRISING *N. MENINGITIDIS* PROTEINS**

(71) Applicant: SANOFI PASTEUR, Lyons (FR)

(72) Inventors: Genevieve Renauld-Mongenie, Chaponost (FR); Bachra Rokbi, Lyons (FR); Noelle Mistretta, Sain-Bel (FR)

(73) Assignee: Sanofi Pasteur, Lyons (FR)

( * ) Notice: Subject to any disclaimer, the term of this patent is extended or adjusted under 35 U.S.C. 154(b) by 0 days.

(21) Appl. No.: 15/534,438

(22) PCT Filed: Dec. 8, 2015

(86) PCT No.: PCT/EP2015/079021
§ 371 (c)(1),
(2) Date: Jun. 8, 2017

(87) PCT Pub. No.: WO2016/091902
PCT Pub. Date: Jun. 16, 2016

(65) Prior Publication Data
US 2018/0125959 A1    May 10, 2018

(30) Foreign Application Priority Data
Dec. 9, 2014    (EP) .................... 14306978

(51) Int. Cl.
*A61K 39/095* (2006.01)
*C07K 14/22* (2006.01)
*A61K 39/00* (2006.01)

(52) U.S. Cl.
CPC ............ *A61K 39/095* (2013.01); *C07K 14/22* (2013.01); *A61K 2039/55555* (2013.01); *A61K 2039/55566* (2013.01); *A61K 2039/575* (2013.01); *A61K 2039/70* (2013.01); *C07K 2319/40* (2013.01); *C07K 2319/50* (2013.01)

(58) Field of Classification Search
CPC .................................................. A61K 39/095
See application file for complete search history.

(56) References Cited

FOREIGN PATENT DOCUMENTS

| CA | 2207302 | 6/1997 |
|---|---|---|
| CA | 2267066 | 4/1999 |
| WO | WO 97/13860 | 4/1997 |
| WO | WO 99/07741 | 2/1999 |
| WO | WO 00/71725 | 11/2000 |
| WO | WO 2004/014418 | 2/2004 |
| WO | WO 2005/032583 | 4/2005 |
| WO | WO 2011/051893 | 5/2011 |
| WO | WO 2016/091890 | 6/2016 |
| WO | WO 2016/091912 | 6/2016 |

OTHER PUBLICATIONS

Van Ulsen et al (Molecular Microbiology vol. 50 (3), pp. 1017-1030) (Year: 2003).*
Harrison et al (BMC Microbiology vol. 8 (66) pp. 1-10) (Year: 2008).*
Sequence Listing from PCT published application No. WO 2011/051893 published May 5, 2011.
Sequence Listing from PCT published application No. WO 99/07741 published Feb. 18, 1999.
International Search Report dated Apr. 28, 2016 of PCT/EP2015/079021 filed Dec. 8, 2015, 9 pages.
European Search Report dated May 6, 2015 of European Application No. 14306978 filed Dec. 9, 2014, 7 pages.

* cited by examiner

*Primary Examiner* — Albert M Navarro
(74) *Attorney, Agent, or Firm* — McDonnell Boehnen Hulbert & Berghoff LLP

(57) ABSTRACT

The invention relates to immunogenic compositions comprising at least two *Neisseria meningitidis* (Nm) protein antigens selected from the group consisting of a trypsin-like serine protease auto-transporter antigen such as IgAl P, App or AusI antigen, a NalP antigen and a TbpB antigen. Preferably, the composition of the invention comprises (i) the trypsin-like serine protease auto-transporter antigen and (ii) the NalP antigen and/or TbpB antigen.

31 Claims, 16 Drawing Sheets

Specification includes a Sequence Listing.

| ST | Strains | TbpB FL M982 | | | | | | | | | | | SE |
|---|---|---|---|---|---|---|---|---|---|---|---|---|---|
| | | x2 | x4 | x8 | x16 | x32 | x64 | x128 | x256 | x512 | x1024 | > | |
| ST32 | MC58 | | | | | | | | | | | | ++ |
| | BZ83 | | | | | | | | | | | | +(+) |
| | 8680 | | | | | | | | | | | | +(+); + |
| | LNP22763 | | | | | | | | | | | | ++ |
| | H44/76 | | | | | | | | | | | | +++ |
| | NGPB24 | | | | | | | | | | | | +++ |
| ST11 | B16B6 | | | | | | | | | | | | - |
| | NGP20 | | | | | | | | | | | | - |
| | M986 | | | | | | | | | | | | - |
| | FAM18 (Men C) | | | | | | | | | | | | - |
| Others | 1000 | | | | | | | | | | | | +++ |
| | S3032 | | | | | | | | | | | | +(+) |
| | BZ232 | | | | | | | | | | | | ++ ; +++ |
| | M982 | | | | | | | | | | | | ++++ |
| | NGH41 | | | | | | | | | | | | +/- |
| | Z2491 (Men A) | | | | | | | | | | | | ++ |
| ST41/44 | RH873 | | | | | | | | | | | | +++ |
| | 95/46 | | | | | | | | | | | | +++ |
| | LNP22979 | | | | | | | | | | | | ++(+) |
| | 92/123 | | | | | | | | | | | | +++ |
| ST8 | BZ163 | | | | | | | | | | | | + |
| | BZ157 | | | | | | | | | | | | - ; +/- |
| | M2 | | | | | | | | | | | | +++ ; ++(+) |
| ST269 | 60 (07-1734) | | | | | | | | | | | | +(+) |
| | 62 (07-1889) | | | | | | | | | | | | +(+) |
| | 28 (05-2606) | | | | | | | | | | | | - |

FIG. 1

| ST | Strains | TbpB FL + NalP TR mut ||||||||||| SE |
| --- | --- | --- | --- | --- | --- | --- | --- | --- | --- | --- | --- | --- | --- |
| | | x2 | x4 | x8 | x16 | x32 | x64 | x128 | x256 | x512 | x1024 | > | |
| ST32 | MC58 | | | | | | | | | | | | ++ |
| | BZ83 | | | | | | | | | | | | ++ |
| | 8680 | | | | | | | | | | | | ++ |
| | LNP22763 | | | | | | | | | | | | ++ |
| | H44/76 | | | | | | | | | | | | +++ |
| | NGPB24 | | | | | | | | | | | | +++ |
| ST11 | B16B6 | | | | | | | | | | | | + |
| | NGP20 | | | | | | | | | | | | ++ |
| | M986 | | | | | | | | | | | | + |
| | FAM18 (Men C) | | | | | | | | | | | | - |
| Others | 1000 | | | | | | | | | | | | +++ |
| | S3032 | | | | | | | | | | | | +(+) |
| | BZ232 | | | | | | | | | | | | +++ |
| | M982 | | | | | | | | | | | | ++++ |
| | NGH41 | | | | | | | | | | | | +(+) |
| | Z2491 (Men A) | | | | | | | | | | | | ++(+) |
| ST41/44 | RH873 | | | | | | | | | | | | +++ |
| | 95/46 | | | | | | | | | | | | +++ |
| | LNP22979 | | | | | | | | | | | | ++(+) |
| | 92/123 | | | | | | | | | | | | +++ |
| ST8 | BZ163 | | | | | | | | | | | | + |
| | BZ157 | | | | | | | | | | | | + |
| | M2 | | | | | | | | | | | | ++(+) ; +++ |
| ST269 | 60 (07-1734) | | | | | | | | | | | | +(+) |
| | 62 (07-1889) | | | | | | | | | | | | +(+) |
| | 28 (05-2606) | | | | | | | | | | | | - |

<u>FIG. 4</u>

| ST | Strains | NalP TR mut + IgA protease TR mut (SP503) x2 x4 x8 x16 x32 x64 x128 x256 x512 x1024 > | SE |
|---|---|---|---|
| ST32 | MC58 | | ND |
| | BZ83 | | ND |
| | 8680 | | ND |
| | LNP22763 | | ND |
| | H44/76 | | ND |
| | NGPB24 | | ND |
| ST11 | B16B6 | | ND |
| | NGP20 | | ND |
| | M986 | | ND |
| | FAM18 (Men C) | | ND |
| Others | 1000 | | ND |
| | S3032 | | ND |
| | BZ232 | | ND |
| | M982 | | ND |
| | NGH41 | | ND |
| | Z2491 (Men A) | | ND |
| ST41/44 | RH873 | | ND |
| | 95/46 | | ND |
| | LNP22979 | | ND |
| | 92/123 | | ND |
| ST8 | BZ163 | | ND |
| | BZ157 | | ND |
| | M2 | | ND |
| ST269 | 60 (07-1734) | | ND |
| | 62 (07-1889) | | ND |
| | 28 (05-2606) | | ND |

FIG. 5

| ST | Strains | TbpB FL + NalP TR mut + IgA protease TR mut (SP503) x2 x4 x8 x16 x32 x64 x128 x256 x512 x1024 > | SE |
|---|---|---|---|
| ST32 | MC58 | | ++++ |
| | BZ83 | | ++++ |
| | 8680 | | ++++ |
| | LNP22763 | | ++++ |
| | H44/76 | | ++(+) |
| | NGPB24 | | ++++ |
| ST11 | B16B6 | | + |
| | NGP20 | | ++ |
| | M986 | | + |
| | FAM18 (Men C) | | ++++ |
| Others | 1000 | | +++ |
| | S3032 | | ++++ |
| | BZ232 | | +++ |
| | M982 | | ++++ |
| | NGH41 | | +(+) |
| | Z2491 (Men A) | | +++(+) |
| ST41/44 | RH873 | | ++++ |
| | 95/46 | | ++++ |
| | LNP22979 | | ++++ |
| | 92/123 | | +++ |
| ST8 | BZ163 | | ++++ |
| | BZ157 | | +++ |
| | M2 | | ++(+) |
| ST269 | 60 (07-1734) | | ++++ |
| | 62 (07-1889) | | ++++ |
| | 28 (05-2606) | | ++++ |

FIG. 7

SEQUENCE LISTING

<160> NUMBER OF SEQ ID NOS: 10

<210> SEQ ID NO 1
<211> LENGTH: 1815
<212> TYPE: PRT
<213> ORGANISM: Neisseria meningitidis

<400> SEQUENCE: 1

```
Met Lys Thr Lys Arg Phe Lys Ile Asn Ala Ile Ser Leu Ser Ile Phe
1               5                   10                  15

Leu Ala Tyr Ala Leu Thr Pro Tyr Ser Glu Ala Ala Leu Val Arg Asp
                20                  25                  30

Asp Val Asp Tyr Gln Ile Phe Arg Asp Phe Ala Glu Asn Lys Gly Lys
            35                  40                  45

Phe Phe Val Gly Ala Thr Asp Leu Ser Val Lys Asn Lys Gln Gly Gln
    50                  55                  60

Asn Ile Gly Asn Ala Leu Ser Asn Val Pro Met Ile Asp Phe Ser Val
65                  70                  75                  80

Ala Asp Val Asn Arg Arg Thr Leu Thr Val Ile Asp Pro Gln Tyr Ala
                85                  90                  95

Val Ser Val Lys His Val Lys Gly Asp Glu Ile Ser Tyr Tyr Gly His
            100                 105                 110

His Asn Gly His Leu Asp Val Ser Asn Asp Glu Asn Glu Tyr Arg Ser
    115                 120                 125

Val Ala Gln Asn Asp Tyr Glu Pro Asn Lys Asn Trp His His Gly Asn
130                 135                 140

Gln Gly Arg Leu Glu Asp Tyr Asn Met Ala Arg Leu Asn Lys Phe Val
145                 150                 155                 160

Thr Glu Val Ala Pro Ile Ala Pro Thr Ser Ala Gly Gly Val Glu
                165                 170                 175

Thr Tyr Lys Asp Lys Asn Arg Phe Ser Glu Phe Val Arg Val Gly Ala
            180                 185                 190

Gly Thr Gln Phe Glu Tyr Asn Ser Arg Tyr Asn Met Thr Glu Leu Ser
    195                 200                 205

Arg Ala Tyr Arg Tyr Ala Ile Ala Gly Thr Pro Tyr Gln Asp Val Asn
210                 215                 220

Val Thr Ser Asn Leu Asn Gln Glu Gly Leu Ile Gly Phe Gly Asp Asn
225                 230                 235                 240

Ser Lys His His Ser Pro Glu Lys Leu Lys Glu Val Leu Ser Gln Asn
                245                 250                 255

Ala Leu Thr Asn Tyr Ala Val Leu Gly Asp Ser Gly Ser Pro Leu Phe
            260                 265                 270

Ala Tyr Asp Lys Gln Glu Lys Arg Trp Val Phe Leu Gly Ala Tyr Asp
    275                 280                 285
```

```
Tyr Trp Ala Gly Tyr Gln Lys Asn Ser Trp Gln Glu Trp Asn Ile Tyr
290                 295                 300
Lys Lys Glu Phe Ala Asp Glu Ile Lys Gln Arg Asp Asn Ala Gly Thr
305                 310                 315                 320
Ile Lys Gly Asn Gly Glu His His Trp Lys Thr Thr Gly Thr Asn Ser
                325                 330                 335
His Ile Gly Ser Thr Ala Val Arg Leu Ala Asn Asn Glu Arg Asp Ala
            340                 345                 350
Asn Asn Gly Gln Asn Val Thr Phe Glu Asn Asn Gly Thr Leu Val Leu
        355                 360                 365
Asp Gln Asn Ile Asn Gln Gly Ala Gly Gly Leu Phe Phe Lys Gly Asp
    370                 375                 380
Tyr Thr Val Lys Gly Ile Asn Asn Asp Ile Thr Trp Leu Gly Ala Gly
385                 390                 395                 400
Ile Asp Val Ala Asp Gly Lys Lys Val Val Trp Gln Val Lys Asn Pro
                405                 410                 415
Asn Gly Asp Arg Leu Ala Lys Ile Gly Lys Gly Thr Leu Glu Ile Asn
            420                 425                 430
Gly Thr Gly Val Asn Gln Gly Gln Leu Lys Val Gly Asp Gly Thr Val
        435                 440                 445
Ile Leu Asn Gln Gln Ala Asp Ala Asp Lys Lys Val Gln Ala Phe Ser
    450                 455                 460
Gln Val Gly Ile Val Ser Gly Arg Gly Thr Leu Val Leu Asn Ser Ser
465                 470                 475                 480
Asn Gln Ile Asn Pro Asp Asn Leu Tyr Phe Gly Phe Arg Gly Gly Arg
                485                 490                 495
Leu Asp Ala Asn Gly Asn Asp Leu Thr Phe Glu His Ile Arg Asn Val
            500                 505                 510
Asp Glu Gly Ala Arg Ile Val Asn His Asn Thr Gly His Ala Ser Thr
        515                 520                 525
Ile Thr Leu Thr Gly Lys Ser Leu Ile Thr Asp Pro Lys Thr Ile Ser
    530                 535                 540
Ile His Tyr Ile Gln Asn Asn Asp Asp Asp Ala Gly Tyr Tyr Tyr
545                 550                 555                 560
Tyr Arg Pro Arg Lys Pro Ile Pro Gln Gly Lys Asp Leu Tyr Phe Lys
                565                 570                 575
Asn Tyr Arg Tyr Tyr Ala Leu Lys Ser Gly Gly Ser Val Asn Ala Pro
            580                 585                 590
Met Pro Glu Asn Gly Gln Thr Glu Asn Asn Asp Trp Ile Leu Met Gly
        595                 600                 605
Ser Thr Gln Glu Glu Ala Lys Lys Asn Ala Met Asn His Lys Asn Asn
    610                 615                 620
Gln Arg Ile Ser Gly Phe Ser Gly Phe Phe Gly Glu Glu Asn Gly Lys
625                 630                 635                 640
Gly His Asn Gly Ala Leu Asn Leu Asn Phe Asn Gly Lys Ser Ala Gln
                645                 650                 655
Asn Arg Phe Leu Leu Thr Gly Gly Thr Asn Leu Asn Gly Lys Ile Ser
            660                 665                 670
Val Thr Gln Gly Asn Val Leu Leu Ser Gly Arg Pro Thr Pro His Ala
        675                 680                 685
Arg Asp Phe Val Asn Lys Ser Ser Ala Arg Lys Asp Ala His Phe Ser
    690                 695                 700
```

```
Lys Asn Asn Glu Val Val Phe Glu Asp Asp Trp Ile Asn Arg Thr Phe
705                 710                 715                 720

Lys Ala Thr Glu Ile Ala Val Asn Gln Ser Ala Ser Phe Ser Ser Gly
                725                 730                 735

Arg Asn Val Ser Asp Ile Thr Ala Asn Ile Thr Ala Thr Asp Asn Ala
            740                 745                 750

Lys Val Asn Leu Gly Tyr Lys Asn Gly Asp Glu Val Cys Val Arg Ser
        755                 760                 765

Asp Tyr Thr Gly Tyr Val Thr Cys Asn Thr Gly Asn Leu Ser Asp Lys
    770                 775                 780

Ala Leu Asn Ser Phe Gly Ala Thr Gln Ile Asn Gly Asn Val Asn Leu
785                 790                 795                 800

Asn Gln Asn Ala Ala Leu Val Leu Gly Lys Ala Ala Leu Trp Gly Gln
                805                 810                 815

Ile Gln Gly Gln Gly Asn Ser Arg Val Ser Leu Asn Gln His Ser Lys
            820                 825                 830

Trp His Leu Thr Gly Asp Ser Gln Val His Asn Leu Ser Leu Ala Asp
        835                 840                 845

Ser His Ile His Leu Asn Asn Ala Ser Asp Ala Gln Ser Ala Asn Lys
    850                 855                 860

Tyr His Thr Leu Lys Ile Asn His Leu Ser Gly Asn Gly His Phe His
865                 870                 875                 880

Tyr Leu Thr His Leu Ala Lys Asn Leu Gly Asp Lys Val Leu Val Lys
                885                 890                 895

Glu Ser Ala Ser Gly His Tyr Gln Leu His Val Gln Asp Lys Thr Gly
            900                 905                 910

Glu Pro Asn Gln Glu Gly Leu Asn Leu Phe Asp Ala Ser Ser Val Gln
        915                 920                 925

Asp Arg Ser Arg Leu Ser Val Ser Leu Ala Asn Asn His Val Asp Leu
    930                 935                 940

Gly Ala Leu Arg Tyr Thr Ile Lys Thr Glu Asn Gly Ile Thr Arg Leu
945                 950                 955                 960

Tyr Asn Pro Tyr Ala Glu Asn Arg Arg Val Lys Pro Ala Pro Ser
                965                 970                 975

Pro Ala Thr Asn Thr Ala Ser Gln Ala Gln Lys Ala Thr Gln Thr Asp
            980                 985                 990

Gly Ala Gln Ile Ala Lys Pro Gln Asn Ile Val Val Ala Pro Pro Ser
        995                 1000                1005

Pro Gln Ala Asn Gln Ala Glu Glu Ala Lys Arg Gln Gln Ala Lys Ala
    1010                1015                1020

Glu Gln Val Lys Arg Gln Gln Ala Glu Ala Glu Arg Lys Ser Ala Glu
1025                1030                1035                1040

Leu Ala Lys Gln Lys Ala Glu Ala Glu Arg Glu Ala Arg Glu Leu Ala
                1045                1050                1055

Thr Arg Gln Lys Ala Glu Gln Glu Arg Ser Ser Ala Glu Leu Ala Arg
            1060                1065                1070

Arg His Glu Lys Glu Arg Glu Ala Ala Glu Leu Ser Ala Lys Gln Lys
        1075                1080                1085

Val Glu Ala Glu Arg Glu Ala Gln Ala Leu Ala Val Arg Arg Lys Ala
    1090                1095                1100

Glu Ala Glu Glu Ala Lys Arg Gln Ala Ala Glu Leu Ala Arg Arg His
1105                1110                1115                1120

Glu Lys Glu Arg Glu Ala Ala Glu Leu Ser Ala Lys Gln Arg Val Gly
```

```
                    1125              1130              1135

Glu Glu Glu Arg Arg Gln Thr Ala Gln Ser Gln Pro Gln Arg Arg Lys
                1140              1145              1150

Arg Arg Ala Ala Pro Gln Asp Tyr Met Ala Ala Ser Gln Asp Arg Pro
        1155              1160              1165

Lys Arg Arg Gly His Arg Ser Val Gln Gln Asn Asn Val Glu Ile Ala
    1170              1175              1180

Gln Ala Gln Ala Glu Leu Ala Arg Arg Gln Gln Glu Glu Arg Lys Ala
1185              1190              1195              1200

Ala Glu Leu Leu Ala Lys Gln Arg Ala Glu Ala Glu Arg Glu Ala Gln
            1205              1210              1215

Ala Leu Ala Ala Arg Arg Lys Ala Glu Ala Glu Glu Ala Lys Arg Gln
            1220              1225              1230

Ala Ala Glu Leu Ala His Arg Gln Glu Ala Glu Arg Lys Ala Ala Glu
            1235              1240              1245

Leu Ser Ala Asn Gln Lys Ala Ala Ala Glu Ala Gln Ala Leu Ala Ala
            1250              1255              1260

Arg Gln Gln Lys Ala Leu Ala Arg Gln Glu Glu Ala Arg Lys Ala
1265              1270              1275              1280

Ala Glu Leu Ala Val Lys Gln Lys Ala Glu Thr Glu Arg Lys Thr Ala
            1285              1290              1295

Glu Leu Ala Lys Gln Arg Ala Ala Glu Ala Ala Lys Arg Gln Gln
            1300              1305              1310

Glu Ala Arg Gln Thr Ala Glu Leu Ala Arg Arg Gln Glu Ala Glu Arg
            1315              1320              1325

Gln Ala Ala Glu Leu Ser Ala Lys Gln Lys Ala Glu Thr Asp Arg Glu
        1330              1335              1340

Ala Ala Glu Ser Ala Lys Arg Lys Ala Glu Glu Glu His Arg Gln
1345              1350              1355              1360

Ala Ala Gln Ser Gln Pro Gln Arg Arg Lys Arg Arg Ala Ala Pro Gln
            1365              1370              1375

Asp Tyr Met Ala Ala Ser Gln Asn Arg Pro Lys Arg Arg Gly Arg Arg
            1380              1385              1390

Ser Thr Leu Pro Ala Pro Pro Ser Pro Ser Phe Asp Ser Ser Ala Tyr
            1395              1400              1405

Ala Ala Pro Arg Ala Leu His Asn Pro Asp Trp Tyr Glu Asn Asp Tyr
        1410              1415              1420

Glu Glu Ile Pro Leu Asp Ala Leu Glu Asp Glu Asn Val Ser Glu Ser
1425              1430              1435              1440

Val Asp Thr Ser Asp Lys Gln Pro Gln Asp Asn Thr Glu Leu His Glu
                1445              1450              1455

Lys Tyr Glu Asn Asp Tyr Glu Glu Ile Pro Leu Asp Ala Leu Glu Asp
            1460              1465              1470

Glu Asp Val Ser Glu Ser Val Asp Thr Ser Asp Lys Gln Pro Gln Asp
            1475              1480              1485

Asn Thr Glu Leu His Glu Lys Val Glu Thr Val Ser Leu Gln Pro Arg
    1490              1495              1500

Ala Ala Gln Pro Arg Ala Gln Ala Ala Thr Gln Leu Gln Ala Gln Ala
1505              1510              1515              1520

Ala Ala Gln Ala Asp Ala Val Ser Thr Asn Thr Asn Ser Ala Leu Ser
            1525              1530              1535

Asp Ala Met Ala Ser Thr Gln Ser Ile Leu Leu Asp Thr Gly Ala Ser
            1540              1545              1550
```

```
Leu Thr Arg His Ile Ala Gln Lys Ser Arg Ala Asp Ala Glu Lys Asn
        1555                1560                1565

Ser Val Trp Met Ser Asn Thr Gly Tyr Gly Arg Asp Tyr Ala Ser Ala
    1570                1575                1580

Gln Tyr Arg Arg Phe Ser Ser Lys Arg Thr Gln Thr Gln Ile Gly Ile
1585                1590                1595                1600

Asp Arg Ser Leu Ser Glu Asn Met Gln Ile Gly Gly Val Leu Thr Tyr
            1605                1610                1615

Ser Asp Ser Gln His Thr Phe Asp Gln Ala Ser Gly Lys Asn Thr Phe
        1620                1625                1630

Val Gln Ala Asn Leu Tyr Gly Lys Tyr Tyr Leu Asn Asp Ala Trp Tyr
    1635                1640                1645

Val Ala Gly Asp Ile Gly Ala Gly Ser Leu Arg Ser Arg Leu Gln Thr
1650                1655                1660

Gln Gln Lys Ala Asn Phe Asn Arg Ala Ser Ile Gln Thr Gly Leu Thr
1665                1670                1675                1680

Leu Gly Asn Thr Leu Lys Ile Asn Gln Phe Glu Ile Val Pro Ser Ala
            1685                1690                1695

Gly Ile Arg Tyr Ser Arg Leu Ser Ala Asp Tyr Lys Leu Gly Asn
        1700                1705                1710

Asp Ser Val Lys Val Ser Ser Met Ser Val Lys Thr Leu Thr Ala Gly
    1715                1720                1725

Leu Asp Phe Ala Tyr Arg Phe Lys Val Gly Asn Leu Thr Val Lys Pro
1730                1735                1740

Leu Leu Ser Ala Ala Tyr Phe Ala Asn Tyr Gly Lys Gly Gly Val Asn
1745                1750                1755                1760

Val Gly Gly Asn Ser Phe Val Tyr Lys Ala Asp Asn Gln Gln Gln Tyr
            1765                1770                1775

Ser Ala Gly Ala Ala Leu Leu Tyr Arg Asn Val Thr Leu Asn Val Asn
        1780                1785                1790

Gly Ser Ile Thr Lys Gly Lys Gln Leu Glu Lys Gln Lys Ser Gly Gln
    1795                1800                1805

Ile Lys Ile Gln Ile Arg Phe
    1810                1815

<210> SEQ ID NO 2
<211> LENGTH: 1457
<212> TYPE: PRT
<213> ORGANISM: Neisseria meningitidis

<400> SEQUENCE: 2

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
```

```
              100                 105                 110
Val Ala His Asn Gly Gly Tyr Asn Asn Val Asp Phe Gly Ala Glu Gly
              115                 120                 125

Arg Asn Pro Asp Gln His Arg Phe Thr Tyr Lys Ile Val Lys Arg Asn
              130                 135                 140

Asn Tyr Lys Ala Gly Thr Lys Gly His Pro Tyr Gly Gly Asp Tyr His
145               150                 155                 160

Met Pro Arg Leu His Lys Phe Val Thr Asp Ala Glu Pro Val Glu Met
              165                 170                 175

Thr Ser Tyr Met Asp Gly Arg Lys Tyr Ile Asp Gln Asn Asn Tyr Pro
              180                 185                 190

Asp Arg Val Arg Ile Gly Ala Gly Arg Gln Tyr Trp Arg Ser Asp Glu
              195                 200                 205

Asp Glu Pro Asn Asn Arg Glu Ser Ser Tyr His Ile Ala Ser Ala Tyr
              210                 215                 220

Ser Trp Leu Val Gly Gly Asn Thr Phe Ala Gln Asn Gly Ser Gly Gly
225               230                 235                 240

Gly Thr Val Asn Leu Gly Ser Glu Lys Ile Lys His Ser Pro Tyr Gly
              245                 250                 255

Phe Leu Pro Thr Gly Gly Ser Phe Gly Asp Ser Gly Ser Pro Met Phe
              260                 265                 270

Ile Tyr Asp Ala Gln Lys Gln Lys Trp Leu Ile Asn Gly Val Leu Gln
              275                 280                 285

Thr Gly Asn Pro Tyr Ile Gly Lys Ser Asn Gly Phe Gln Leu Val Arg
              290                 295                 300

Lys Asp Trp Phe Tyr Asp Glu Ile Phe Ala Gly Asp Thr His Ser Val
305               310                 315                 320

Phe Tyr Glu Pro Arg Gln Asn Gly Lys Tyr Ser Phe Asn Asp Asp Asn
              325                 330                 335

Asn Gly Thr Gly Lys Ile Asn Ala Lys His Glu His Asn Ser Leu Pro
              340                 345                 350

Asn Arg Leu Lys Thr Arg Thr Val Gln Leu Phe Asn Val Ser Leu Ser
              355                 360                 365

Glu Thr Ala Arg Glu Pro Val Tyr His Ala Ala Gly Gly Val Asn Ser
              370                 375                 380

Tyr Arg Pro Arg Leu Asn Asn Gly Glu Asn Ile Ser Phe Ile Asp Glu
385               390                 395                 400

Gly Lys Gly Glu Leu Ile Leu Thr Ser Asn Ile Asn Gln Gly Ala Gly
              405                 410                 415

Gly Leu Tyr Phe Gln Gly Asp Phe Thr Val Ser Pro Glu Asn Asn Glu
              420                 425                 430

Thr Trp Gln Gly Ala Gly Val His Ile Ser Glu Asp Ser Thr Val Thr
              435                 440                 445

Trp Lys Val Asn Gly Val Ala Asn Asp Arg Leu Ser Lys Ile Gly Lys
              450                 455                 460

Gly Thr Leu His Val Gln Ala Lys Gly Glu Asn Gln Gly Ser Ile Ser
465               470                 475                 480

Val Gly Asp Gly Thr Val Ile Leu Asp Gln Gln Ala Asp Asp Lys Gly
              485                 490                 495

Lys Lys Gln Ala Phe Ser Glu Ile Gly Leu Val Ser Gly Arg Gly Thr
              500                 505                 510

Val Gln Leu Asn Ala Asp Asn Gln Phe Asn Pro Asp Lys Leu Tyr Phe
              515                 520                 525
```

```
Gly Phe Arg Gly Gly Arg Leu Asp Leu Asn Gly His Ser Leu Ser Phe
            530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
            595                 600                 605

Asn Leu Val Tyr Gln Pro Ala Ala Glu Asp Arg Thr Leu Leu Leu Ser
            610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
            675                 680                 685

Gly Gly Gln Ala Val Val Ser Arg Asn Val Ala Lys Val Lys Gly Asp
            690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
                740                 745                 750

Lys Thr Asp Ile Ser Gly Asn Val Asp Leu Ala Asp His Ala His Leu
            755                 760                 765

Asn Leu Thr Gly Leu Ala Thr Leu Asn Gly Asn Leu Ser Ala Asn Gly
            770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
            835                 840                 845

Val Ser His Ser Ala Leu Asn Gly Asn Val Ser Leu Ala Asp Lys Ala
850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
            915                 920                 925

Thr Asp Ala Pro Arg Arg Ser Arg Arg Ser Arg Arg Ser Leu Leu
930                 935                 940
```

```
Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
            965                 970                 975

Leu Phe Gly Tyr Arg Ser Asp Lys Leu Lys Leu Ala Glu Ser Ser Glu
        980                 985                 990

Gly Thr Tyr Thr Leu Ala Val Asn Asn Thr Gly Asn Glu Pro Ala Ser
    995                 1000                1005

Leu Glu Gln Leu Thr Val Val Glu Gly Lys Asp Asn Lys Pro Leu Ser
1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
            1045                1050                1055

Pro Val Lys Glu Gln Glu Leu Ser Asp Lys Leu Gly Lys Ala Glu Ala
            1060                1065                1070

Lys Lys Gln Ala Glu Lys Asp Asn Ala Gln Ser Leu Asp Ala Leu Ile
        1075                1080                1085

Ala Ala Gly Arg Asp Ala Val Glu Lys Thr Glu Ser Val Ala Glu Pro
1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
            1125                1130                1135

Arg Glu Ala Glu Thr Arg Pro Ala Thr Thr Ala Phe Pro Arg Ala Arg
            1140                1145                1150

Arg Ala Arg Arg Asp Leu Pro Gln Leu Gln Pro Gln Pro Gln Pro Gln
        1155                1160                1165

Pro Gln Arg Asp Leu Ile Ser Arg Tyr Ala Asn Ser Gly Leu Ser Glu
1170                1175                1180

Phe Ser Ala Thr Leu Asn Ser Val Phe Ala Val Gln Asp Glu Leu Asp
1185                1190                1195                1200

Arg Val Phe Ala Glu Asp Arg Arg Asn Ala Val Trp Thr Ser Gly Ile
            1205                1210                1215

Arg Asp Thr Lys His Tyr Arg Ser Gln Asp Phe Arg Ala Tyr Arg Gln
            1220                1225                1230

Gln Thr Asp Leu Arg Gln Ile Gly Met Gln Lys Asn Leu Gly Ser Gly
        1235                1240                1245

Arg Val Gly Ile Leu Phe Ser His Asn Arg Thr Glu Asn Thr Phe Asp
1250                1255                1260

Asp Gly Ile Gly Asn Ser Ala Arg Leu Ala His Gly Ala Val Phe Gly
1265                1270                1275                1280

Gln Tyr Gly Ile Asp Arg Phe Tyr Ile Gly Ile Ser Ala Gly Ala Gly
            1285                1290                1295

Phe Ser Ser Gly Ser Leu Ser Asp Gly Ile Gly Gly Lys Ile Arg Arg
            1300                1305                1310

Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
```

```
                    1365               1370                1375
    Pro Ala Gln His Ile Ser Ile Thr Pro Tyr Leu Ser Leu Ser Tyr Thr
                    1380                1385                1390

Asp Ala Ala Ser Gly Lys Val Arg Thr Arg Val Asn Thr Ala Val Leu
                    1395                1400                1405

Ala Gln Asp Phe Gly Lys Thr Arg Ser Ala Glu Trp Gly Val Asn Ala
            1410                1415                1420

Glu Ile Lys Gly Phe Thr Leu Ser Leu His Ala Ala Ala Lys Gly
    1425                1430                1435                1440

Pro Gln Leu Glu Ala Gln His Ser Ala Gly Ile Lys Leu Gly Tyr Arg
                    1445                1450                1455

Trp

<210> SEQ ID NO 3
<211> LENGTH: 1431
<212> TYPE: PRT
<213> ORGANISM: Neisseria meningitidis

<400> SEQUENCE: 3

Met Arg Phe Thr His Thr Thr Pro Phe Cys Ser Val Leu Ser Thr Leu
1               5                   10                  15

Gly Leu Phe Ala Val Ser Pro Ala Tyr Ser Ser Ile Val Arg Asn Asp
                20                  25                  30

Val Asp Tyr Gln Tyr Phe Arg Asp Phe Ala Glu Asn Lys Gly Ala Phe
            35                  40                  45

Thr Val Gly Ala Ser Asn Ile Ser Ile Gln Asp Lys Gln Gly Lys Ile
        50                  55                  60

Leu Gly Arg Val Leu Asn Gly Ile Pro Met Pro Asp Phe Arg Val Ser
65                  70                  75                  80

Asn Arg Gln Thr Ala Ile Ala Thr Leu Val His Pro Gln Tyr Val Asn
                85                  90                  95

Ser Val Lys His Asn Val Gly Tyr Gly Ser Ile Gln Phe Gly Asn Asp
                100                 105                 110

Thr Gln Asn Pro Glu Glu Gln Ala Tyr Thr Tyr Arg Leu Val Ser Arg
            115                 120                 125

Asn Pro His Pro Asp Tyr Asp Tyr His Leu Pro Arg Leu Asn Lys Leu
        130                 135                 140

Val Thr Glu Ile Ser Pro Thr Ala Leu Ser Ser Val Pro Leu Leu Gly
145                 150                 155                 160

Asn Gly Gln Pro Lys Ala Asn Ala Tyr Leu Asp Thr Asp Arg Phe Pro
                165                 170                 175

Tyr Phe Val Arg Leu Gly Ser Gly Thr Gln Gln Val Arg Lys Ala Asp
                180                 185                 190

Gly Thr Arg Thr Arg Thr Ala Pro Ala Tyr Gln Tyr Leu Thr Gly Gly
            195                 200                 205

Thr Pro Leu Lys Val Leu Gly Phe Gln Asn His Gly Leu Leu Val Gly
        210                 215                 220

Gly Ser Leu Thr Asp Gln Pro Leu Asn Thr Tyr Ala Ile Ala Gly Asp
225                 230                 235                 240

Ser Gly Ser Pro Leu Phe Ala Phe Asp Lys His Glu Asn Arg Trp Val
                245                 250                 255

Leu Ala Gly Val Leu Ser Thr Tyr Ala Gly Phe Asp Asn Phe Phe Asn
                260                 265                 270

Lys Tyr Ile Val Thr Gln Pro Glu Phe Ile Arg Ser Thr Ile Arg Gln
```

-continued

```
                275                 280                 285
Tyr Glu Thr Arg Leu Asp Val Gly Leu Thr Thr Asn Glu Leu Ile Trp
290                 295                 300

Arg Asp Asn Gly Asn Gly Asn Ser Thr Leu Gln Gly Leu Asn Glu Arg
305                 310                 315                 320

Ile Thr Leu Pro Ile Ala Asn Pro Ser Leu Ala Pro Gln Asn Asp Ser
                325                 330                 335

Arg His Met Pro Ser Glu Asp Ala Gly Lys Thr Leu Ile Leu Ser Ser
                340                 345                 350

Arg Phe Asp Asn Lys Thr Leu Met Leu Ala Asp Asn Ile Asn Gln Gly
                355                 360                 365

Ala Gly Ala Leu Gln Phe Asp Ser Asn Phe Thr Val Val Gly Lys Asn
370                 375                 380

His Thr Trp Gln Gly Ala Gly Val Ile Val Ala Asp Gly Lys Arg Val
385                 390                 395                 400

Phe Trp Gln Val Ser Asn Pro Lys Gly Asp Arg Leu Ser Lys Leu Gly
                405                 410                 415

Ala Gly Thr Leu Ile Ala Asn Gly Gln Gly Ile Asn Gln Gly Asp Ile
                420                 425                 430

Ser Ile Gly Glu Gly Thr Val Val Leu Ala Gln Lys Ala Ala Ser Asp
                435                 440                 445

Gly Ser Lys Gln Ala Phe Asn Gln Val Gly Ile Thr Ser Gly Arg Gly
450                 455                 460

Thr Ala Val Leu Ala Asp Ser Gln Gln Ile Lys Pro Glu Asn Leu Tyr
465                 470                 475                 480

Phe Gly Phe Arg Gly Gly Arg Leu Asp Leu Asn Gly Asn Asn Leu Ala
                485                 490                 495

Phe Thr His Ile Arg His Ala Asp Gly Gly Ala Gln Ile Val Asn His
                500                 505                 510

Asn Pro Asp Gln Ala Ala Thr Leu Thr Leu Thr Gly Asn Pro Val Leu
                515                 520                 525

Ser Pro Glu His Val Glu Trp Val Gln Trp Gly Asn Arg Pro Gln Gly
530                 535                 540

Asn Ala Ala Val Tyr Glu Tyr Ile Asn Pro His Arg Asn Arg Arg Thr
545                 550                 555                 560

Asp Tyr Phe Ile Leu Lys Pro Gly Gly Asn Pro Arg Glu Phe Phe Pro
                565                 570                 575

Leu Asn Met Lys Asn Ser Thr Ser Trp Gln Phe Ile Gly Asn Asn Arg
                580                 585                 590

Gln Gln Ala Ala Glu Gln Val Ala Gln Ala Glu Asn Ala Arg Pro Asp
                595                 600                 605

Leu Ile Thr Phe Gly Gly Tyr Leu Gly Glu Asn Ala Gln Thr Gly Lys
610                 615                 620

Ala Ala Pro Ser Tyr Ser Lys Thr Asn Glu Ala Ile Glu Lys Thr
625                 630                 635                 640

Arg His Ile Ala Asn Ala Ala Val Tyr Gly Arg Pro Glu Tyr Arg Tyr
                645                 650                 655

Asn Gly Ala Leu Asn Leu His Tyr Arg Pro Lys Arg Thr Asp Ser Thr
                660                 665                 670

Leu Leu Leu Asn Gly Gly Met Asn Leu Asn Gly Glu Val Leu Ile Glu
                675                 680                 685

Gly Gly Asn Met Ile Val Ser Gly Arg Pro Val Pro His Ala Tyr Asp
690                 695                 700
```

```
His Gln Ala Lys Arg Glu Pro Val Leu Glu Asn Glu Trp Thr Asp Gly
705                 710                 715                 720

Ser Phe Lys Ala Ala Arg Phe Thr Leu Arg Asn His Ala Arg Leu Thr
            725                 730                 735

Ala Gly Arg Asn Thr Ala His Leu Asp Gly Asp Ile Thr Ala Tyr Asp
        740                 745                 750

Leu Ser Gly Ile Asp Leu Gly Phe Thr Gln Gly Lys Thr Pro Glu Cys
    755                 760                 765

Tyr Arg Ser Tyr His Ser Gly Ser Thr His Cys Thr Pro Asn Ala Val
770                 775                 780

Leu Lys Ala Glu Asn Tyr Arg Ala Leu Pro Ala Thr Gln Val Arg Gly
785                 790                 795                 800

Asp Ile Thr Leu Asn Asp Arg Ser Glu Leu Arg Leu Gly Lys Ala His
            805                 810                 815

Leu Tyr Gly Ser Ile Arg Ala Gly Lys Asp Thr Ala Val Arg Met Glu
        820                 825                 830

Ala Asp Ser Asn Trp Thr Leu Ser Gln Ser Ser His Thr Gly Ala Leu
    835                 840                 845

Thr Leu Asp Gly Ala Gln Ile Thr Leu Asn Pro Asp Phe Ala Asn Asn
850                 855                 860

Thr His Asn Asn Arg Phe Asn Thr Leu Thr Val Asn Gly Thr Leu Asp
865                 870                 875                 880

Gly Phe Gly Thr Phe Arg Phe Leu Thr Gly Ile Val Arg Lys Gln Asn
            885                 890                 895

Ala Pro Pro Leu Lys Leu Glu Gly Asp Ser Arg Gly Ala Phe Gln Ile
        900                 905                 910

His Val Lys Asn Thr Gly Gln Glu Pro Gln Thr Thr Glu Ser Leu Ala
    915                 920                 925

Leu Val Ser Leu Asn Pro Lys His Ser His Gln Ala Arg Phe Thr Leu
930                 935                 940

Gln Asn Gly Tyr Ala Asp Leu Gly Ala Tyr Arg Tyr Ile Leu Arg Lys
945                 950                 955                 960

Asn Asn Asn Gly Tyr Ser Leu Tyr Asn Pro Leu Lys Glu Ala Glu Leu
            965                 970                 975

Gln Ile Glu Ala Thr Arg Ala Glu His Glu Arg Asn Gln Gln Ala Tyr
        980                 985                 990

Asn Gln Leu Gln Ala Thr Asp Ile Ser Arg Gln Val Gln His Asp Ser
    995                 1000                1005

Asp Ala Thr Arg Gln Ala Leu Gln Ala Trp Gln Asn Ser Gln Thr Glu
    1010                1015                1020

Leu Ala Arg Ile Asp Ser Gln Val Gln Tyr Leu Ser Ala Gln Leu Lys
1025                1030                1035                1040

Gln Thr Asp Pro Leu Thr Gly Ile Leu Thr Arg Ala Gln Asn Leu Cys
            1045                1050                1055

Ala Ala Gln Gly Tyr Ser Ala Asp Ile Cys Arg Gln Val Ala Lys Ala
        1060                1065                1070

Ala Asp Thr Asn Asp Leu Thr Leu Phe Glu Thr Glu Leu Asp Thr Tyr
    1075                1080                1085

Ile Glu Arg Val Glu Met Ala Glu Ser Glu Leu Asp Lys Ala Arg Gln
    1090                1095                1100

Gly Gly Asp Ala Gln Ala Val Glu Thr Ala Arg His Ala Tyr Leu Asn
1105                1110                1115                1120
```

```
Ala Leu Asn Arg Leu Ser Arg Gln Ile His Ser Leu Lys Thr Gly Val
            1125                1130                1135

Ala Gly Ile Arg Met Pro Asn Leu Ala Glu Leu Ile Ser Arg Ser Ala
            1140                1145                1150

Asn Thr Ala Val Ser Glu Gln Ala Ala Tyr Asn Thr Gly Arg Gln Gln
            1155                1160                1165

Ala Gly Arg Arg Ile Asp Arg His Leu Thr Asp Pro Gln Gln Gln Asn
        1170                1175                1180

Ile Trp Leu Glu Thr Gly Thr Gln Gln Thr Asp Tyr His Ser Gly Thr
1185                1190                1195                1200

His Arg Pro Tyr Gln Gln Thr Thr Asn Tyr Ala His Ile Gly Ile Gln
            1205                1210                1215

Thr Gly Ile Thr Asp Arg Leu Ser Val Gly Thr Ile Leu Thr Asp Glu
            1220                1225                1230

Arg Thr Asn Asn Arg Phe Asp Glu Gly Val Ser Ala Arg Asn Arg Ser
            1235                1240                1245

Asn Gly Ala His Leu Phe Val Lys Gly Glu Asn Gly Ala Leu Phe Ala
            1250                1255                1260

Ala Ala Asp Leu Gly Tyr Ser Asn Ser Arg Thr Arg Phe Thr Asp Tyr
1265                1270                1275                1280

Asp Gly Ala Ala Val Arg Arg His Ala Trp Asp Ala Gly Ile Asn Thr
            1285                1290                1295

Gly Ile Lys Ile Asp Thr Gly Ile Asn Leu Arg Pro Tyr Ala Gly Ile
            1300                1305                1310

Arg Ile Asn Arg Ser Asn Gly Asn Arg Tyr Val Leu Asp Gly Ala Glu
            1315                1320                1325

Ile Asn Ser Pro Ala Gln Ile Gln Thr Thr Trp His Ala Gly Ile Arg
            1330                1335                1340

Leu Asp Lys Thr Val Glu Leu Gly Gln Ala Lys Leu Thr Pro Ala Phe
1345                1350                1355                1360

Ser Ser Asp Tyr Tyr His Thr Arg Gln Asn Ser Gly Ser Ala Leu Ser
            1365                1370                1375

Val Asn Asp Arg Thr Leu Leu Gln Gln Ala Ala His Gly Thr Leu His
            1380                1385                1390

Thr Leu Gln Ile Asp Ala Gly Tyr Lys Gly Trp Asn Ala Lys Leu His
            1395                1400                1405

Ala Ala Tyr Gly Lys Asp Ser Asn Thr Ala Arg His Lys Gln Ala Gly
            1410                1415                1420

Ile Lys Ile Gly Tyr Asn Trp
1425                1430

<210> SEQ ID NO 4
<211> LENGTH: 1082
<212> TYPE: PRT
<213> ORGANISM: Neisseria meningitidis

<400> SEQUENCE: 4

Met Arg Thr Thr Pro Thr Phe Pro Lys Thr Phe Lys Pro Thr Ala
1               5                   10                  15

Met Ala Leu Ala Val Ala Thr Leu Ser Ala Cys Leu Gly Gly Gly
                20                  25                  30

Gly Gly Gly Thr Ser Ala Pro Asp Phe Asn Ala Gly Gly Thr Gly Ile
            35                  40                  45

Gly Ser Asn Ser Arg Ala Thr Thr Ala Lys Ser Ala Ala Val Ser Tyr
        50                  55                  60
```

```
Ala Gly Ile Lys Asn Glu Met Cys Lys Asp Arg Ser Met Leu Cys Ala
 65                  70                  75                  80

Gly Arg Asp Asp Val Ala Val Thr Asp Arg Asp Ala Lys Ile Asn Ala
                 85                  90                  95

Pro Pro Pro Asn Leu His Thr Gly Asp Phe Pro Asn Pro Asn Asp Ala
            100                 105                 110

Tyr Lys Asn Leu Ile Asn Leu Lys Pro Ala Ile Glu Ala Gly Tyr Thr
                115                 120                 125

Gly Arg Gly Val Glu Val Gly Ile Val Asp Thr Gly Glu Ser Val Gly
130                 135                 140

Ser Ile Ser Phe Pro Glu Leu Tyr Gly Arg Lys Glu His Gly Tyr Asn
145                 150                 155                 160

Glu Asn Tyr Lys Asn Tyr Thr Ala Tyr Met Arg Lys Glu Ala Pro Glu
                165                 170                 175

Asp Gly Gly Lys Asp Ile Glu Ala Ser Phe Asp Asp Glu Ala Val
                180                 185                 190

Ile Glu Thr Glu Ala Lys Pro Thr Asp Ile Arg His Val Lys Glu Ile
            195                 200                 205

Gly His Ile Asp Leu Val Ser His Ile Ile Gly Gly Arg Ser Val Asp
210                 215                 220

Gly Arg Pro Ala Gly Gly Ile Ala Pro Asp Ala Thr Leu His Ile Met
225                 230                 235                 240

Asn Thr Asn Asp Glu Thr Lys Asn Glu Met Met Val Ala Ala Ile Arg
                245                 250                 255

Asn Ala Trp Lys Leu Gly Glu Arg Gly Val Arg Ile Val Asn Asn
            260                 265                 270

Ser Phe Gly Thr Thr Ser Arg Ala Gly Thr Ala Asp Leu Phe Gln Ile
            275                 280                 285

Ala Asn Ser Glu Glu Gln Tyr Arg Gln Ala Leu Leu Asp Tyr Ser Gly
            290                 295                 300

Gly Asp Lys Thr Asp Glu Gly Ile Arg Leu Met Gln Gln Ser Asp Tyr
305                 310                 315                 320

Gly Asn Leu Ser Tyr His Ile Arg Asn Lys Asn Met Leu Phe Ile Phe
                325                 330                 335

Ser Thr Gly Asn Asp Ala Gln Ala Gln Pro Asn Thr Tyr Ala Leu Leu
            340                 345                 350

Pro Phe Tyr Glu Lys Asp Ala Gln Lys Gly Ile Ile Thr Val Ala Gly
            355                 360                 365

Val Asp Arg Ser Gly Glu Lys Phe Lys Arg Glu Met Tyr Gly Glu Pro
            370                 375                 380

Gly Thr Glu Pro Leu Glu Tyr Gly Ser Asn His Cys Gly Ile Thr Ala
385                 390                 395                 400

Met Trp Cys Leu Ser Ala Pro Tyr Glu Ala Ser Val Arg Phe Thr Arg
                405                 410                 415

Thr Asn Pro Ile Gln Ile Ala Gly Thr Ser Phe Ser Ala Pro Ile Val
            420                 425                 430

Thr Gly Thr Ala Ala Leu Leu Leu Gln Lys Tyr Pro Trp Met Ser Asn
            435                 440                 445

Asp Asn Leu Arg Thr Thr Leu Leu Thr Thr Ala Gln Asp Ile Gly Ala
            450                 455                 460

Val Gly Val Asp Ser Lys Phe Gly Trp Gly Leu Leu Asp Ala Gly Lys
465                 470                 475                 480
```

-continued

```
Ala Met Asn Gly Pro Ala Ser Phe Pro Phe Gly Asp Phe Thr Ala Asp
            485                 490                 495
Thr Lys Gly Thr Ser Asp Ile Ala Tyr Ser Phe Arg Asn Asp Ile Ser
        500                 505                 510
Gly Thr Gly Gly Leu Ile Lys Lys Gly Gly Ser Gln Leu Gln Leu His
        515                 520                 525
Gly Asn Asn Thr Tyr Thr Gly Lys Thr Ile Ile Glu Gly Gly Ser Leu
    530                 535                 540
Val Leu Tyr Gly Asn Asn Lys Ser Asp Met Arg Val Glu Thr Lys Gly
545                 550                 555                 560
Ala Leu Ile Tyr Asn Gly Ala Ala Ser Gly Gly Ser Leu Asn Ser Asp
                565                 570                 575
Gly Ile Val Tyr Leu Ala Asp Thr Asp Gln Ser Gly Ala Asn Glu Thr
            580                 585                 590
Val His Ile Lys Gly Ser Leu Gln Leu Asp Gly Lys Gly Thr Leu Tyr
        595                 600                 605
Thr Arg Leu Gly Lys Leu Leu Lys Val Asp Gly Thr Ala Ile Ile Gly
    610                 615                 620
Gly Lys Leu Tyr Met Ser Ala Arg Gly Lys Gly Ala Gly Tyr Leu Asn
625                 630                 635                 640
Ser Thr Gly Arg Arg Val Pro Phe Leu Ser Ala Ala Lys Ile Gly Gln
                645                 650                 655
Asp Tyr Ser Phe Phe Thr Asn Ile Glu Thr Asp Gly Gly Leu Leu Ala
            660                 665                 670
Ser Leu Asp Ser Val Glu Lys Thr Ala Gly Ser Glu Gly Asp Thr Leu
        675                 680                 685
Ser Tyr Tyr Val Arg Arg Gly Asn Ala Ala Arg Thr Ala Ser Ala Ala
    690                 695                 700
Ala His Ser Ala Pro Ala Gly Leu Lys His Ala Val Glu Gln Gly Gly
705                 710                 715                 720
Ser Asn Leu Glu Asn Leu Met Val Glu Leu Asp Ala Ser Glu Ser Ser
                725                 730                 735
Ala Thr Pro Glu Thr Val Glu Thr Ala Ala Ala Asp Arg Thr Asp Met
            740                 745                 750
Pro Gly Ile Arg Pro Tyr Gly Ala Thr Phe Arg Ala Ala Ala Ala Val
        755                 760                 765
Gln His Ala Asn Ala Ala Asp Gly Val Arg Ile Phe Asn Ser Leu Ala
    770                 775                 780
Ala Thr Val Tyr Ala Asp Ser Thr Ala His Ala Asp Met Gln Gly
785                 790                 795                 800
Arg Arg Leu Lys Ala Val Ser Asp Gly Leu Asp His Asn Gly Thr Gly
                805                 810                 815
Leu Arg Val Ile Ala Gln Thr Gln Gln Asp Gly Gly Thr Trp Glu Gln
            820                 825                 830
Gly Gly Val Glu Gly Lys Met Arg Gly Ser Thr Gln Thr Val Gly Ile
        835                 840                 845
Ala Ala Lys Thr Gly Glu Asn Thr Thr Ala Ala Thr Leu Gly Met
    850                 855                 860
Gly Arg Ser Thr Trp Ser Glu Asn Ser Ala Ala Lys Thr Asp Ser
865                 870                 875                 880
Ile Ser Leu Phe Ala Gly Ile Arg His Asp Ala Gly Asp Ile Gly Tyr
                885                 890                 895
Leu Lys Gly Leu Phe Ser Tyr Gly Arg Tyr Lys Asn Ser Ile Ser Arg
```

```
              900             905             910
Ser Thr Gly Ala Asp Glu His Ala Glu Gly Ser Val Asn Gly Thr Leu
            915             920             925

Met Gln Leu Gly Ala Leu Gly Gly Val Asn Val Pro Phe Ala Ala Thr
        930             935             940

Gly Asp Leu Thr Val Glu Gly Gly Leu Arg Tyr Asp Leu Leu Lys Gln
945             950             955             960

Asp Ala Phe Ala Glu Lys Gly Ser Ala Leu Gly Trp Ser Gly Asn Ser
            965             970             975

Leu Thr Glu Gly Thr Leu Val Gly Leu Ala Gly Leu Lys Leu Ser Gln
            980             985             990

Pro Leu Ser Asp Lys Ala Val Leu Phe Ala Thr Ala Gly Val Glu Arg
            995            1000            1005

Asp Leu Asn Gly Arg Asp Tyr Thr Val Thr Gly Phe Thr Gly Ala
           1010            1015            1020

Thr Ala Ala Thr Gly Lys Thr Gly Ala Arg Asn Met Pro His Thr Arg
1025            1030            1035            1040

Leu Val Ala Gly Leu Gly Ala Asp Val Glu Phe Gly Asn Gly Trp Asn
           1045            1050            1055

Gly Leu Ala Arg Tyr Ser Tyr Ala Gly Ser Lys Gln Tyr Gly Asn His
           1060            1065            1070

Ser Gly Arg Val Gly Val Gly Tyr Arg Phe
           1075            1080

<210> SEQ ID NO 5
<211> LENGTH: 711
<212> TYPE: PRT
<213> ORGANISM: Neisseria meningitidis

<400> SEQUENCE: 5

Met Asn Asn Pro Leu Val Asn Gln Ala Ala Met Val Leu Pro Val Phe
1               5              10              15

Leu Leu Ser Ala Cys Leu Gly Gly Gly Gly Ser Phe Asp Leu Asp Ser
            20              25              30

Val Asp Thr Glu Ala Pro Arg Pro Ala Pro Lys Tyr Gln Asp Val Ser
        35              40              45

Ser Glu Lys Pro Gln Ala Gln Lys Asp Gln Gly Gly Tyr Gly Phe Ala
50              55              60

Met Arg Leu Lys Arg Arg Asn Trp Tyr Pro Gly Ala Glu Glu Ser Glu
65              70              75              80

Val Lys Leu Asn Glu Ser Asp Trp Glu Ala Thr Gly Leu Pro Thr Lys
            85              90              95

Pro Lys Glu Leu Pro Lys Arg Gln Lys Ser Val Ile Glu Lys Val Glu
        100             105             110

Thr Asp Gly Asp Ser Asp Ile Tyr Ser Ser Pro Tyr Leu Thr Pro Ser
    115             120             125

Asn His Gln Asn Gly Ser Ala Gly Asn Gly Val Asn Gln Pro Lys Asn
    130             135             140

Gln Ala Thr Gly His Glu Asn Phe Gln Tyr Val Tyr Ser Gly Trp Phe
145             150             155             160

Tyr Lys His Ala Ala Ser Glu Lys Asp Phe Ser Asn Lys Lys Ile Lys
            165             170             175

Ser Gly Asp Asp Gly Tyr Ile Phe Tyr His Gly Glu Lys Pro Ser Arg
            180             185             190
```

```
Gln Leu Pro Ala Ser Gly Lys Val Ile Tyr Lys Gly Val Trp His Phe
            195                 200                 205

Val Thr Asp Thr Lys Lys Gly Gln Asp Phe Arg Glu Ile Ile Gln Pro
        210                 215                 220

Ser Lys Lys Gln Gly Asp Arg Tyr Ser Gly Phe Ser Gly Asp Gly Ser
225                 230                 235                 240

Glu Glu Tyr Ser Asn Lys Asn Glu Ser Thr Leu Lys Asp Asp His Glu
                245                 250                 255

Gly Tyr Gly Phe Thr Ser Asn Leu Glu Val Asp Phe Gly Asn Lys Lys
            260                 265                 270

Leu Thr Gly Lys Leu Ile Arg Asn Asn Ala Ser Leu Asn Asn Asn Thr
        275                 280                 285

Asn Asn Asp Lys His Thr Thr Gln Tyr Tyr Ser Leu Asp Ala Gln Ile
290                 295                 300

Thr Gly Asn Arg Phe Asn Gly Thr Ala Thr Ala Thr Asp Lys Lys Glu
305                 310                 315                 320

Asn Glu Thr Lys Leu His Pro Phe Val Ser Asp Ser Ser Leu Ser
                325                 330                 335

Gly Gly Phe Phe Gly Pro Gln Gly Glu Glu Leu Gly Phe Arg Phe Leu
            340                 345                 350

Ser Asp Asp Gln Lys Val Ala Val Gly Ser Ala Lys Thr Lys Asp
        355                 360                 365

Lys Leu Glu Asn Gly Ala Ala Ala Ser Gly Ser Thr Gly Ala Ala Ala
        370                 375                 380

Ser Gly Gly Ala Ala Gly Thr Ser Ser Glu Asn Ser Lys Leu Thr Thr
385                 390                 395                 400

Val Leu Asp Ala Val Glu Leu Thr Leu Asn Asp Lys Lys Ile Lys Asn
                405                 410                 415

Leu Asp Asn Phe Ser Asn Ala Ala Gln Leu Val Val Asp Gly Ile Met
            420                 425                 430

Ile Pro Leu Leu Pro Lys Asp Ser Glu Ser Gly Asn Thr Gln Ala Asp
        435                 440                 445

Lys Gly Lys Asn Gly Gly Thr Glu Phe Thr Arg Lys Phe Glu His Thr
        450                 455                 460

Pro Glu Ser Asp Lys Lys Asp Ala Gln Ala Gly Thr Gln Thr Asn Gly
465                 470                 475                 480

Ala Gln Thr Ala Ser Asn Thr Ala Gly Asp Thr Asn Gly Lys Thr Lys
                485                 490                 495

Thr Tyr Glu Val Glu Val Cys Cys Ser Asn Leu Asn Tyr Leu Lys Tyr
            500                 505                 510

Gly Met Leu Thr Arg Lys Asn Ser Lys Ser Ala Met Gln Ala Gly Gly
        515                 520                 525

Asn Ser Ser Gln Ala Asp Ala Lys Thr Glu Gln Val Glu Gln Ser Met
530                 535                 540

Phe Leu Gln Gly Glu Arg Thr Asp Glu Lys Glu Ile Pro Thr Asp Gln
545                 550                 555                 560

Asn Val Val Tyr Arg Gly Ser Trp Tyr Gly His Ile Ala Asn Gly Thr
                565                 570                 575

Ser Trp Ser Gly Asn Ala Ser Asp Lys Glu Gly Gly Asn Arg Ala Glu
            580                 585                 590

Phe Thr Val Asn Phe Ala Asp Lys Lys Ile Thr Gly Lys Leu Thr Ala
        595                 600                 605

Glu Asn Arg Gln Ala Gln Thr Phe Thr Ile Glu Gly Met Ile Gln Gly
```

```
            610                 615                 620
Asn Gly Phe Glu Gly Thr Ala Lys Thr Ala Glu Ser Gly Phe Asp Leu
625                 630                 635                 640

Asp Gln Lys Asn Thr Thr Arg Thr Pro Lys Ala Tyr Ile Thr Asp Ala
                645                 650                 655

Lys Val Lys Gly Gly Phe Tyr Gly Pro Lys Ala Glu Glu Leu Gly Gly
                660                 665                 670

Trp Phe Ala Tyr Pro Gly Asp Lys Gln Thr Glu Lys Ala Thr Ala Thr
                675                 680                 685

Ser Ser Asp Gly Asn Ser Ala Ser Ser Ala Thr Val Val Phe Gly Ala
                690                 695                 700

Lys Arg Gln Gln Pro Val Gln
705                 710

<210> SEQ ID NO 6
<211> LENGTH: 599
<212> TYPE: PRT
<213> ORGANISM: Neisseria meningitidis

<400> SEQUENCE: 6

Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser
                20                  25                  30

Val Glu Thr Val Gln Asp Met His Ser Lys Pro Lys Tyr Glu Asp Glu
            35                  40                  45

Lys Ser Gln Pro Glu Ser Gln Gln Asp Val Ser Glu Asn Ser Gly Ala
        50                  55                  60

Ala Tyr Gly Phe Ala Val Lys Leu Pro Arg Arg Asn Ala His Phe Asn
65                  70                  75                  80

Pro Lys Tyr Lys Glu Lys His Lys Pro Leu Gly Ser Met Asp Trp Lys
                85                  90                  95

Lys Leu Gln Arg Gly Glu Pro Asn Ser Phe Ser Glu Arg Asp Glu Leu
                100                 105                 110

Glu Lys Lys Arg Gly Ser Ser Glu Leu Ile Glu Ser Lys Trp Glu Asp
            115                 120                 125

Gly Gln Ser Arg Val Val Gly Tyr Thr Asn Phe Thr Tyr Val Arg Ser
130                 135                 140

Gly Tyr Val Tyr Leu Asn Lys Asn Asn Ile Asp Ile Lys Asn Asn Ile
145                 150                 155                 160

Val Leu Phe Gly Pro Asp Gly Tyr Leu Tyr Lys Gly Lys Glu Pro
                165                 170                 175

Ser Lys Glu Leu Pro Ser Glu Lys Ile Thr Tyr Lys Gly Thr Trp Asp
                180                 185                 190

Tyr Val Thr Asp Ala Met Glu Lys Gln Arg Phe Glu Gly Leu Gly Ser
                195                 200                 205

Ala Ala Gly Gly Asp Lys Ser Gly Ala Leu Ser Ala Leu Glu Glu Gly
                210                 215                 220

Val Leu Arg Asn Gln Ala Glu Ala Ser Ser Gly His Thr Asp Phe Gly
225                 230                 235                 240

Met Thr Ser Glu Phe Glu Val Asp Phe Ser Asp Lys Thr Ile Lys Gly
                245                 250                 255

Thr Leu Tyr Arg Asn Asn Arg Ile Thr Gln Asn Asn Ser Glu Asn Lys
                260                 265                 270
```

```
Gln Ile Lys Thr Thr Arg Tyr Thr Ile Gln Ala Thr Leu His Gly Asn
            275                 280                 285

Arg Phe Lys Gly Lys Ala Leu Ala Ala Asp Lys Gly Ala Thr Asn Gly
290                 295                 300

Ser His Pro Phe Ile Ser Asp Ser Asp Ser Leu Glu Gly Gly Phe Tyr
305                 310                 315                 320

Gly Pro Lys Gly Glu Glu Leu Ala Gly Lys Phe Leu Ser Asn Asp Asn
                325                 330                 335

Lys Val Ala Ala Val Phe Gly Ala Lys Gln Lys Asp Lys Lys Asp Gly
            340                 345                 350

Glu Asn Ala Ala Gly Pro Ala Thr Glu Thr Val Ile Asp Ala Tyr Arg
            355                 360                 365

Ile Thr Gly Glu Glu Phe Lys Lys Glu Gln Ile Asp Ser Phe Gly Asp
370                 375                 380

Val Lys Lys Leu Leu Val Asp Gly Val Glu Leu Ser Leu Leu Pro Ser
385                 390                 395                 400

Glu Gly Asn Lys Ala Ala Phe Gln His Glu Ile Glu Gln Asn Gly Val
                405                 410                 415

Lys Ala Thr Val Cys Cys Ser Asn Leu Asp Tyr Met Ser Phe Gly Lys
            420                 425                 430

Leu Ser Lys Glu Asn Lys Asp Asp Met Phe Leu Gln Gly Val Arg Thr
            435                 440                 445

Pro Val Ser Asp Val Ala Ala Arg Thr Glu Ala Asn Ala Lys Tyr Arg
            450                 455                 460

Gly Thr Trp Tyr Gly Tyr Ile Ala Asn Gly Thr Ser Trp Ser Gly Glu
465                 470                 475                 480

Ala Ser Asn Gln Glu Gly Gly Asn Arg Ala Glu Phe Asp Val Asp Phe
                485                 490                 495

Ser Thr Lys Lys Ile Ser Gly Thr Leu Thr Ala Lys Asp Arg Thr Ser
            500                 505                 510

Pro Ala Phe Thr Ile Thr Ala Met Ile Lys Asp Asn Gly Phe Ser Gly
            515                 520                 525

Val Ala Lys Thr Gly Glu Asn Gly Phe Ala Leu Asp Pro Gln Asn Thr
530                 535                 540

Gly Asn Ser His Tyr Thr His Ile Glu Ala Thr Val Ser Gly Gly Phe
545                 550                 555                 560

Tyr Gly Lys Asn Ala Ile Glu Met Gly Gly Ser Phe Ser Phe Pro Gly
                565                 570                 575

Asn Ala Pro Glu Gly Lys Gln Glu Lys Ala Ser Val Val Phe Gly Ala
            580                 585                 590

Lys Arg Gln Gln Leu Val Gln
        595

<210> SEQ ID NO 7
<211> LENGTH: 824
<212> TYPE: PRT
<213> ORGANISM: Neisseria meningitidis

<400> SEQUENCE: 7

Gly Gly Gly Gly Gly Thr Ser Ala Pro Asp Phe Asn Ala Gly Gly
1               5                   10                  15

Thr Gly Ile Gly Ser Asn Ser Arg Ala Thr Thr Ala Lys Ser Ala Ala
            20                  25                  30

Val Ser Tyr Ala Gly Ile Lys Asn Glu Met Cys Lys Asp Arg Ser Met
            35                  40                  45
```

-continued

```
Leu Cys Ala Gly Arg Asp Asp Val Ala Val Thr Asp Arg Asp Ala Lys
    50                  55                  60

Ile Asn Ala Pro Pro Pro Asn Leu His Thr Gly Asp Phe Pro Asn Pro
65                  70                  75                  80

Asn Asp Ala Tyr Lys Asn Leu Ile Asn Leu Lys Pro Ala Ile Glu Ala
                85                  90                  95

Gly Tyr Thr Gly Arg Gly Val Glu Val Gly Ile Val Asp Thr Gly Glu
                100                 105                 110

Ser Val Gly Ser Ile Ser Phe Pro Glu Leu Tyr Gly Arg Lys Glu His
                115                 120                 125

Gly Tyr Asn Glu Asn Tyr Lys Asn Tyr Thr Ala Tyr Met Arg Lys Glu
            130                 135                 140

Ala Pro Glu Asp Gly Gly Lys Asp Ile Glu Ala Ser Phe Asp Asp
145                 150                 155                 160

Glu Ala Val Ile Glu Thr Glu Ala Lys Pro Thr Asp Ile Arg His Val
                165                 170                 175

Lys Glu Ile Gly His Ile Asp Leu Val Ser His Ile Ile Gly Gly Arg
                180                 185                 190

Ser Val Asp Gly Arg Pro Ala Gly Gly Ile Ala Pro Asp Ala Thr Leu
            195                 200                 205

His Ile Met Asn Thr Asn Asp Glu Thr Lys Asn Glu Met Met Val Ala
210                 215                 220

Ala Ile Arg Asn Ala Trp Val Lys Leu Gly Glu Arg Gly Val Arg Ile
225                 230                 235                 240

Val Asn Asn Ser Phe Gly Thr Thr Ser Arg Ala Gly Thr Ala Asp Leu
                245                 250                 255

Phe Gln Ile Ala Asn Ser Glu Glu Gln Tyr Arg Gln Ala Leu Leu Asp
            260                 265                 270

Tyr Ser Gly Gly Asp Lys Thr Asp Glu Gly Ile Arg Leu Met Gln Gln
            275                 280                 285

Ser Asp Tyr Gly Asn Leu Ser Tyr His Ile Arg Asn Lys Asn Met Leu
290                 295                 300

Phe Ile Phe Ser Thr Gly Asn Asp Ala Gln Ala Gln Pro Asn Thr Tyr
305                 310                 315                 320

Ala Leu Leu Pro Phe Tyr Glu Lys Asp Ala Gln Lys Gly Ile Ile Thr
                325                 330                 335

Val Ala Gly Val Asp Arg Ser Gly Glu Lys Phe Lys Arg Glu Met Tyr
            340                 345                 350

Gly Glu Pro Gly Thr Glu Pro Leu Glu Tyr Gly Ser Asn His Cys Gly
            355                 360                 365

Ile Thr Ala Met Trp Cys Leu Ser Ala Pro Tyr Glu Ala Ser Val Arg
        370                 375                 380

Phe Thr Arg Thr Asn Pro Ile Gln Ile Ala Gly Thr Ala Phe Ser Ala
385                 390                 395                 400

Pro Ile Val Thr Gly Thr Ala Ala Leu Leu Leu Gln Lys Tyr Pro Trp
                405                 410                 415

Met Ser Asn Asp Asn Leu Arg Thr Thr Leu Leu Thr Thr Ala Gln Asp
                420                 425                 430

Ile Gly Ala Val Gly Val Asp Ser Lys Phe Gly Trp Gly Leu Leu Asp
        435                 440                 445

Ala Gly Lys Ala Met Asn Gly Pro Ala Ser Phe Pro Phe Gly Asp Phe
450                 455                 460
```

```
Thr Ala Asp Thr Lys Gly Thr Ser Asp Ile Ala Tyr Ser Phe Arg Asn
465                 470                 475                 480

Asp Ile Ser Gly Thr Gly Gly Leu Ile Lys Lys Gly Gly Ser Gln Leu
            485                 490                 495

Gln Leu His Gly Asn Asn Thr Tyr Thr Gly Lys Thr Ile Ile Glu Gly
                500                 505                 510

Gly Ser Leu Val Leu Tyr Gly Asn Asn Lys Ser Asp Met Arg Val Glu
            515                 520                 525

Thr Lys Gly Ala Leu Ile Tyr Asn Gly Ala Ala Ser Gly Gly Ser Leu
        530                 535                 540

Asn Ser Asp Gly Ile Val Tyr Leu Ala Asp Thr Asp Gln Ser Gly Ala
545                 550                 555                 560

Asn Glu Thr Val His Ile Lys Gly Ser Leu Gln Leu Asp Gly Lys Gly
                565                 570                 575

Thr Leu Tyr Thr Arg Leu Gly Lys Leu Leu Lys Val Asp Gly Thr Ala
            580                 585                 590

Ile Ile Gly Gly Lys Leu Tyr Met Ser Ala Arg Gly Lys Gly Ala Gly
            595                 600                 605

Tyr Leu Asn Ser Thr Gly Arg Arg Val Pro Phe Leu Ser Ala Ala Lys
        610                 615                 620

Ile Gly Gln Asp Tyr Ser Phe Phe Thr Asn Ile Glu Thr Asp Gly Gly
625                 630                 635                 640

Leu Leu Ala Ser Leu Asp Ser Val Glu Lys Thr Ala Gly Ser Glu Gly
                645                 650                 655

Asp Thr Leu Ser Tyr Tyr Val Arg Arg Gly Asn Ala Ala Arg Thr Ala
            660                 665                 670

Ser Ala Ala His Ser Ala Pro Ala Gly Leu Lys His Ala Val Glu
        675                 680                 685

Gln Gly Gly Ser Asn Leu Glu Asn Leu Met Val Glu Leu Asp Ala Ser
            690                 695                 700

Glu Ser Ser Ala Thr Pro Glu Thr Val Glu Thr Ala Ala Ala Asp Arg
705                 710                 715                 720

Thr Asp Met Pro Gly Ile Arg Pro Tyr Gly Ala Thr Phe Arg Ala Ala
                725                 730                 735

Ala Ala Val Gln His Ala Asn Ala Ala Asp Gly Val Arg Ile Phe Asn
            740                 745                 750

Ser Leu Ala Ala Thr Val Tyr Ala Asp Ser Thr Ala Ala His Ala Asp
        755                 760                 765

Met Gln Gly Arg Arg Leu Lys Ala Val Ser Asp Gly Leu Asp His Asn
        770                 775                 780

Gly Thr Gly Leu Arg Val Ile Ala Gln Thr Gln Gln Asp Gly Gly Thr
785                 790                 795                 800

Trp Glu Gln Gly Gly Val Glu Gly Lys Met Arg Gly Ser Thr Gln Thr
                805                 810                 815

Val Gly Ile Ala Ala Lys Thr Gly
            820

<210> SEQ ID NO 8
<211> LENGTH: 1557
<212> TYPE: PRT
<213> ORGANISM: Neisseria meningitidis

<400> SEQUENCE: 8

Ala Leu Val Arg Asp Asp Val Asp Tyr Gln Ile Phe Arg Asp Phe Ala
1               5                   10                  15
```

```
Glu Asn Lys Gly Lys Phe Phe Val Gly Ala Thr Asp Leu Ser Val Lys
             20                  25                  30

Asn Lys Gln Gly Gln Asn Ile Gly Asn Ala Leu Ser Asn Val Pro Met
         35                  40                  45

Ile Asp Phe Ser Val Ala Asp Val Asn Arg Arg Thr Leu Thr Val Ile
 50                  55                  60

Asp Pro Gln Tyr Ala Val Ser Val Lys His Val Lys Gly Asp Glu Ile
 65                  70                  75                  80

Ser Tyr Tyr Gly His His Asn Gly His Leu Asp Val Ser Asn Asp Glu
                 85                  90                  95

Asn Glu Tyr Arg Ser Val Ala Gln Asn Asp Tyr Glu Pro Asn Lys Asn
             100                 105                 110

Trp His His Gly Asn Gln Gly Arg Leu Glu Asp Tyr Asn Met Ala Arg
         115                 120                 125

Leu Asn Lys Phe Val Thr Glu Val Ala Pro Ile Ala Pro Thr Ser Ala
130                 135                 140

Gly Gly Gly Val Glu Thr Tyr Lys Asp Lys Asn Arg Phe Ser Glu Phe
145                 150                 155                 160

Val Arg Val Gly Ala Gly Thr Gln Phe Glu Tyr Asn Ser Arg Tyr Asn
                 165                 170                 175

Met Thr Glu Leu Ser Arg Ala Tyr Arg Tyr Ala Ile Ala Gly Thr Pro
             180                 185                 190

Tyr Gln Asp Val Asn Val Thr Ser Asn Leu Asn Gln Glu Gly Leu Ile
         195                 200                 205

Gly Phe Gly Asp Asn Ser Lys His His Ser Pro Glu Lys Leu Lys Glu
210                 215                 220

Val Leu Ser Gln Asn Ala Leu Thr Asn Tyr Ala Val Leu Gly Asp Val
225                 230                 235                 240

Gly Ser Pro Leu Phe Ala Tyr Asp Lys Gln Glu Lys Arg Trp Val Phe
                 245                 250                 255

Leu Gly Ala Tyr Asp Tyr Trp Ala Gly Tyr Gln Lys Asn Ser Trp Gln
             260                 265                 270

Glu Trp Asn Ile Tyr Lys Lys Glu Phe Ala Asp Glu Ile Lys Gln Arg
         275                 280                 285

Asp Asn Ala Gly Thr Ile Lys Gly Asn Gly Glu His His Trp Lys Thr
290                 295                 300

Thr Gly Thr Asn Ser His Ile Gly Ser Thr Ala Val Arg Leu Ala Asn
305                 310                 315                 320

Asn Glu Arg Asp Ala Asn Asn Gly Gln Asn Val Thr Phe Glu Asn Asn
                 325                 330                 335

Gly Thr Leu Val Leu Asp Gln Asn Ile Asn Gln Gly Ala Gly Gly Leu
             340                 345                 350

Phe Phe Lys Gly Asp Tyr Thr Val Lys Gly Ile Asn Asn Asp Ile Thr
         355                 360                 365

Trp Leu Gly Ala Gly Ile Asp Val Ala Asp Gly Lys Val Val Trp
370                 375                 380

Gln Val Lys Asn Pro Asn Gly Asp Arg Leu Ala Lys Ile Gly Lys Gly
385                 390                 395                 400

Thr Leu Glu Ile Asn Gly Thr Val Asn Gln Gly Gln Leu Lys Val
                 405                 410                 415

Gly Asp Gly Thr Val Ile Leu Asn Gln Gln Ala Asp Ala Asp Lys Lys
             420                 425                 430
```

-continued

Val Gln Ala Phe Ser Gln Val Gly Ile Val Ser Gly Arg Gly Thr Leu
            435                 440                 445

Val Leu Asn Ser Ser Asn Gln Ile Asn Pro Asp Asn Leu Tyr Phe Gly
450                 455                 460

Phe Arg Gly Gly Arg Leu Asp Ala Asn Gly Asn Asp Leu Thr Phe Glu
465                 470                 475                 480

His Ile Arg Asn Val Asp Glu Gly Ala Arg Ile Val Asn His Asn Thr
                485                 490                 495

Gly His Ala Ser Thr Ile Thr Leu Thr Gly Lys Ser Leu Ile Thr Asp
                500                 505                 510

Pro Lys Thr Ile Ser Ile His Tyr Ile Gln Asn Asn Asp Asp Asp Asp
            515                 520                 525

Ala Gly Tyr Tyr Tyr Tyr Arg Pro Arg Lys Pro Ile Pro Gln Gly Lys
            530                 535                 540

Asp Leu Tyr Phe Lys Asn Tyr Arg Tyr Tyr Ala Leu Lys Ser Gly Gly
545                 550                 555                 560

Ser Val Asn Ala Pro Met Pro Glu Asn Gly Gln Thr Glu Asn Asn Asp
                565                 570                 575

Trp Ile Leu Met Gly Ser Thr Gln Glu Glu Ala Lys Lys Asn Ala Met
            580                 585                 590

Asn His Lys Asn Asn Gln Arg Ile Ser Gly Phe Ser Gly Phe Phe Gly
            595                 600                 605

Glu Glu Asn Gly Lys Gly His Asn Gly Ala Leu Asn Leu Asn Phe Asn
            610                 615                 620

Gly Lys Ser Ala Gln Asn Arg Phe Leu Leu Thr Gly Gly Thr Asn Leu
625                 630                 635                 640

Asn Gly Lys Ile Ser Val Thr Gln Gly Asn Val Leu Leu Ser Gly Arg
                645                 650                 655

Pro Thr Pro His Ala Arg Asp Phe Val Asn Lys Ser Ser Ala Arg Lys
                660                 665                 670

Asp Ala His Phe Ser Lys Asn Asn Glu Val Val Phe Glu Asp Asp Trp
            675                 680                 685

Ile Asn Arg Thr Phe Lys Ala Thr Glu Ile Ala Val Asn Gln Ser Ala
            690                 695                 700

Ser Phe Ser Ser Gly Arg Asn Val Ser Asp Ile Thr Ala Asn Ile Thr
705                 710                 715                 720

Ala Thr Asp Asn Ala Lys Val Asn Leu Gly Tyr Lys Asn Gly Asp Glu
                725                 730                 735

Val Cys Val Arg Ser Asp Tyr Thr Gly Tyr Val Thr Cys Asn Thr Gly
            740                 745                 750

Asn Leu Ser Asp Lys Ala Leu Asn Ser Phe Gly Ala Thr Gln Ile Asn
            755                 760                 765

Gly Asn Val Asn Leu Asn Gln Asn Ala Ala Leu Val Leu Gly Lys Ala
            770                 775                 780

Ala Leu Trp Gly Gln Ile Gln Gly Gln Gly Asn Ser Arg Val Ser Leu
785                 790                 795                 800

Asn Gln His Ser Lys Trp His Leu Thr Gly Asp Ser Gln Val His Asn
            805                 810                 815

Leu Ser Leu Ala Asp Ser His Ile His Leu Asn Asn Ala Ser Asp Ala
            820                 825                 830

Gln Ser Ala Asn Lys Tyr His Thr Leu Lys Ile Asn His Leu Ser Gly
            835                 840                 845

Asn Gly His Phe His Tyr Leu Thr His Leu Ala Lys Asn Leu Gly Asp

```
                850                 855                 860
Lys Val Leu Val Lys Glu Ser Ala Ser Gly His Tyr Gln Leu His Val
865                 870                 875                 880

Gln Asp Lys Thr Gly Glu Pro Asn Gln Glu Gly Leu Asn Leu Phe Asp
                885                 890                 895

Ala Ser Ser Val Gln Asp Arg Ser Arg Leu Ser Val Ser Leu Ala Asn
                900                 905                 910

Asn His Val Asp Leu Gly Ala Leu Arg Tyr Thr Ile Lys Thr Glu Asn
            915                 920                 925

Gly Ile Thr Arg Leu Tyr Asn Pro Tyr Ala Glu Asn Arg Arg Arg Val
        930                 935                 940

Lys Pro Ala Pro Ser Pro Ala Thr Asn Thr Ala Ser Gln Ala Gln Lys
945                 950                 955                 960

Ala Thr Gln Thr Asp Gly Ala Gln Ile Ala Lys Pro Gln Asn Ile Val
                965                 970                 975

Val Ala Pro Pro Ser Pro Gln Ala Asn Gln Ala Glu Glu Ala Lys Arg
                980                 985                 990

Gln Gln Ala Lys Ala Glu Gln Val Lys Arg Gln Gln Ala Glu Ala Glu
            995                 1000                1005

Arg Lys Ser Ala Glu Leu Ala Lys Gln Lys Ala Glu Ala Glu Arg Glu
        1010                1015                1020

Ala Arg Glu Leu Ala Thr Arg Gln Lys Ala Glu Gln Glu Arg Ser Ser
1025                1030                1035                1040

Ala Glu Leu Ala Arg Arg His Glu Lys Glu Arg Glu Ala Ala Glu Leu
                1045                1050                1055

Ser Ala Lys Gln Lys Val Glu Ala Glu Arg Glu Ala Gln Ala Leu Ala
                1060                1065                1070

Val Arg Arg Lys Ala Glu Ala Glu Ala Lys Arg Gln Ala Ala Glu
            1075                1080                1085

Leu Ala Arg Arg His Glu Lys Glu Arg Glu Ala Ala Glu Leu Ser Ala
        1090                1095                1100

Lys Gln Arg Val Gly Glu Glu Arg Gln Thr Ala Gln Ser Gln
1105                1110                1115                1120

Pro Gln Arg Arg Lys Arg Arg Ala Ala Pro Gln Asp Tyr Met Ala Ala
                1125                1130                1135

Ser Gln Asp Arg Pro Lys Arg Arg Gly His Arg Ser Val Gln Gln Asn
                1140                1145                1150

Asn Val Glu Ile Ala Gln Ala Gln Ala Glu Leu Ala Arg Arg Gln Gln
            1155                1160                1165

Glu Glu Arg Lys Ala Ala Glu Leu Leu Ala Lys Gln Arg Ala Glu Ala
        1170                1175                1180

Glu Arg Glu Ala Gln Ala Leu Ala Arg Arg Lys Ala Glu Ala Glu
1185                1190                1195                1200

Glu Ala Lys Arg Gln Ala Ala Glu Leu Ala His Arg Gln Glu Ala Glu
                1205                1210                1215

Arg Lys Ala Ala Glu Leu Ser Ala Asn Gln Lys Ala Ala Glu Ala
                1220                1225                1230

Gln Ala Leu Ala Ala Arg Gln Gln Lys Ala Leu Ala Arg Gln Gln Glu
            1235                1240                1245

Glu Ala Arg Lys Ala Ala Glu Leu Ala Val Lys Gln Lys Ala Glu Thr
        1250                1255                1260

Glu Arg Lys Thr Ala Glu Leu Ala Lys Gln Arg Ala Ala Ala Glu Ala
1265                1270                1275                1280
```

Ala Lys Arg Gln Gln Glu Ala Arg Gln Thr Ala Glu Leu Ala Arg Arg
            1285                1290                1295

Gln Glu Ala Glu Arg Gln Ala Ala Glu Leu Ser Ala Lys Gln Lys Ala
            1300                1305                1310

Glu Thr Asp Arg Glu Ala Ala Glu Ser Ala Lys Arg Lys Ala Glu Glu
            1315                1320                1325

Glu Glu His Arg Gln Ala Ala Gln Ser Gln Pro Gln Arg Arg Lys Arg
            1330                1335                1340

Arg Ala Ala Pro Gln Asp Tyr Met Ala Ala Ser Gln Asn Arg Pro Lys
1345                1350                1355                1360

Arg Arg Gly Arg Arg Ser Thr Leu Pro Ala Pro Pro Ser Pro Ser Phe
            1365                1370                1375

Asp Ser Ser Ala Tyr Ala Ala Pro Arg Ala Leu His Asn Pro Asp Trp
            1380                1385                1390

Tyr Glu Asn Asp Tyr Glu Glu Ile Pro Leu Asp Ala Leu Glu Asp Glu
            1395                1400                1405

Asn Val Ser Glu Ser Val Asp Thr Ser Asp Lys Gln Pro Gln Asp Asn
            1410                1415                1420

Thr Glu Leu His Glu Lys Tyr Glu Asn Asp Tyr Glu Glu Ile Pro Leu
1425                1430                1435                1440

Asp Ala Leu Glu Asp Glu Asp Val Ser Glu Ser Val Asp Thr Ser Asp
            1445                1450                1455

Lys Gln Pro Gln Asp Asn Thr Glu Leu His Glu Lys Val Glu Thr Val
            1460                1465                1470

Ser Leu Gln Pro Arg Ala Ala Gln Pro Arg Ala Gln Ala Ala Thr Gln
            1475                1480                1485

Leu Gln Ala Gln Ala Ala Gln Ala Asp Ala Val Ser Thr Asn Thr
            1490                1495                1500

Asn Ser Ala Leu Ser Asp Ala Met Ala Ser Thr Gln Ser Ile Leu Leu
1505                1510                1515                1520

Asp Thr Gly Ala Ser Leu Thr Arg His Ile Ala Gln Lys Ser Arg Ala
            1525                1530                1535

Asp Ala Glu Lys Asn Ser Val Trp Met Ser Thr Gly Tyr Gly Arg
            1540                1545                1550

Asp Tyr Ala Ser Ala
        1555

<210> SEQ ID NO 9
<211> LENGTH: 978
<212> TYPE: PRT
<213> ORGANISM: Neisseria meningitidis

<400> SEQUENCE: 9

Ala Leu Val Arg Asp Asp Val Asp Tyr Gln Ile Phe Arg Asp Phe Ala
1               5                   10                  15

Glu Asn Lys Gly Lys Phe Phe Val Gly Ala Thr Asp Leu Ser Val Lys
            20                  25                  30

Asn Lys Gln Gly Gln Asn Ile Gly Asn Ala Leu Ser Asn Val Pro Met
        35                  40                  45

Ile Asp Phe Ser Val Ala Asp Val Asn Arg Arg Thr Leu Thr Val Ile
    50                  55                  60

Asp Pro Gln Tyr Ala Val Ser Val Lys His Val Lys Gly Asp Glu Ile
65                  70                  75                  80

Ser Tyr Tyr Gly His His Asn Gly His Leu Asp Val Ser Asn Asp Glu

-continued

```
                85                  90                  95
Asn Glu Tyr Arg Ser Val Ala Gln Asn Asp Tyr Glu Pro Asn Lys Asn
                100                 105                 110
Trp His His Gly Asn Gln Gly Arg Leu Glu Asp Tyr Asn Met Ala Arg
            115                 120                 125
Leu Asn Lys Phe Val Thr Glu Val Ala Pro Ile Ala Pro Thr Ser Ala
        130                 135                 140
Gly Gly Val Glu Thr Tyr Lys Asp Lys Asn Arg Phe Ser Glu Phe
145                 150                 155                 160
Val Arg Val Gly Ala Gly Thr Gln Phe Glu Tyr Asn Ser Arg Tyr Asn
                165                 170                 175
Met Thr Glu Leu Ser Arg Ala Tyr Arg Tyr Ala Ile Ala Gly Thr Pro
            180                 185                 190
Tyr Gln Asp Val Asn Val Thr Ser Asn Leu Asn Gln Glu Gly Leu Ile
        195                 200                 205
Gly Phe Gly Asp Asn Ser Lys His His Ser Pro Glu Lys Leu Lys Glu
    210                 215                 220
Val Leu Ser Gln Asn Ala Leu Thr Asn Tyr Ala Val Leu Gly Asp Val
225                 230                 235                 240
Gly Ser Pro Leu Phe Ala Tyr Asp Lys Gln Glu Lys Arg Trp Val Phe
                245                 250                 255
Leu Gly Ala Tyr Asp Tyr Trp Ala Gly Tyr Gln Lys Asn Ser Trp Gln
            260                 265                 270
Glu Trp Asn Ile Tyr Lys Lys Glu Phe Ala Asp Glu Ile Lys Gln Arg
        275                 280                 285
Asp Asn Ala Gly Thr Ile Lys Gly Asn Gly Glu His His Trp Lys Thr
    290                 295                 300
Thr Gly Thr Asn Ser His Ile Gly Ser Thr Ala Val Arg Leu Ala Asn
305                 310                 315                 320
Asn Glu Arg Asp Ala Asn Asn Gly Gln Asn Val Thr Phe Glu Asn Asn
                325                 330                 335
Gly Thr Leu Val Leu Asp Gln Asn Ile Asn Gln Gly Ala Gly Gly Leu
            340                 345                 350
Phe Phe Lys Gly Asp Tyr Thr Val Lys Gly Ile Asn Asn Asp Ile Thr
        355                 360                 365
Trp Leu Gly Ala Gly Ile Asp Val Ala Asp Gly Lys Lys Val Val Trp
    370                 375                 380
Gln Val Lys Asn Pro Asn Gly Asp Arg Leu Ala Lys Ile Gly Lys Gly
385                 390                 395                 400
Thr Leu Glu Ile Asn Gly Thr Gly Val Asn Gln Gly Gln Leu Lys Val
                405                 410                 415
Gly Asp Gly Thr Val Ile Leu Asn Gln Gln Ala Asp Ala Asp Lys Lys
            420                 425                 430
Val Gln Ala Phe Ser Gln Val Gly Ile Val Ser Gly Arg Gly Thr Leu
        435                 440                 445
Val Leu Asn Ser Ser Asn Gln Ile Asn Pro Asp Asn Leu Tyr Phe Gly
    450                 455                 460
Phe Arg Gly Gly Arg Leu Asp Ala Asn Gly Asn Asp Leu Thr Phe Glu
465                 470                 475                 480
His Ile Arg Asn Val Asp Glu Gly Ala Arg Ile Val Asn His Asn Thr
                485                 490                 495
Gly His Ala Ser Thr Ile Thr Leu Thr Gly Lys Ser Leu Ile Thr Asp
            500                 505                 510
```

```
Pro Lys Thr Ile Ser Ile His Tyr Ile Gln Asn Asn Asp Asp Asp
        515                 520                 525
Ala Gly Tyr Tyr Tyr Arg Pro Arg Lys Pro Ile Pro Gln Gly Lys
    530                 535                 540
Asp Leu Tyr Phe Lys Asn Tyr Arg Tyr Ala Leu Lys Ser Gly Gly
545                 550                 555                 560
Ser Val Asn Ala Pro Met Pro Glu Asn Gly Gln Thr Glu Asn Asp
                565                 570                 575
Trp Ile Leu Met Gly Ser Thr Gln Glu Ala Lys Lys Asn Ala Met
                580                 585                 590
Asn His Lys Asn Asn Gln Arg Ile Ser Gly Phe Ser Gly Phe Gly
        595                 600                 605
Glu Glu Asn Gly Lys Gly His Asn Gly Ala Leu Asn Leu Asn Phe Asn
        610                 615                 620
Gly Lys Ser Ala Gln Asn Arg Phe Leu Leu Thr Gly Gly Thr Asn Leu
625                 630                 635                 640
Asn Gly Lys Ile Ser Val Thr Gln Gly Asn Val Leu Leu Ser Gly Arg
                645                 650                 655
Pro Thr Pro His Ala Arg Asp Phe Val Asn Lys Ser Ser Ala Arg Lys
                660                 665                 670
Asp Ala His Phe Ser Lys Asn Asn Glu Val Val Phe Glu Asp Asp Trp
            675                 680                 685
Ile Asn Arg Thr Phe Lys Ala Thr Glu Ile Ala Val Asn Gln Ser Ala
            690                 695                 700
Ser Phe Ser Ser Gly Arg Asn Val Ser Asp Ile Thr Ala Asn Ile Thr
705                 710                 715                 720
Ala Thr Asp Asn Ala Lys Val Asn Leu Gly Tyr Lys Asn Gly Asp Glu
                725                 730                 735
Val Cys Val Arg Ser Asp Tyr Thr Gly Tyr Val Thr Cys Asn Thr Gly
                740                 745                 750
Asn Leu Ser Asp Lys Ala Leu Asn Ser Phe Gly Ala Thr Gln Ile Asn
            755                 760                 765
Gly Asn Val Asn Leu Asn Gln Asn Ala Ala Leu Val Leu Gly Lys Ala
        770                 775                 780
Ala Leu Trp Gly Gln Ile Gln Gly Gln Gly Asn Ser Arg Val Ser Leu
785                 790                 795                 800
Asn Gln His Ser Lys Trp His Leu Thr Gly Asp Ser Gln Val His Asn
            805                 810                 815
Leu Ser Leu Ala Asp Ser His Ile His Leu Asn Asn Ala Ser Asp Ala
                820                 825                 830
Gln Ser Ala Asn Lys Tyr His Thr Leu Lys Ile Asn His Leu Ser Gly
            835                 840                 845
Asn Gly His Phe His Tyr Leu Thr His Leu Ala Lys Asn Leu Gly Asp
        850                 855                 860
Lys Val Leu Val Lys Glu Ser Ala Ser Gly His Tyr Gln Leu His Val
865                 870                 875                 880
Gln Asp Lys Thr Gly Glu Pro Asn Gln Glu Gly Leu Asn Leu Phe Asp
                885                 890                 895
Ala Ser Ser Val Gln Asp Arg Ser Arg Leu Ser Val Ser Leu Ala Asn
            900                 905                 910
Asn His Val Asp Leu Gly Ala Leu Arg Tyr Thr Ile Lys Thr Glu Asn
        915                 920                 925
```

```
Gly Ile Thr Arg Leu Tyr Asn Pro Tyr Ala Glu Asn Arg Arg Val
            930                 935                 940

Lys Pro Ala Pro Ser Pro Ala Thr Asn Thr Ala Ser Gln Ala Gln Lys
945                 950                 955                 960

Ala Thr Gln Thr Asp Gly Ala Gln Ile Ala Lys Pro Gln Asn Ile Val
                965                 970                 975

Val Ala

<210> SEQ ID NO 10
<211> LENGTH: 1066
<212> TYPE: PRT
<213> ORGANISM: Neisseria meningitidis

<400> SEQUENCE: 10

Ala Leu Val Arg Asp Asp Val Asp Tyr Gln Ile Phe Arg Asp Phe Ala
1               5                   10                  15

Glu Asn Lys Gly Lys Phe Phe Val Gly Ala Thr Asp Leu Ser Val Lys
                20                  25                  30

Asn Lys Gln Gly Gln Asn Ile Gly Asn Ala Leu Ser Asn Val Pro Met
            35                  40                  45

Ile Asp Phe Ser Val Ala Asp Val Asn Arg Arg Thr Leu Thr Val Ile
50                  55                  60

Asp Pro Gln Tyr Ala Val Ser Val Lys His Val Lys Gly Asp Glu Ile
65                  70                  75                  80

Ser Tyr Tyr Gly His His Asn Gly His Leu Asp Val Ser Asn Asp Glu
                85                  90                  95

Asn Glu Tyr Arg Ser Val Ala Gln Asn Asp Tyr Glu Pro Asn Lys Asn
            100                 105                 110

Trp His His Gly Asn Gln Gly Arg Leu Glu Asp Tyr Asn Met Ala Arg
        115                 120                 125

Leu Asn Lys Phe Val Thr Glu Val Ala Pro Ile Ala Pro Thr Ser Ala
130                 135                 140

Gly Gly Gly Val Glu Thr Tyr Lys Asp Lys Asn Arg Phe Ser Glu Phe
145                 150                 155                 160

Val Arg Val Gly Ala Gly Thr Gln Phe Glu Tyr Asn Ser Arg Tyr Asn
                165                 170                 175

Met Thr Glu Leu Ser Arg Ala Tyr Arg Tyr Ala Ile Ala Gly Thr Pro
            180                 185                 190

Tyr Gln Asp Val Asn Val Thr Ser Asn Leu Asn Gln Glu Gly Leu Ile
        195                 200                 205

Gly Phe Gly Asp Asn Ser Lys His His Ser Pro Glu Lys Leu Lys Glu
210                 215                 220

Val Leu Ser Gln Asn Ala Leu Thr Asn Tyr Ala Val Leu Gly Asp Val
225                 230                 235                 240

Gly Ser Pro Leu Phe Ala Tyr Asp Lys Gln Glu Lys Arg Trp Val Phe
                245                 250                 255

Leu Gly Ala Tyr Asp Tyr Trp Ala Gly Tyr Gln Lys Asn Ser Trp Gln
            260                 265                 270

Glu Trp Asn Ile Tyr Lys Lys Glu Phe Ala Asp Glu Ile Lys Gln Arg
        275                 280                 285

Asp Asn Ala Gly Thr Ile Lys Gly Asn Gly Glu His His Trp Lys Thr
290                 295                 300

Thr Gly Thr Asn Ser His Ile Gly Ser Thr Ala Val Arg Leu Ala Asn
305                 310                 315                 320
```

```
Asn Glu Arg Asp Ala Asn Asn Gly Gln Asn Val Thr Phe Glu Asn Asn
                325                 330                 335

Gly Thr Leu Val Leu Asp Gln Asn Ile Asn Gln Gly Ala Gly Gly Leu
            340                 345                 350

Phe Phe Lys Gly Asp Tyr Thr Val Lys Gly Ile Asn Asn Asp Ile Thr
        355                 360                 365

Trp Leu Gly Ala Gly Ile Asp Val Ala Asp Gly Lys Lys Val Val Trp
    370                 375                 380

Gln Val Lys Asn Pro Asn Gly Asp Arg Leu Ala Lys Ile Gly Lys Gly
385                 390                 395                 400

Thr Leu Glu Ile Asn Gly Thr Gly Val Asn Gln Gly Leu Lys Val
            405                 410                 415

Gly Asp Gly Thr Val Ile Leu Asn Gln Gln Ala Asp Ala Asp Lys Lys
            420                 425                 430

Val Gln Ala Phe Ser Gln Val Gly Ile Val Ser Gly Arg Gly Thr Leu
            435                 440                 445

Val Leu Asn Ser Ser Asn Gln Ile Asn Pro Asp Asn Leu Tyr Phe Gly
        450                 455                 460

Phe Arg Gly Gly Arg Leu Asp Ala Asn Gly Asn Asp Leu Thr Phe Glu
465                 470                 475                 480

His Ile Arg Asn Val Asp Glu Gly Ala Arg Ile Val Asn His Asn Thr
                485                 490                 495

Gly His Ala Ser Thr Ile Thr Leu Thr Gly Lys Ser Leu Ile Thr Asp
            500                 505                 510

Pro Lys Thr Ile Ser Ile His Tyr Ile Gln Asn Asn Asp Asp Asp
        515                 520                 525

Ala Gly Tyr Tyr Tyr Arg Pro Arg Lys Pro Ile Pro Gln Gly Lys
    530                 535                 540

Asp Leu Tyr Phe Lys Asn Tyr Arg Tyr Tyr Ala Leu Lys Ser Gly Gly
545                 550                 555                 560

Ser Val Asn Ala Pro Met Pro Glu Asn Gly Gln Thr Glu Asn Asn Asp
                565                 570                 575

Trp Ile Leu Met Gly Ser Thr Gln Glu Glu Ala Lys Lys Asn Ala Met
            580                 585                 590

Asn His Lys Asn Asn Gln Arg Ile Ser Gly Phe Ser Gly Phe Phe Gly
        595                 600                 605

Glu Glu Asn Gly Lys Gly His Asn Gly Ala Leu Asn Leu Asn Phe Asn
    610                 615                 620

Gly Lys Ser Ala Gln Asn Arg Phe Leu Leu Thr Gly Gly Thr Asn Leu
625                 630                 635                 640

Asn Gly Lys Ile Ser Val Thr Gln Gly Asn Val Leu Leu Ser Gly Arg
                645                 650                 655

Pro Thr Pro His Ala Arg Asp Phe Val Asn Lys Ser Ser Ala Arg Lys
            660                 665                 670

Asp Ala His Phe Ser Lys Asn Asn Glu Val Val Phe Glu Asp Asp Trp
        675                 680                 685

Ile Asn Arg Thr Phe Lys Ala Thr Glu Ile Ala Val Asn Gln Ser Ala
    690                 695                 700

Ser Phe Ser Ser Gly Arg Asn Val Ser Asp Ile Thr Ala Asn Ile Thr
705                 710                 715                 720

Ala Thr Asp Asn Ala Lys Val Asn Leu Gly Tyr Lys Asn Gly Asp Glu
                725                 730                 735

Val Cys Val Arg Ser Asp Tyr Thr Gly Tyr Val Thr Cys Asn Thr Gly
```

-continued

```
                    740                 745                 750
Asn Leu Ser Asp Lys Ala Leu Asn Ser Phe Gly Ala Thr Gln Ile Asn
            755                 760                 765
Gly Asn Val Asn Leu Asn Gln Asn Ala Ala Leu Val Leu Gly Lys Ala
            770                 775                 780
Ala Leu Trp Gly Gln Ile Gln Gly Gln Gly Asn Ser Arg Val Ser Leu
785                 790                 795                 800
Asn Gln His Ser Lys Trp His Leu Thr Gly Asp Ser Gln Val His Asn
            805                 810                 815
Leu Ser Leu Ala Asp Ser His Ile His Leu Asn Asn Ala Ser Asp Ala
            820                 825                 830
Gln Ser Ala Asn Lys Tyr His Thr Leu Lys Ile Asn His Leu Ser Gly
            835                 840                 845
Asn Gly His Phe His Tyr Leu Thr His Leu Ala Lys Asn Leu Gly Asp
850                 855                 860
Lys Val Leu Val Lys Glu Ser Ala Ser Gly His Tyr Gln Leu His Val
865                 870                 875                 880
Gln Asp Lys Thr Gly Glu Pro Asn Gln Glu Gly Leu Asn Leu Phe Asp
            885                 890                 895
Ala Ser Ser Val Gln Asp Arg Ser Arg Leu Ser Val Ser Leu Ala Asn
            900                 905                 910
Asn His Val Asp Leu Gly Ala Leu Arg Tyr Thr Ile Lys Thr Glu Asn
            915                 920                 925
Gly Ile Thr Arg Leu Tyr Asn Pro Tyr Ala Glu Gln Glu Leu Ser Asp
            930                 935                 940
Lys Leu Gly Lys Ala Glu Ala Lys Lys Gln Ala Glu Lys Asp Asn Ala
945                 950                 955                 960
Gln Ser Leu Asp Ala Leu Ile Ala Ala Gly Arg Asp Ala Val Glu Lys
            965                 970                 975
Thr Glu Ser Val Ala Glu Pro Ala Arg Gln Ala Gly Gly Glu Asn Val
            980                 985                 990
Gly Ile Met Gln Ala Glu Glu Lys Lys Arg Val Gln Ala Asp Lys
            995                 1000                1005
Asp Thr Ala Leu Ala Lys Gln Arg Glu Ala Glu Thr Arg Pro Ala Thr
    1010                1015                1020
Thr Ala Phe Pro Arg Ala Arg Arg Ala Arg Arg Asp Leu Pro Gln Leu
1025                1030                1035                1040
Gln Pro Gln Pro Gln Pro Gln Pro Gln Arg Asp Leu Ile Ser Arg Tyr
            1045                1050                1055
Ala Asn Ser Gly Leu Ser Glu Phe Ser Ala
            1060                1065
```

COMPOSITIONS COMPRISING N. MENINGITIDIS PROTEINS

The present invention relates to a composition comprising Neisseria meningitidis a combination of antigens including auto-transporters such as IgA1P, App, AusI or NalP, and TbpB (Transferrin binding protein B) and its use for immunizing or vaccinating a subject against an infection induced by *N. meningitidis*.

*Neisseria meningitidis* is one of the most important causes of bacterial meningitis and septicemia worldwide in both endemic and epidemic forms. The bacteria are classified into serogroups based on the structure of their capsular polysaccharides. Thirteen different serogroups have been identified but only five (A, B, C, W135 and Y) are responsible for the majority of infections, although epidemic meningitis due to meningococcal serogroup X is emerging in the Meningitis Belt of Africa. Two effective quadrivalent polysaccharide-protein conjugate vaccines have been developed and licensed against serogroups A, C, W135 and Y. In contrast to the other capsular polysaccharides, the group B polysaccharide is not an appropriate vaccinal antigen because of structural similarities with polysialic acid chains present in human cells. These properties of the serogroup B polysaccharide have impeded the development of a polysaccharide-based vaccine against group B *Neisseria meningitidis* (MenB) and led to the development of alternative vaccines.

During in vitro culture conditions and in vivo infection *N. meningitidis* releases outer membrane blebs which contain lipooligosaccharide (LOS) and outer membrane proteins (OMPs). These blebs are known as outer membrane vesicles (OMVs). Meningococcal OMV vaccines have been developed and shown to be successful in controlling outbreaks of MenB disease when using OMVs produced from a representative outbreak strain. Several approaches have been carried out to increase the breadth of coverage of OMV vaccines. Despite these developments and the suggestion that a vaccine including six PorA and five FetA variants would potentially provide protection against the majority of global circulating pathogenic strains, the search for a vaccine candidate that is highly conserved and expressed by all disease causing meningococci has continued.

Reverse vaccinology was used by Novartis Vaccines to develop a vaccine for serogroup B meningococcus (MenB), using the genome from the MenB strain MC58. The five most promising antigens on the basis of their ability to induce passive protection or serum bactericidal activity (SBA) were selected to be included in an investigational vaccine. These antigens include factor H binding protein (fHBP, also known as GNA (genome-derived neisserial antigen) 1870 or NMB1870), *Neisseria* Adhesin A (NadA, previously known as GNA1994), *Neisseria* Heparin-Binding Antigen (NHBA, previously known as GNA2132), GNA2091 and GNA1030. To further increase immunogenicity and stability, fHBP was fused with GNA2091, and NHBA with GNA1030. These two fusion proteins mixed together with NadA were proposed as a vaccine composition as described in Giuliani et al., PNAS (2006) 103 (29): 10834. Later on, the vaccinal composition was complemented with OMVs that contain the Porin A (PorA) protein. PorA is an immune-dominant protein that has been demonstrated to elicit antibodies during the course of meningococcal infections.

The final vaccine composition, which has progressed through clinical trials, has been recently licensed and commercialized under the trade name Bexsero®. As stated in the EPAR (European Public Assessment Report) of the EMEA (European Medicine Agency), this vaccine contains three recombinant *N. meningitidis* serogroup B proteins, namely NHBA (*Neisseria* Heparin Binding Antigen) fusion protein, NadA protein and fHBP fusion protein, together with outer membranes vesicles (OMVs) from *N. meningitidis* serogroup B.

One of the recombinant proteins of Bexsero®, fHBP, is also known as lipoprotein 2086 (LP2086) which has been independently discovered by Pfizer using an iterative process of immunisation following differential detergent extraction and protein purification.

fHBP Reference to *N. meningitidis* herein may be understood to refer to any serogroup, or may be understood to refer specifically to the B serogroup.

*N. meningitidis* species is genetically and antigenically highly diverse. Multilocus sequence typing (MLST) was first developed in the late 1990s for the meningococcus. It is a highly reliable and reproducible characterization method, which assesses variation at multiple genetic loci using nucleotide sequencing. More than 6751 sequence types (STs) have been assigned for *N. meningitidis* strains. While meningococcal diversity is extensive, it is highly structured. Studies of variation at housekeeping loci, initially by multilocus enzyme electrophoresis and more recently by MLST, had identified 37 groups of closely related meningococci at the time of writing, accounting for 61% of the meningococcal isolates represented in the PubMLST database. These groups, known as clonal complexes, have become the predominant unit of analysis in meningococcal population biology and epidemiology. A minority of clonal complexes, the so-called hyper-invasive lineages, are responsible for a disproportionate number of cases of disease worldwide and can be over-represented in collections of isolates from diseased patients by as much as two orders of magnitude, relative to their prevalence in asymptomatic carriage (see Table 1 herein after).

TABLE 1

Characteristics of the most important clonal complexes of *Neisseria meningitidis* (data compiled from the PubMLST database Jun. 2, 2009).

| ST-complex | MLEE designation | No. isolates | No. STs | Dominant serogroups (%) | Dominant PorA | Dominant FetA | Disease/carriage ratio | Main origin |
|---|---|---|---|---|---|---|---|---|
| ST-1 complex | Subgroup I/II | 204 | 49 | A (97) | 5-2, 10 | F3-5 | 5.5 | Russia, China |
| ST-5 complex | Subgroup III | 627 | 33 | A (99) | 20, 9 | F3-1 | 19.5 | Africa |
| ST-8 complex | Cluster A4 | 283 | 107 | B (51), C (35) | 5-1, 2-2 | F3-6 | 24.5 | Europe |
| ST-11 complex | ET-37 complex | 1142 | 239 | C (57), W135 (24), B (12) | 5, 2 | F3-6 | 6.6 | Worldwide |
| ST-18 complex | Cluster J1 | 208 | 175 | B (85) | 22, 14 | F3-6 | 5.5 | Czech Republic, Poland |

TABLE 1-continued Characteristics of the most important clonal complexes of Neisseria
meningitidis (data compiled from the PubMLST database Jun. 2, 2009).

| ST-complex | MLEE designation | No. isolates | No. STs | Dominant serogroups (%) | Dominant PorA | Dominant FetA | Disease/carriage ratio | Main origin |
|---|---|---|---|---|---|---|---|---|
| ST-22 complex | | 363 | 243 | W135 (52), NG (25) | 18-1, 3 | F4-1 | 0.6 | UK |
| ST-23 complex | Cluster A3 | 385 | 154 | Y (62), NG (18) | 5-1, 2-2 | F4-1 | 0.8 | Worldwide |
| ST-32 complex | ET-5 complex | 1028 | 350 | B (85) | 19, 15 | F5-1 | 3.5 | Worldwide |
| ST-35 complex | | 329 | 214 | B (59), NG (25) | 22-1, 14 | F4-1 | 0.5 | Worldwide |
| ST-41/44 complex | Lineage 3 | 1796 | 1274 | B (70) | 7-2, 4 | F1-5 | 1.2 | Worldwide |
| ST-53 complex | | 272 | 93 | NG (76) | 7-2, 30 | F1-7 | <0.1 | UK |
| ST-60 complex | | 225 | 148 | B (30), 29E (22), NG (19) | 5, 2 | F1-7 | 0.7 | Europe |
| ST-103 complex | | 127 | 84 | B (26), NG (22), C (16) | 18-1, 3 | F3-9 | 1.2 | Worldwide (-Africa) |
| ST-162 complex | | 140 | 63 | B (74), NG (13) | 22, 14 | F5-9 | 0.8 | Worldwide |
| ST-167 complex | | 201 | 144 | Y (47), NG (36) | 5-1, 10-4 | F3-4 | 0.5 | Worldwide |
| ST-198 complex | | 166 | 76 | NG (76) | 18, 25-15 | F5-5 | <0.1 | Worldwide |
| ST-213 complex | | 187 | 165 | B (74), NG (16) | 22, 14 | F5-5 | 0.6 | UK |
| ST-254 complex | | 148 | 107 | NG (35), B (24), 29E (12) | 5-1, 16 | F1-7, F3-6 | 0.5 | Worldwide |
| ST-269 complex | | 415 | 312 | B (73) | 22, 9 | F5-1 | 2.8 | Worldwide |
| ST-334 complex | | 106 | 64 | C (58), B (33) | 5-1, 2-2 | F1-5 | 5.7 | UK |

As shown in the above table, strains of e.g., serogroup B, belong to several clonal complexes. In particular, serogroup B strains are highly represented among significant invasive clonal complexes, including major clonal complexes spread worldwide i.e., ST-8, ST-18, ST-32, ST-41/44, ST162 and ST-269 clonal complexes, as well as clonal complex ST-11, remarkable for its very low rate of carriage relative to high incidence of disease.

To determine whether various protein antigens and combinations thereof are likely to give broad coverage across all strains of serogroup B, representative strains of that serogroup among major clonal complexes (6 ST complexes or groups) were selected and effectiveness in term of protection coverage of these various protein antigens and combinations thereof was tested against these strains.

It has now been found that a combination of at least two proteins of N. meningitidis other than those present in the licensed Bexsero® vaccine are able to offer a significant protection coverage over a collection of N. meningitidis strains of serogroup B, representative of the major invasive clonal complexes encountered worldwide.

This protection coverage has been evaluated by serum bactericidal activity (SBA) assay which reflects the ability of a given antigen to elicit bactericidal antibodies. The SBA assay measures functional activity of antibody through complement-mediated antibody lysis of the bacteria. Serum bactericidal activity has been accepted as a valid surrogate for predicting the clinical efficacy of serogroup B meningococcal vaccines.

Indirect evidence of SBA assay providing surrogate of protection came from studies by Goldschneider and colleagues in 1969 where an inverse correlation between the incidence of disease and the prevalence of serum bactericidal activity in human serum SBA against MenA, MenB and MenC were reported. In their prospective study, the SBA titer in serum was measured using human complement (e.g., endogenous complement or exogenous serum from a healthy adult who lacked intrinsic bactericidal activity). They demonstrated in incoming recruits to a US Army base that the presence of serum bactericidal activity strongly indicated resistance to meningococcal disease. This led to the establishment of SBA assay as the immunological surrogate of protection against meningococcal disease.

Indeed, in clinical trials of MenB vaccines, the measurement of the increase of the SBA titer after vaccination compared to the SBA basal titer (before any administration of the meningococcal vaccine) is an established clinical end point. Seroconversion is considered to be met when an SBA titer is superior or equal to 4. This approach was validated in 2005 at a World Health Organization sponsored meningococcal serology standardisation workshop and is based upon evidence from a number of efficacy studies of OMV vaccines.

Animal SBA assays achieved in upstream research are as well commonly acknowledged as a surrogate of protection for *N. meningitidis* vaccines. In the context of the present invention, initial SBA assays were first carried out against the homologous strain ('homologous' assays). Then, antigens, in particular those that gave positive results in the homologous SBA assay were taken forward into 'heterologous' SBA assays, in which the antigens-specific corresponding sera were tested against different strains, to give an indication of the vaccine coverage among epidemiologic relevant strains. The inventors of the present invention have determined that when the SBA titer (fold-increase compared to a negative control group) is superior or equal to 16 in homologous SBA assay, or superior or equal to 8 in heterologous SBA, protection is considered to be met.

An optimal vaccine shall give a broad coverage against a panel of representative strains of relevant invasive clonal complexes.

This is the reason why, the present invention relates to a composition, i.a. an immunogenic composition, comprising at least two *Neisseria meningitidis* (Nm) protein antigens selected from the group consisting of a trypsin-like serine protease auto-transporter antigen, a NalP antigen and a TbpB antigen. Preferably, the composition of the invention comprises (i) the trypsin-like serine protease auto-transporter antigen and (ii) the NalP antigen and/or TbpB antigen.

Although the polypeptides for use as antigens in the composition of the present invention are more particularly exemplified herein by reference to amino acid sequences of proteins that naturally-occur in a limited number of *N.*

*meningitidis* strains (M982 and B16B6 for TbpB, MC58 for NalP and trypsin-like serine protease auto-transporters), polypeptides of any naturally-occurring/allelic variant of *N. meningitidis* strain M982/B16B6/MC58 are also encompassed within the scope invention as well as any variant that may result from genetic engineering. By extension, the term variant is therefore applied to amino acid sequences, proteins or fragments thereof other than M982, B16B6 or MC58 sequences, proteins or fragments thereof. Variations in amino acid sequence may be introduced by substitution, deletion or insertion of one or more codons into the nucleic acid sequence encoding the protein that results in a change in the amino acid sequence of the protein without substantially affecting the tri-dimensional structure and/or the biological and/or immunogenic properties. Typically, the variation may result for an amino acid substitution that may be conservative or non-conservative, preferably conservative. A conservative substitution is an amino acid substitution in which an amino acid is substituted for another amino acid with similar structural and/or chemical properties.

In what follows, variants and/or mutants are described by reference to an amino acid sequence of reference. Such a description by reference is based on the prerequisite of optimal sequence alignment in order to determine the amino acid in the variant sequence that corresponds to the amino acid defined as being in a specific position in the amino acid of reference.

In what follows, variants and/or mutants are also described by percent identity with a sequence of reference. Percent identity between two amino acid sequences or two nucleotide sequences is determined with standard alignment algorithms as those described below.

Sequence alignment can be achieved and percent identity can also be determined by standard local alignment algorithms such as the Smith-Waterman algorithm (Smith et al., J. Mol. Biol. (1981) 147: 195) (available on the EBI web site) or Basic Local Alignment Tools (BLASTs; described in Altschul et al., (1990) J. Mol. Biol., 215: 403) available on the National Center for the Biotechnology Information (NCBI) web site at http://www.ncbi.nlm.nih.gov/BLAST and may be used using the default parameters.

In the context of the invention, variant and mutant amino acid sequences include amino acid sequences that have at least about 80% sequence identity with an amino acid sequence defined herein. Preferably, a variant or mutant amino acid sequence will have at least about 80%, 81%, 82%, 83%, 84%, 85%, 86%, 87%, 88%, 89%, 90%, 91%, 92%, 93%, 94%, 95%, 96%, 97%, 98%, 99% sequence identity to a polypeptide sequence as defined herein. Amino acid sequence identity is defined as the percentage of amino acid residues in the variant sequence that are identical with the amino acid residues in the reference sequence, after aligning the sequences and if necessary, introducing gaps, to achieve the maximum percent sequence identity, and not considering any conservative substitution as part of the sequence identity. Standard alignment algorithms cited above are useful in this regard.

Serine-Like Auto-Transporters of *N. meningitidis*

Auto-transporters are virulence factors produced by Gram-negative bacteria. Auto-transporters are modular proteins initially expressed as a precursor consisting of an N-terminal signal sequence and a C-terminal translocator domain separated by an N-terminal passenger domain that is secreted into the extra cellular medium. The signal sequence directs the auto-transporter to the secretion machinery for transport across the internal membrane. The translocator domain mediates the transport of the passenger domain across the outer membrane. The term auto-transporter was coined because of the apparent absence of dedicated secretion machinery.

On the basis of their N- and C-terminus domains, auto-transporters can be divided into several categories. The classical auto-transporters, as typified by the IgA1 protease, contain a catalytic site in the N-terminal half of the passenger domain which often, although not always, is involved in the autocatalytic release of the passenger domain from the cell surface. The catalytic site is constituted by an amino acid triad comprising a serine residue. Accordingly, these auto-transporters are classified as serine proteases.

The very first *N. meningitidis* auto-transporter that was described was indeed the IgA1 protease. The amino acid sequence precursor of this protein was first described in Lomholt et al., Mol. Microb. (1995) 15 (3): 495. Since then, the *N. meningitidis* IgA1 protease has been extensively studied and characterized (Vitovski & Sayers, Infect. Immun. (2007) 75 (6): 2875; Ulsen & Tommassen, FEMS Microbiol. Rev. (2006) 30 (2): 292). The IgA1 protease was proposed for vaccinal use in the early nineties (WO 90/11367).

After becoming publicly available, the genomes of *N. meningitidis* strains MC58 (serogroup B) (Tettelin et al., Science (March 2000) 287: 1809), Z2491 (serogroup A) and FAM18 (serogroup C) have been systematically searched for the presence of genes encoding auto-transporters. BLAST searches using known auto-transporters as search leads resulted in the identification of eight genes putatively encoding proteins with auto-transporter characteristics, four of which encode serine proteases:

- iga encoding IgA1 protease (IgA1P): NMB 0700, NMA 0905 and NMC 0651, respectively in the MC58 (serogroup B), Z2491 (serogroup A) and FAM18 (serogroup C) strain genomes;
- app encoding App (adhesion and penetration protein): NMB 1985, NMA 0457 and NMC 1969, respectively in the MC58, Z2491 and FAM18 strain genomes;
- ausI (mspA) encoding AusI (MspA): NMB 1998 in the MC58 genome; and
- nalP (aspA) encoding NalP (AspA): NMB 1969, NMA 0478 and NMC 1943 respectively in the MC58, Z2491 and FAM18 strain genomes.

Trypsin-Like Serine Protease Auto-Transporter Antigen of *N. meningitidis*

While NalP is known to be a subtilisin-like serine protease, IgA1P, App and AusI are classified as being chymotrypsin-like serine proteases (herein after called trypsin-like serine proteases). IgA1P, App and AusI are different proteins displaying similar tridimensional structure, as they are all auto-transporters, and share some sequence homology at least in the passenger domain, including the catalytic triad.

The translocator domain of trypsin-like serine proteases is essential for the transport of the passenger domain across the membrane. It is constituted of several hydrophobic beta-sheets integrated into the outer-membrane that form a channel through which the passenger domain is secreted and is accordingly designated under the term "beta domain". Typically, the IgA1P beta domain contains twelve beta sheets (Gripstra et al., Res. in Microbiol. (2013) 164: 562).

As described in Pohlner et al., Nature (1987) 325: 458, the ~160 kDa passenger domain of IgA1P essentially consists of two sub-domains: (i) the N-terminal sub-domain containing the protease activity (protease sub-domain) and (ii) a ~40 kDa alpha-peptide domain which are connected together via a small gamma-peptide. The two sub-domains can be released separately or as a single polypeptide.

For ease of description, the protease sub-domain together with the gamma peptide is referred hereinafter as a single entity under the term "protease domain". The protease sub-domain extends from the N-terminal end of the mature IgA1P polypeptide, to the PAPISP auto-cleavage site.

As a matter of example, the amino acid sequence of the IgA1P precursor of MC58 (NMB0700) is shown in SEQ ID NO: 1. Further details are to be found in Table 2A below.

App and AusI were studied more recently [van Ulsen et al., FEMS Immunol Med. Microb. (2001) 32: 53; Serruto et al., Mol. Microb. (2003) 48 (2): 323; van Ulsen et al., Microbes & Infection (2006) 8: 2088; Turner et al., Infect. Immun. (2006) 74 (5): 2957; Ulsen & Tommassen (supra); Henderson et al., Microbiol. Mol. Biol. Rev. (2004) 68 (4): 692]. App and AusI are both trypsin-like serine proteases, with FINTL as putative auto-cleavage site. Although the boundaries of their domains and sub-domains are less characterized than those of IgA1P, there is no doubt that they share the same domain organization as is apparent from Tables 2B and 2C. Genome analysis shows that App is quite conserved in *N. meningitidis*, with sequence identities compared with MC58 App being from 88 to 98%.

The boundaries of the IgA1P, App and AusI domains may vary slightly, as it is not always possible to precisely define a domain to the exact amino acid. For example, the domains may be defined as slightly different depending on the methods/techniques used by different scientists to identify them and on the strain origin of the sequences. Thus, the domains indicated in Table 2A to 2C may be defined according to the locations given herein and/or in the Figures, or according to said locations +/−1, 2, 3, 4, 5, 6, 7, 8, 9, 10 or more amino acids, i.e. 1, 2, 3, 4, 5, 6, 7, 8, 9, 10 or more amino acids N-terminal or C-terminal of said locations. A 'domain' of a trypsin-like serine protease auto-transporter protein as referred to herein may be said domain as defined in Table 2A, 2B or 2C, or may be said domain +/−1, 2, 3, 4, 5, 6, 7, 8, 9, 10 or more amino acids at the N-terminus and/or the C-terminus.

As already mentioned above, trypsin-like serine protease auto-transporters of *N. meningitidis* include IgA1P, App and AusI, each of them being useful within the frame of the present invention. Accordingly, the trypsin-like serine protease auto-transporter antigen may be e.g., an IgA1P, App or AusI antigen.

TABLE 2A

Domain structure of MC58 IgA1P (NMB0700)

| | | | Passenger domain | | | |
|---|---|---|---|---|---|---|
| Serine | | | Protease domain | | Alpha | |
| protease motif | Catalytic triad | Signal sequence | Protease sub-domain | Gamma-peptide | peptide domain | Beta-domain |
| 265-270 GDSGSP | 101H 150D 267S | 1-27 | 28-975 PAP | 976-1007 SP | 1008-1505 | 1506-1815 |

TABLE 2B

Domain structure of MC58 App (NMB1985)

| | | | Passenger domain | | | |
|---|---|---|---|---|---|---|
| Serine | | | Protease domain | | Alpha- | Beta-domain |
| protease motif | Catalytic triad | Signal sequence | Protease sub-domain | | peptide domain | (prediction Uniprot) |
| 265-270 GDSGSP | 115H 158D 267S | 1-41 | 42-956 956 F | 957-1056 NTL | 1057-1178 1057-1204* | 1205-1457 |

*based on pertactin

TABLE 2C

Domain structure of MC58 AusI (NMB1998)

| | | | Passenger domain | | | |
|---|---|---|---|---|---|---|
| | | | Protease domain | | | Beta- |
| Serine protease motif | Catalytic triad | Signal sequence | Protease sub-domain | | Alpha-peptide domain | domain (prediction Uniprot) |
| 239-244 GDSGSP | 100H 135D 241S | 1-26 | 27-870 870 F | 871-968 NTL | 969-1177 969-1131* | 1178-1431 |

*based on pertactin

According to a preferred embodiment, a trypsin-like serine protease auto-transporter antigen suitable for the invention may be as follows.

For use in the composition of the present invention, the trypsin-like serine protease auto-transporter antigen may be a polypeptide, preferably an isolated polypeptide, selected from polypeptides comprising or consisting of:

(I):

a full-length mature *N. meningitidis* trypsin-like serine protease auto-transporter; or a mutant of said a full-length mature *N. meningitidis* trypsin-like serine protease auto-transporter which lacks or has reduced trypsin-like serine protease activity and/or does not contain any cleavage site able/susceptible to be cleaved by a trypsin-like serine protease; or (II):

(A) a fragment of a full-length mature trypsin-like serine protease auto-transporter of *N. meningitidis*, said fragment consisting of:

(i) a protease domain of a trypsin-like serine protease auto-transporter of *N. meningitidis*; or (ii) a protease domain and all or part of an α-peptide domain of a trypsin-like serine protease auto-transporter of *N. meningitidis*; or (iii) a protease domain, an α-peptide domain and a part of a β-domain, in particular a part of the β-domain comprising at least one and no more than eleven β-sheets of a trypsin-like serine protease auto-transporter of *N. meningitidis; or*

(B) a mutant of said fragment (A) which lacks or has reduced trypsin-like serine protease activity and/or does not contain any cleavage site able/susceptible to be cleaved by a trypsin-like serine protease;

wherein said polypeptide under (A) or (B) does not comprise the said full-length mature trypsin-like serine protease auto-transporter of *N. meningitidis*; or (III):

a first fragment fused to a second fragment:

(1) said first fragment consisting of:

a protease domain or a protease sub-domain of a first trypsin-like serine protease auto-transporter of *N. meningitidis*, or a mutant of a protease domain or a protease sub-domain of a first trypsin-like serine protease auto-transporter of *N. meningitidis* which lacks or has reduced trypsin-like serine protease activity and/or does not contain any cleavage site able/susceptible to be cleaved by a trypsin-like serine protease, (2) said second fragment consisting of:

an α-peptide domain, and optionally a part of a β-domain, of a second trypsin-like serine protease auto-transporter of *N. meningitidis;* wherein the first and second trypsin-like serine protease auto-transporters are different; and wherein the C-terminus of the first fragment is fused to the N-terminus of the second fragment, wherein said polypeptide does not comprise the said full-length mature trypsin-like serine protease auto-transporter of *N. meningitidis*.

According to one embodiment, a trypsin-like serine protease auto-transporter of *N. meningitidis* suitable for the invention may be IgA1P, App or AusI, as above-described Polypeptides described under (II) (A) and (B) herein above are collectively referred to herein after as "Fragment Polypeptides". Polypeptides described under (Ill) herein above are collectively referred to herein after as "Fusion Polypeptide".

For use in the composition of the present invention, the trypsin-like serine protease auto-transporter antigen may be a trypsin-like serine protease auto-transporter polypeptide comprising or essentially consisting of:

(A) a full-length mature *N. meningitidis* trypsin-like serine protease auto-transporter; or (B) a mutant of (A) which lacks or has reduced trypsin-like serine protease activity and/or does not contain any cleavage site able/susceptible to be cleaved by a trypsin-like serine protease.

According to one embodiment, a trypsin-like serine protease auto-transporter of *N. meningitidis* suitable for the invention may be IgA1P, App or AusI, as above-described.

By "full-length mature trypsin-like serine protease auto-transporter" is meant the trypsin-like serine protease auto-transporter lacking the signal peptide.

Accordingly, by "full-length mature trypsin-like serine protease auto-transporter" is meant the full-length mature trypsin-like serine protease auto-transporter comprising (having) (i) a naturally-occurring full-length mature amino acid sequence or (ii) a naturally-occurring full-length mature amino acid sequence lacking at most the first 50, 40, 30, 20, 10 or 5 N-terminus amino acids and/or at most the last 5 C-terminus amino acids or (iii) a naturally-occurring full-length mature amino acid sequence fused to the 1, 2 or 3 amino acids of the C-terminus of the signal sequence.

As a matter of example, a naturally-occurring full-length mature *N. meningitidis* trypsin-like serine protease auto-transporter may be:

A naturally-occurring full-length mature IgA1P of strain MC58 (MC58 IgA1P) which may thus comprise (have) the amino acid sequence shown in SEQ ID NO: 1 (i) starting with alanine in position 28 and ending with amino acid in position 1815 [in SEQ ID NO: 1, the peptide signal which is by definition, not included in the mature form, is from amino acid in position 1 to amino acid in position 27]; or (ii) starting with an amino acid in any one of positions 27 or 28 to 78, preferably 27 or 28 to 58, more preferably 27 or 28 to 38, e.g. in position 27, 28, 29, 30, 31 or 32, and ending with an amino acid in any one of positions 1810 to 1815.

A naturally-occurring full-length mature App of strain MC58 (MC58 App) which may thus comprise (have) the amino acid sequence shown in SEQ ID NO: 2 (i) starting with alanine in position 42 or glycine in position 43 and ending with amino acid in position 1457 [in SEQ ID NO: 2, the peptide signal which is by definition, not included in the mature form, is from amino acid in position 1 to amino acid in position 41]; or (ii) starting with an amino acid in any one of positions 42 or 43 to 93, preferably 42 or 43 to 73, more preferably 42 or 43 to 53, e.g. in position 42, 43, 44, 45, 46 or 47, and ending with an amino acid in any one of positions 1453 to 1457.

A naturally-occurring full-length mature AusI of strain MC58 (MC58 AusI) which may thus comprise (have) the amino acid sequence shown in SEQ ID NO: 3 (i) starting with alanine in position 27 and ending with amino acid in position 1431 [in SEQ ID NO: 3, the peptide signal which is by definition, not included in the mature form, is from amino acid in position 1 to amino acid in position 26]; or (ii) starting with an amino acid in any one of positions 27 to 77, preferably 27 to 57, more preferably 27 to 37, e.g., in position 27, 28, 29, 30, 31 or 32, and ending with an amino acid in any one of positions 1426 to 1431.

Other useful full-length mature trypsin-like serine protease auto-transporters include variants of the MC58 full-length mature trypsin-like serine protease auto-transporters such as variants of MC58 full-length mature IgA1P, App or AusI.

Useful full-length mature IgA1P proteins include variants of MC58 IgA1P protein which may be described by reference to the MC58 amino acid sequence reported in SEQ ID NO: 1. These variants comprise (have) an amino acid sequence starting with an amino acid corresponding to the amino acid in position 28 and ending with an amino acid corresponding to the amino acid in position 1815. Other useful variants of the MC58 IgA1P protein, still described by reference to the MC58 amino acid sequence reported in SEQ ID NO: 1, comprise (have) an amino acid sequence starting with the amino acid corresponding to the amino acid in any one of the positions 28 to 78, preferably 28 to 58, more preferably 28 to 38, e.g. in position 27, 28, 29, 30, 31 or 32, in SEQ ID NO: 1, and ending with the amino acid corresponding to the amino acid in any one of positions 1810 to 1815 in SEQ ID NO: 1.

Useful full-length mature App proteins include variants of MC58 App protein which may be described by reference to the MC58 amino acid sequence reported in SEQ ID NO: 2. These variants comprise (have) an amino acid sequence starting with the amino acid corresponding to the amino acid in position 42 or 43 and ending with the amino acid corresponding to the amino acid in position 1457. Other useful variants of the MC58 App protein, still described by reference to the MC58 amino acid sequence reported in SEQ ID NO: 2, comprise (have) an amino acid sequence starting with the amino acid corresponding to the amino acid in any one of the positions 42 or 43 to 93, preferably 42 or 43 to 73, more preferably 42 or 43 to 53, e.g. in position 42, 43, 44, 45, 46 or 47, in SEQ ID NO: 2, and ending with the amino acid corresponding to the amino acid in any one of positions 1453 to 1457 in SEQ ID NO: 2.

Useful full-length mature AusI proteins include variants of MC58 AusI protein which may be described by reference to the MC58 amino acid sequence reported in SEQ ID NO: 3. These variants comprise (have) an amino acid sequence starting with the amino acid corresponding to the amino acid in position 27 and ending with the amino acid corresponding to the amino acid in position 1431. Other useful variants of the MC58 AusI protein, still described by reference to the MC58 amino acid sequence reported in SEQ ID NO: 3, comprise (have) an amino acid sequence starting with the amino acid corresponding to the amino acid in any one of the positions 27 to 77, preferably 27 to 57, more preferably 27 to 37, e.g., in position 27, 28, 29, 30, 31 or 32, in SEQ ID NO: 3, and ending with the amino acid corresponding to the amino acid in any one of positions 1426 to 1431 in SEQ ID NO: 3.

As mentioned above, for use in the composition of the present invention, the trypsin-like serine protease auto-transporter antigen suitable for the invention may also be a polypeptide comprising or consisting of a fragment of a full-length mature trypsin-like serine protease auto-transporter of *N. meningitidis*, such as IgA1P, App and AusI, which may be as described above.

Trypsin-like serine proteases are proteins with low solubility due to the presence of the beta-core and as a consequence of this, recombinant expression and purification of full-length trypsin-like serine proteases may be difficult to achieve. This is the reason why, in a preferred embodiment, the trypsin-like serine protease auto-transporter antigens may be produced as a truncated proteins, at least partially lacking the beta-core.

Accordingly, for use in the composition of the present invention, the trypsin-like serine protease auto-transporter antigen may accordingly be a polypeptide comprising or consisting of:

(A) a fragment of a full-length mature trypsin-like serine protease auto-transporter of *N. meningitidis*, said fragment consisting of:

(i) a protease domain of a trypsin-like serine protease auto-transporter of *N. meningitidis*; or (ii) a protease domain and all or part of an α-peptide domain of a trypsin-like serine protease auto-transporter of *N. meningitidis*; or (iii) a protease domain, an α-peptide domain and a part of a β-domain, in particular a part of the β-domain comprising at least one and no more than eleven β-sheets of a trypsin-like serine protease auto-transporter of *N. meningitidis*; or (B) a mutant of said fragment (A) which lacks or has reduced trypsin-like serine protease activity and/or does not contain any cleavage site able/susceptible to be cleaved by a trypsin-like serine protease;

wherein said polypeptide under (A) or (B) does not comprise the said full-length mature trypsin-like serine protease auto-transporter of *N. meningitidis*.

According to one embodiment, a trypsin-like serine protease auto-transporter of *N. meningitidis* suitable for the invention may be IgA1P, App or AusI, as above-described.

Advantageously, when the fragment essentially consists of option (iii), part of the beta domain may comprise at least one and no more than eight, six, four or preferably, two beta-sheets. Part of the beta domain may comprise from N-ter to C-ter, at least the first beta-sheet; (ii) first and second beta-sheets; (iii) first, second and third beta-sheets; (iv) first, second, third and fourth beta-sheets; (v) first, second, third, fourth and fifth beta-sheets; (vi) first, second, third, fourth, fifth and sixth beta-sheets; (viii) first, second, third, fourth, fifth, sixth and seventh beta-sheets; or (viii) first, second, third, fourth, fifth, sixth, seventh, and eighth beta-sheets; option (ii) being preferred.

According to one embodiment, an isolated polypeptide in accordance with the invention may consist of the protease domain of the trypsin-like serine protease auto-transporter of *N. meningitidis* which is IgA1P, App or AusI, and preferably is IgA1P.

According to one embodiment, an isolated polypeptide may consist of a protease domain and all or part of an α-peptide domain, and preferably of a passenger domain (protease domain and ox-peptide domain), of the trypsin-like serine protease auto-transporter of *N. meningitidis* which is IgA1P, App or AusI.

According to one embodiment, an isolated polypeptide in accordance with the invention may consist of the protease domain, the α-peptide domain (together the passenger domain) and a part of a β-domain, preferably the two first β-sheets of the 1-domain, of the trypsin-like serine protease auto-transporter IgA1P.

According to one embodiment, an isolated polypeptide in accordance with the invention may consist of the protease domain, the α-peptide domain (together the passenger domain) and a part of α-domain, preferably the two first β-sheets of the β-domain, of the trypsin-like serine protease auto-transporter App.

According to one embodiment, an isolated polypeptide in accordance with the invention may consist of the protease domain, the α-peptide domain (together the passenger domain) and a part of a β-domain, preferably the two first β-sheets of the β-domain, of the trypsin-like serine protease auto-transporter AusI.

According to one embodiment, an isolated polypeptide in accordance with the invention may have an amino acid sequence having at least 90% identity with the amino acid sequence of the IgA1P of *N. meningitidis* MC58 shown in SEQ ID NO: 1 starting from position 27, 28, 29, 30, 31 or 32 and ending at a position selected from position 1008 to position 1505.

According to one embodiment, an isolated polypeptide in accordance with the invention may have an amino acid sequence having at least 90% identity with the amino acid sequence of the IgA1P of *N. meningitidis* MC58 shown in SEQ ID NO: 1 starting from position 27, 28, 29, 30, 31 or 32 and ending at position 1002, 1003, 1004, 1005, 1006, 1007 or 1008.

According to another embodiment, an isolated polypeptide in accordance with the invention may have an amino acid sequence having at least 90% identity with the amino acid sequence of the IgA1P of *N. meningitidis* MC58 shown in SEQ ID NO 1 starting from position 27, 28, 29, 30, 31 or 32 and ending at a position selected from position 1500, 1501, 1502, 1503, 1504, 1505, 1506, 1507, 1508, 1509 and 1510.

According to another embodiment, an isolated polypeptide in accordance with the invention may have an amino acid sequence having at least 90% identity with the amino acid sequence of the IgA1P of *N. meningitidis* MC58 shown in SEQ ID NO: 1 starting from position 27, 28, 29, 30, 31 or 32 and ending at position 1580, 1581, 1582, 1583, 1584, 1585, 1586, 1587 or 1588.

As a matter of example, an IgA1P fragment may essentially consist of the protease domain of MC58 IgA1P comprising (having) the amino acid sequence shown in SEQ ID NO: 1

(i) starting with the amino acid in position 27 or 28 and ending with amino acid in position 1005; or (ii) starting with the amino acid in position 27, 28, 29, 30, 31 or 32 and ending with the amino acid in position 1002, 1003, 1004, 1005, 1006, 1007, or 1008; or (iii) starting with an amino acid in any one of positions 27 or 28 to 78, preferably 27 or 28 to 58, more preferably 27 or 28 to 38, and ending with an amino acid in any one of positions 990 to 1015, preferably 1000 to 1010, e.g., in position 1005.

Another example of an IgA1P fragment may essentially consist of the protease domain of a variant of MC58 IgA1P, said fragment being described by reference to the MC58 amino acid sequence reported in SEQ ID NO: 1 as comprising (having) an amino acid sequence (i) starting with the amino acid corresponding to the amino acid in position 27 or 28 and ending with the amino acid corresponding to the amino acid in position 1005;

(ii) starting with the amino acid corresponding to the amino acid in position 27, 28, 29, 30, 31 or 32 and ending with the amino acid corresponding to the amino acid in position 1002, 1003, 1004, 1005, 1006, 1007, or 1008; or (iii) starting with the amino acid corresponding to the amino acid in any one of the positions 28 to 78, preferably 28 to 58, more preferably 28 to 38, and ending with the amino acid corresponding to the amino acid in any one of positions 990 to 1015, preferably 1000 to 1010, e.g., in position 1005, in SEQ ID NO: 1.

Still as a matter of example, an IgA1P fragment may also be an MC58 IgA1P fragment essentially consisting of the IgA1P protease domain and all or part of the α-peptide domain and e.g., comprising (having) the amino acid sequence shown in SEQ ID NO: 1

(i) starting with the amino acid in position 27 or 28 and ending with the amino acid in any one of positions 1005 to 1510, preferably 1500 to 1510, more preferably in position 1505;

or (ii) starting with the amino acid in any one of positions 27 or 28 to 78, preferably 27 or 28 to 58, more preferably 27 or 28 to 38, and ending with the amino acid in any one of positions 1005 to 1510, preferably 1300 or 1500 to 1510, e.g. in position 1505.

Another example of an IgA1P fragment may be a fragment of a variant of MC58 IgA1P, said fragment essentially consisting of the IgA1P protease domain and all or part of the α-peptide domain and being described by reference to the MC58 amino acid sequence reported in SEQ ID NO: 1, which comprises (has) an amino acid sequence (i) starting with the amino acid corresponding to the amino acid in position 27 or 28 and ending with the amino acid corresponding to the amino acid in any one of positions 1005 to 1510, preferably 1500 to 1510, more preferably in position 1505; or (ii) starting with the amino acid corresponding to the amino acid in any one of positions 27 or 28 to 78, preferably 27 or 28 to 58, more preferably 27 or 28 to 38, and ending with the amino acid corresponding to the amino acid in any one of positions 1005 to 1510, preferably 1300 or 1500 to 1510, e.g., in position 1505, in SEQ ID NO: 1.

Still as a matter of example, an IgA1P fragment may also be the MC58 IgA1P fragment essentially consisting of the IgA1P protease domain, the α-peptide domain and part of the beta-domain e.g. comprising at least one and no more than eleven beta-sheets and e.g., comprising (having) the amino acid sequence shown in SEQ ID NO: 1

(i) starting with the amino acid in position 27 or 28 and ending with the amino acid in position 1584; or (ii) starting with the amino acid in any one of positions 27 or 28 to 78, preferably 27 or 28 to 58, more preferably 27 or 28 to 38, and ending with the amino acid in any one of positions 1505 to 1600, preferably 1550 to 1590, e.g. in position 1584.

Another example of an IgA1P fragment may be a fragment of a variant of MC58 IgA1P, said fragment essentially consisting of the IgA1P protease domain, the α-peptide domain and part of the beta-domain e.g. comprising at least one and no more than eleven beta-sheets and being described by reference to the MC58 amino acid sequence reported in SEQ ID NO: 1, which comprises (has) an amino acid sequence (i) starting with the amino acid corresponding to the amino acid in position 27 or 28 and ending with the amino acid corresponding to the amino acid in position 1584;

or (ii) starting with the amino acid corresponding to the amino acid in any one of positions 27 or 28 to 78, preferably 27 or 28 to 58, more preferably 27 or 28 to 38, and ending with the amino acid corresponding to the amino acid in any one of positions 1505 to 1600, preferably 1550 to 1590, e.g., in position 1584, in SEQ ID NO: 1.

According to a preferred embodiment, an isolated polypeptide in accordance with the invention may have an amino acid sequence having at least 90% identity with, and preferably may consist in, the amino acid sequence of the IgA1P of *N. meningitidis* MC58 shown in SEQ ID NO: 1 starting from position 26, 27, 28, 29 or 30, an preferably 28, and ending at position 1582, 1583, 1584, 1585 or 1586, and preferably 1584.

According to another preferred embodiment, an isolated polypeptide in accordance with the invention may have an amino acid sequence having at least 90% identity with, and preferably may consist in, the amino acid sequence of the IgA1P of *N. meningitidis* MC58 shown in SEQ ID NO: 1 starting from position 26, 27, 28, 29 or 30, an preferably 28, and ending at position 1003, 1004, 1005, 1006 or 1007, and preferably 1005.

The polypeptide in accordance with the invention, and in particular those preferred embodiments may further comprise a mutation in the catalytic site as described below to reduce or suppress the catalytic activity, preferably at the Serine in position 267. Preferably, the Serine may be change for a Valine.

According to one embodiment, an isolated polypeptide in accordance with the invention may have an amino acid sequence having at least 90% identity with the amino acid sequence of the App of *N. meningitidis* MC58 shown in SEQ ID NO: 2 starting from position 40, 41, 42, 43, 44, 45 or 46 and ending at a position selected from positions 1057 to position 1204.

According to one embodiment, an isolated polypeptide in accordance with the invention may have an amino acid sequence having at least 90% identity with the amino acid sequence of the App of *N. meningitidis* MC58 shown in SEQ ID NO: 2 starting from position 40, 41, 42, 43, 44, 45 or 46 and ending at position 1052, 1053, 1054, 1055, 1056, 1057, 1058, 1059 or 1060.

According to one embodiment, an isolated polypeptide in accordance with the invention may have an amino acid sequence having at least 90% identity with the amino acid sequence of the App of *N. meningitidis* MC58 shown in SEQ ID NO: 2 starting from position 40, 41, 42, 43, 44, 45 or 46 and ending at a position between 1170 and 1204 inclusive According to one embodiment, an isolated polypeptide in accordance with the invention may have an amino acid sequence having at least 90% identity with the amino acid sequence of the App of *N. meningitidis* MC58 shown in SEQ ID NO: 2 starting from position 40, 41, 42, 43, 44, 45 or 46 and ending at position 1220, 1220, 1221, 1223, 1224, 1225, 1226 or 1227.

As a matter of example, an App fragment may essentially consist of the protease domain of:

(i) MC58 App comprising (having) the amino acid sequence shown in SEQ ID NO: 2 starting with the amino acid in position 40, 41, 42, 43, 44, 45 or 46 and ending with amino acid in position 1052, 1053, 1055, 1056, 1057, 1058, 1059 or 1060; or (ii) a variant of MC58 App, said fragment being described by reference to the MC58 amino acid sequence reported in SEQ ID NO: 2 as comprising (having) an amino acid sequence (i) starting with an amino acid corresponding to the amino acid in position 40, 41, 42, 43, 44, 45 or 46 and ending with the amino acid corresponding to the amino acid in position 1052, 1053, 1055, 1056, 1057, 1058, 1059 or 1060, in SEQ ID NO: 2.

Still as a matter of example, an App fragment may also be the MC58 App fragment essentially consisting of the App protease domain and all or part of the α-peptide domain and e.g., comprising (having) the amino acid sequence shown in SEQ ID NO: 2

(i) starting with the amino acid in position 42 or 43 and ending with the amino acid in position 1175 or 1187; or (ii) starting with the amino acid in any one of positions 42 or 43 to 92, preferably 42 or 43 to 72, more preferably 42 or 43 to 52, and ending with the amino acid in any one of positions 1060 or 1160 to 1210, preferably 1170 to 1200, e.g., in position 1175 or 1187.

Another example of an App fragment may be a fragment of a variant of MC58 App, said fragment essentially consisting of the App protease domain and all or part of the α-peptide domain and being described by reference to the MC58 amino acid sequence reported in SEQ ID NO: 2, which comprises (has) an amino acid sequence (i) starting with the amino acid corresponding to the amino acid in position 42 or 43 and ending with the amino acid corresponding to the amino acid in position 1175 or 1187; or (ii) starting with the amino acid corresponding to the amino acid in any one of the positions 42 or 43 to 92, preferably 42 or 43 to 72, more preferably 42 or 43 to 52, and ending with the amino acid corresponding to the amino acid in any one of positions 1060 or 1160 to 1210, preferably 1170 to 1200, e.g., in position 1175 or 1187, in SEQ ID NO: 2.

Still as a matter of example, an App fragment may also be the MC58 App fragment essentially consisting of the App protease domain, the α-peptide domain and part of the beta-domain and e.g., comprising (having) the amino acid sequence shown in SEQ ID NO: 2

(i) starting with the amino acid in position 42 or 43 and ending with the amino acid in position 1224; or (ii) starting with the amino acid in any one of positions 42 or 43 to 92, preferably 42 or 43 to 72, more preferably 42 or 43 to 52, and ending with the amino acid in any one of positions 1175 to 1240, preferably 1210 to 1230, e.g., in position 1224.

Another example of an App may be a fragment of a variant of MC58 App, said fragment essentially consisting of the App protease domain, the α-peptide domain and part of the beta-domain and being described by reference to the MC58 amino acid sequence reported in SEQ ID NO: 2, which comprises (has) an amino acid sequence (i) starting with the amino acid corresponding to the amino acid in position 42 or 43 and ending with the amino acid corresponding to the amino acid in position 1224; or (ii) starting with the amino acid corresponding to the amino acid in any one of the positions 42 or 43 to 92, preferably 42 or 43 to 72, more preferably 42 or 43 to 52, and ending with the amino acid corresponding to the amino acid in any one of positions 1175 to 1240, preferably 1210 to 1230, e.g., in position 1224, in SEQ ID NO: 2.

According to a preferred embodiment, an isolated polypeptide in accordance with the invention may have an amino acid sequence having at least 90% identity with, and preferably may consist in, the amino acid sequence of the App of *N. meningitidis* MC58 shown in SEQ ID NO: 2 starting from position 41, 42, 43, 44 or 45, and preferably 43, and ending at position 1122, 1123, 1224, 1225 or 1126, and preferably 1224.

The polypeptide in accordance with the invention, and in particular those preferred embodiments may further comprise a mutation in the catalytic site as described below to reduce or suppress the catalytic activity, preferably at the Serine in position 267. Preferably, the Serine may be change for a Valine.

According to one embodiment, an isolated polypeptide in accordance with the invention may have an amino acid sequence having at least 90% identity with the amino acid sequence of the AusI of *N. meningitidis* MC58 shown in SEQ ID NO: 3 starting from position 26, 27, 28, 29, 30 or 31 and ending at a position selected from position 969 to position 1177.

According to one embodiment, an isolated polypeptide in accordance with the invention may have an amino acid sequence having at least 90% identity with the amino acid sequence of the AusI of *N. meningitidis* MC58 shown in SEQ ID NO: 3 starting from position 26, 27, 28, 29, 30 or 31 and ending at position 966, 967, 968, 969, 970, 971 or 972.

According to one embodiment, an isolated polypeptide in accordance with the invention may have an amino acid sequence having at least 90% identity with the amino acid sequence of the AusI of *N. meningitidis* MC58 shown in SEQ ID NO: 3 starting from position 26, 27, 28, 29, 30 or 31 and ending at a position between 1131 and 1177 inclusive.

According to one embodiment, an isolated polypeptide in accordance with the invention may have an amino acid sequence having at least 90% identity with the amino acid sequence of the AusI of *N. meningitidis* MC58 shown in SEQ ID NO: 3 starting from position 26, 27, 28, 29, 30 or 31 and ending at position 1194, 1195, 1196, 1197, 1198, 1199, 1200, 1201 or 1202.

As a matter of example, an AusI fragment may essentially consist of the protease domain of:

(i) MC58 AusI comprising (having) the amino acid sequence shown in SEQ ID NO: 3 starting with the amino acid in position 26, 27, 28, 29, 30 or 31 and ending with amino acid in position 965, 966, 967, 968, 969, 970, 971 or 972; or (ii) a variant of MC58 AusI, said fragment being described by reference to the MC58 amino acid sequence reported in SEQ ID NO: 3 as comprising (having) an amino acid sequence starting with an amino acid corresponding to the amino acid in position 26, 27, 28, 29, 30 or 31 and ending with the amino acid corresponding to the amino acid in position 965, 966, 967, 968, 969, 970, 971 or 972.

Still as a matter of example, an AusI fragment may be the MC58 AusI fragment essentially consisting of the AusI protease domain and all or part of the α-peptide domain and e.g., comprising (having) the amino acid sequence shown in SEQ ID NO: 3

(i) starting with the amino acid in position 26 or 27 and ending with the amino acid in any one of the positions 1130 to 1180, e.g., in position 1161; or (ii) starting with the amino acid in any one of positions 26 or 27 to 76, preferably 26 or 27 to 56, more preferably 26 or 27 to 36, and ending with the amino acid in any one of positions 972 or 1130 to 1180, e.g., in position 1161.

Another example of an AusI fragment may be a fragment of a variant of MC58 AusI, said fragment essentially consisting of the AusI protease domain and all or part of the α-peptide domain and being described by reference to the MC58 amino acid sequence reported in SEQ ID NO: 3, which comprises (has) an amino acid sequence (i) starting with the amino acid corresponding to the amino acid in position 26 or 27 and ending with the amino acid corresponding to the amino acid in any one of the positions 1130 to 1180, e.g., in position 1161; or (ii) starting with the amino acid corresponding to the amino acid in any one of the positions 26 or 27 to 76, preferably 26 or 27 to 56, more preferably 26 or 27 to 36, and ending with the amino acid corresponding to the amino acid in any one of positions 972 or 1130 to 1180, e.g., in position 1161, in SEQ ID NO: 3

Still as a matter of example, an AusI fragment may be the MC58 AusI fragment essentially consisting of the AusI protease domain, the α-peptide domain and part of the beta domain and e.g., comprising (having) the amino acid sequence shown in SEQ ID NO: 3

(i) starting with the amino acid in position 26 or 27 and ending with the amino acid in any one of the positions 1198; or (ii) starting with the amino acid in any one of positions 26 or 27 to 76, preferably 26 or 27 to 56, more preferably 26 or 27 to 36, and ending with the amino acid in any one of positions 1130 or 1180 to 1210, preferably 1190 to 1200, e.g., in position 1198.

Another example of an AusI fragment may be a fragment of a variant of MC58 AusI, said fragment essentially consisting of the AusI protease domain, the α-peptide domain and part of the beta-domain and being described by reference to the MC58 amino acid sequence reported in SEQ ID NO: 3, which comprises (has) an amino acid sequence (i) starting with the amino acid corresponding to the amino acid in position 26 or 27 and ending with the amino acid corresponding to the amino acid in any one of the positions 1130 to 1180; or (ii) starting with the amino acid corresponding to the amino acid in any one of the positions 26 or 27 to 76, preferably 26 or 27 to 56, more preferably 26 or 27 to 36, and ending with the amino acid corresponding to the amino acid in any one positions 1130 or 1180 to 1210, preferably 1190 to 1200, e.g., in position 1198, in SEQ ID NO: 3.

According to a preferred embodiment, an isolated polypeptide in accordance with the invention may have an amino acid sequence having at least 90% identity with, and preferably may consist in, the amino acid sequence of the AusI of *N. meningitidis* MC58 shown in SEQ ID NO: 3 starting from position 24, 25, 26, 27 or 28, and preferably 26, and ending at position 1196, 1197, 1198, 1199 or 1200, and preferably 1198.

The polypeptide in accordance with the invention, and in particular those preferred embodiments may further comprise a mutation in the catalytic site as described below to reduce or suppress the catalytic activity, preferably at the Serine in position 241. Preferably, the Serine may be change for a Valine.

As already mentioned above, in some embodiments, the full-length mature trypsin-like serine protease auto-transporter i.a., IgA1P, App or AusI, or a fragment thereof i.a., or a construct of a first fragment fused to a second fragment, such as described above, may be mutated so that it lacks or has reduced trypsin-like serine protease activity and/or does not contain any cleavage site susceptible/able to be cleaved by a trypsin-like serine protease. As a result of the mutation, the auto-transporter remains in a precursor state, the N-terminal protease sub-domain not being cleaved from the rest of the molecule. For example, protease activity may be reduced by 10, 20, 30, 40, 50, 60, 70, 80, 90, 95, 96, 97, 98, 99 or 100% compared to the wild type sequence. Protease activity may be assayed by, for example, the methods described in Vitovski et al., (1999) FASEB J. 13: 331.

Preferably, the full-length mature trypsin-like serine protease auto-transporter or a fragment thereof i.a., such as described above lacks trypsin-like serine protease activity. As already mentioned above, the catalytic triad of the serine protease auto-transporters responsible for the protease activity includes a Serine residue. In order to reduce or abolish the serine protease activity, any of the amino acids present in the catalytic triad (located in the protease sub-domain) may be mutated, advantageously by amino acid substitution. In a particular embodiment, one way to achieve that goal may be to substitute the Serine residue in the catalytic triad by any other amino acid, advantageously by Glycine, Threonine, Alanine, Leucine, Isoleucine or Valine, this latter amino acid being preferred.

Examples of useful mutated full-length mature IgA1P, App or AusI proteins include in particular any one of the MC58 full-length mature IgA1P, App and AusI proteins or variants thereof as described above, each being mutated so that it lacks or has reduced trypsin-like serine protease activity and/or does not contain any cleavage site susceptible/able to be cleaved by a trypsin-like serine protease.

Examples of useful mutated IgA1P, App or AusI fragments include in particular any one of the MC58 IgA1P, App or AusI fragments or variants thereof as described above, each being mutated so that it lacks or has reduced trypsin-like serine protease activity and/or does not contain any cleavage site susceptible/able to be cleaved by a trypsin-like serine protease.

As already mentioned above, the catalytic triad of IgA1P from *N. meningitidis* strain MC58 of SEQ ID NO: 1 is generally considered to be 101H 150D 267S. The catalytic triad of App from *N. meningitidis* strain MC58 of SEQ ID NO: 2 is generally considered to be 115H 158D 267S. The catalytic triad of AusI from *N. meningitidis* strain MC58 of SEQ ID NO: 3 is generally considered to be 100H 135D 241S. The catalytic residues of proteins from other *N. meningitidis* strains may be determined by reference to the corresponding MC58 amino acid sequences as described herein, for example by reference to SEQ ID NO: 1 in the case of IgA1P.

The catalytic triad of MC58 IgA1P is composed of His101, Asp150 and Ser267 in SEQ ID NO: 1. Accordingly, the catalytic triad of MC58 IgA1P variants is composed of amino acids corresponding to His101, Asp150 and Ser267 in the amino acid sequence of SEQ ID NO: 1; and accordingly, the mutation occurs at the position corresponding to His101, Asp150 and Ser267 of the amino acid sequence of SEQ ID NO: 1. While any of the amino acids being or corresponding to His101, Asp150 and Ser267 of the amino acid sequence of SEQ ID NO: 1 may be mutated, e.g. by substitution, it is preferred to substitute the serine residue in the catalytic triad by any other amino acid, advantageously by e.g. Glycine, Threonine, Alanine, Leucine, Isoleucine and Valine, this latter amino acid being preferred.

A useful mutation as described above may be introduced in any of the IgAIP polypeptides (IgAIP or fragments) thereof i.a., as described above. In particular, the mutation that may be introduced in MC58 IgA1P polypeptide sequences is S267V. In a similar manner, the mutation that may be introduced in MC58 variant polypeptide sequences is the substitution of the Serine residue in the catalytic triad with Valine.

As a matter of non-limiting illustration, particular examples include:

The S267V mutated MC58 IgA1P fragment which comprises (has) the amino acid sequence shown in SEQ ID NO: 1, starting with the amino acid in position 27 or 28, and ending with the amino acid in position 1005 or 1584; and in which Serine 267 is substituted by Valine; and A mutated variant of the S267V MC58 IgA1P fragment which may be described as follows by reference to the MC58 amino acid sequence reported in SEQ ID NO: 1: this mutated variant comprises (has) an amino acid sequence starting with an amino acid corresponding to the amino acid in position 27 or 28, and ending with an amino acid corresponding to the amino acid in position 1005 or 1584 and in which the amino acid corresponding to Serine 267 is substituted by Valine.

In some embodiments, a fragment polypeptide comprises or consists of an IgAIP fragment which essentially consists of:

(i) the IgA1P protease domain in which the Ser residue of the catalytic triad is optionally mutated by substitution with e.g., Valine, the α-peptide domain and at least one and no more than eleven beta-sheets, preferably the first and second beta-sheets 503; or (ii) the IgA1P protease domain in which the Ser residue of the catalytic triad is optionally mutated by substitution with e.g., Valine.

The catalytic triad of MC58 App is composed of His115, Asp158 and Ser267 in SEQ ID NO: 2. Accordingly, the catalytic triad of MC58 App variants is composed of amino acids corresponding to His15, Asp158 and Ser267 in the amino acid sequence of SEQ ID NO: 2; and accordingly, the mutation occurs at the position corresponding to His115, Asp158 and Ser267 of the amino acid sequence of SEQ ID NO: 2. While any of the amino acids being or corresponding to His115, Asp158 and Ser267 of the amino acid sequence of SEQ ID NO: 2 may be mutated e.g. by substitution, it is preferred to substitute the serine residue in the catalytic triad by any other amino acid, advantageously by e.g. Glycine, Threonine, Alanine, Leucine, Isoleucine and Valine, this latter amino acid being preferred.

A useful mutation as described above may be introduced in any of the App proteins or fragments thereof as described above. In particular, the mutation that may be introduced in MC58 App polypeptide sequences is S267V. In a similar manner, the mutation that may be introduced in MC58 variant App polypeptide sequences is the substitution of the Serine residue in the catalytic triad with Valine.

As a matter of non-limiting illustration, particular examples include:

The S267V mutated MC58 App fragment which comprises (has) the amino acid sequence shown in SEQ ID NO: 2, starting with the amino acid in position 42 or 43, and ending with the amino acid in position 1224; and in which Serine 267 is substituted by Valine; and A mutated variant of the S267V MC58 App fragment which may be described as follows by reference to the MC58 amino acid sequence reported in SEQ ID NO: 2: this mutated variant comprises (has) an amino acid sequence starting with an amino acid corresponding to the amino acid in position 42 or 43, and ending with an amino acid corresponding to the amino acid in position 1224 and in which the amino acid corresponding to Serine 267 is substituted by Valine.

The catalytic triad of MC58 AusI is composed of His100, Asp135 and Ser241 in SEQ ID NO: 3. Accordingly, the catalytic triad of MC58 AusI variants is composed of amino acids corresponding to His100, Asp135 and Ser241 in the amino acid sequence of SEQ ID NO: 3; and accordingly, the mutation occurs at the position corresponding to His100, Asp135 and Ser241 of the amino acid sequence of SEQ ID NO: 3. While any of the amino acids being or corresponding to His100, Asp135 and Ser241 of the amino acid sequence of SEQ ID NO: 3 may be mutated e.g. by substitution, it is preferred to substitute the serine residue in the catalytic triad by any other amino acid, advantageously by e.g. Glycine, Threonine, Alanine, Leucine, Isoleucine and Valine, this latter amino acid being preferred.

A useful mutation as described above may be introduced in any of the AusI proteins or fragments thereof as described above. In particular, the mutation that may be introduced in MC58 AusI polypeptide sequences is S241V. In a similar manner, the mutation that may be introduced in MC58 variant AusI polypeptide sequences is the substitution of the Serine residue in the catalytic triad with Valine.

As a matter of non-limiting illustration, particular examples include:

The S241V mutated MC58 AusI fragment which comprises (has) the amino acid sequence shown in SEQ ID NO: 3, starting with the amino acid in position 26 or 27 and ending with the amino acid in position 1198 and in which Serine 241 is substituted by Valine; and A mutated variant of the S241V MC58 AusI fragment which may be described as follows by reference to the MC58 amino acid sequence reported in SEQ ID NO: 3: this mutated variant comprises (has) an amino acid sequence starting with an amino acid corresponding to the amino acid in position 26 or 27, and ending with an amino acid corresponding to the amino acid in position 1198 and in which the amino acid corresponding to the Serine 267 is substituted by Valine.

In other words, the IgA1P antigen may be an IgA1P polypeptide comprising or consisting of:

A full-length mature IgA1P protein (i.e., a full-length mature MC58 IgA1P protein or a variant thereof), being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 1, starting with the amino acid in position 27, 28, 29, 30, 31, or 32 and ending with the amino acid in position 1815;

An IgA1P fragment (i.e., a MC58 IgA1P fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 1, starting with the amino acid in position 27, 28, 29, 30, 31, or 32 and ending with the amino acid in position 1002, 1003, 1004, 1005, 1006, 1007 or 1008;

An IgA1P fragment (i.e., a MC58 IgA1P fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 1, starting with the amino acid in position 27, 28, 29, 30, 31, or 32 and ending with the amino acid at a position selected from positions 1008 to 1505 inclusive;

An IgAIP fragment (i.e., a MC58 IgAIP fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 1, starting with the amino acid in position 27, 28, 29, 30, 31, or 32 and ending with the amino acid in position 1500, 1501, 1502, 1503, 1504, 1505, 1506, 1507, 1508, 1509 or 1510;

An IgA1P fragment (i.e., a MC58 IgA1P fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 1, starting with the amino acid in position 27, 28, 29, 30, 31, or 32 and ending with the amino acid in any one of positions 1506 to 1700, preferably 1506 to 1600, more preferably 1550 to 1600; OR An IgA1P fragment (i.e., a MC58 IgA1P fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 1, starting with the amino acid in position 27, 28, 29, 30, 31, or 32 and ending with amino acid in position 1580, 1581, 1582, 1583, 1584, 1585, 1586, 1587, or 1588.

In other words, the App antigen may be an App polypeptide comprising or consisting of:

A full-length mature App protein (i.e., a full-length mature MC58 App protein or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 2, starting with the amino acid in position 40, 41, 42, 43, 44, 45 or 46 and ending with the amino acid in position 1457;

An App fragment (i.e., a MC58 App fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 2, starting with the amino acid in position 40, 41, 42, 43, 44, 45 or 46 and ending with the amino acid in position 1052, 1053, 1054, 1055, 1056, 1057, 1058, 105 or 1060;

An App fragment (i.e., a MC58 App fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 2, starting with the amino acid in position 40, 41, 42, 43, 44, 45 or 46 and ending with the amino acid at a position selected from positions 1057 to 1204 inclusive;

An App fragment (i.e., a MC58 App fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 2, starting with the amino acid in position 40, 41, 42, 43, 44, 45 or 46 and ending with the amino acid at a position between 1170 and 1204 inclusive;

An App fragment (i.e., a MC58 App fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 2, starting with the amino acid in position 40, 41, 42, 43, 44, 45 or 46 and ending with the amino acid in any one of positions 1205 to 1400, preferably 1205 to 1300, more preferably 1220 to 1260; OR An App fragment (i.e., a MC58 App fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 2, starting with the amino acid in position 40, 41, 42, 43, 44, 45 or 46 and ending with amino acid in position 1220, 1221, 1222, 1223, 1224, 1225, 1226, or 1227.

In other words, the AusI antigen may be an AusI polypeptide comprising or consisting of:

A full-length mature MC58 AusI protein (i.e., a full-length mature MC58 AusI protein or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 3, starting with the amino acid in position 26, 27, 28, 29, 30 or 31 and ending with amino acid in position 1431;

An AusI fragment (i.e., a MC58 AusI fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 3, starting with the amino acid in position 26, 27, 28, 29, 30 or 31 and ending with amino acid in position 1052, 966, 967, 968, 969, 970, 971 or 972;

An AusI fragment (i.e., a MC58 AusI fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 3, starting with the amino acid in position 26, 27, 28, 29, 30 or 31 and ending with amino acid at a position selected from positions 969 to 1177;

An AusI fragment (i.e., a MC58 AusI fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 3, starting with the amino acid in position 26, 27, 28, 29, 30 or 31 and ending with amino acid at a position between 1131 and 1177 inclusive;

An AusI fragment (i.e., a MC58 AusI fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 3, starting with the amino acid in position 26, 27, 28, 29, 30 or 31 and ending with amino acid in any one of positions 1178 to 1300, preferably 1178 to 1250, more preferably 1180 to 1220; OR An AusI fragment (i.e., a MC58 AusI fragment or a variant thereof) being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 3, starting with the amino acid in position 26, 27, 28, 29, 30 or 31 and ending with amino acid in position 1220, 1195, 1196, 1197, 1198, 1199, 1200, or 1201.

For use in the composition of the present invention, the trypsin-like serine protease auto-transporter antigen may also be i.a., a fusion polypeptide comprising or consisting of:
a first fragment fused to a second fragment:
(1) said first fragment consisting of:
a protease domain or a protease sub-domain of a first full-length mature trypsin-like serine protease auto-transporter of N. meningitidis, or
a mutant of a protease domain or a protease sub-domain of a first trypsin-like serine protease auto-transporter of N. meningitidis which lacks or has reduced trypsin-like serine protease activity and/or does not contain any cleavage site able/susceptible to be cleaved by a trypsin-like serine protease,
(2) said second fragment consisting of:
an α-peptide domain, and optionally a part of a β-domain, of a second full-length mature trypsin-like serine protease auto-transporter of N. meningitidis;
wherein the first and second trypsin-like serine protease auto-transporters are different; and
wherein the C-terminus of the first fragment is fused to the N-terminus of the second fragment,
wherein said polypeptide does not comprise the said full-length mature trypsin-like serine protease auto-transporter of N. meningitidis.

A trypsin-like serine protease auto-transporter of N. meningitidis suitable for the invention may be IgA1P, App or AusI.

Advantageously, in the fusion polypeptide, the first fragment may essentially consist of (be) the protease domain or protease sub-domain, and preferably is a protease sub-domain, of the first trypsin-like serine protease auto-transporter. In an advantageous and independent manner, the second fragment may essentially consist of (be) the α-peptide domain, and optionally part of the β-domain, of the second trypsin-like serine protease auto-transporter.

In some embodiments, in the fusion polypeptide, (i) the first fragment essentially consists of (is) the protease domain or protease sub-domain of the first trypsin-like serine protease auto-transporter and (ii) the second fragment essentially consists of the α-peptide domain and part of the β-domain of the second trypsin-like serine protease auto-transporter.

According to one embodiment, a polypeptide of the invention may comprise or consist of a first fragment fused to a second fragment wherein said first fragment consists of a protease sub-domain of said first trypsin-like serine protease auto-transporter and said second fragment consist of an α-peptide domain, optionally with a part of a 1-domain, of said second trypsin-like serine protease auto-transporter.

According to a preferred embodiment, a polypeptide of the invention may comprise or consist of a first fragment fused to a second fragment wherein said first fragment consists of a protease sub-domain of said first trypsin-like serine protease auto-transporter which is IgA1P, and said second fragment consist of an α-peptide domain, optionally with a part of a β-domain, of said second trypsin-like serine protease auto-transporter which is App or AusI.

In a particular embodiment, part of the β-domain of the second fragment useful in the fusion polypeptide comprises at least one and no more than eleven β-sheets; preferably from two to eight β-sheets, more preferably from two to four β-sheets, most preferably two β-sheets. In practice, the C-terminus of the α-peptide domain is fused to the N-terminus of the β-domain which comprises from N-ter to C-ter, at least the first beta-sheet; (ii) first and second beta-sheets; (iii) first, second and third beta-sheets; (iv) first, second, third and fourth beta-sheets; (v) first, second, third, fourth and fifth beta-sheets; (vi) first, second, third, fourth, fifth and sixth beta-sheets; (viii) first, second, third, fourth, fifth, sixth and seventh beta-sheets; or (viii) first, second, third, fourth, fifth, sixth, seventh, and eighth beta-sheets; option (ii) being preferred.

For use in the fusion polypeptide, the first fragment may be mutated in the catalytic triad as described above with respect to the full-length mature trypsin-like serine protease auto-transporter of N. meningitidis, such as IgA1P, App or AusI, or the described fragments thereof. Indeed, the catalytic triad is located in the protease sub-domain. It may also be not mutated, especially when this first fragment essentially consists of the protease sub-domain that is the protease domain lacking the C-terminus amino acids containing the auto-cleavage site.

The first and second fragments may independently be a trypsin-like serine protease fragment of an MC58 strain or a variant thereof.

According to one embodiment, an isolated peptide in accordance with the invention comprising or consisting of a first fragment fused to a second fragment may comprise or consist of a first fragment having at least 90% identity with an amino acid sequence of the IgA1P of N. meningitidis MC58 shown in SEQ ID NO: 1 starting from position 27, 28, 29, 30, 31 or 32 and ending at position 1002, 1003, 1004, 1005, 1006, 1007 or 1008;

and may comprise or consist of a second fragment having at least 90% identity with an amino acid sequence of
(i) App of N. meningitidis MC58 shown in SEQ ID NO: 2 starting from position 1057, 1058, 1059, 1060, 1061 or 1062 and ending at a position between 1170 and 1204 inclusive; or
(ii) AusI of N. meningitidis MC58 shown in SEQ ID NO: 3 starting from position 969, 970, 971, 972, 973, 974, 975, 976, 977, 978, 979 or 980 and ending at a position between 1131-1177 inclusive.

According to another embodiment, an isolated peptide in accordance with the invention comprising or consisting of a first fragment fused to a second fragment may comprise or consist of a first fragment having at least 90% identity with an amino acid sequence of the IgA1P of *N. meningitidis* MC58 shown in SEQ ID NO: 1 starting from position 27, 28, 29, 30, 31 or 32 and ending at position 960, 961, 962, 963, 964, 965, 966, 967, 968, 969, 9701, 971, 972, 973, 974, 975, 976, 977, 978, 979 or 980;

and may comprise or consist of a second fragment having at least 90% identity with an amino acid sequence of (i) App of *N. meningitidis* MC58 shown in SEQ ID NO: 2 starting from position 1057, 1058, 1059, 1060, 1061 or 1062 and ending at a position between 1170 and 1204 inclusive; or (ii) AusI of *N. meningitidis* MC58 shown in SEQ ID NO: 3 starting from position 969, 970, 971, 972, 973, 974, 975, 976, 977, 978, 979 or 980 and ending at a position between 1131 and 1177 inclusive.

According to another embodiment, an isolated peptide in accordance with the invention comprising or consisting of a first fragment fused to a second fragment may comprise or consist of a first fragment having at least 90% identity with an amino acid sequence of the IgA1P of *N. meningitidis* MC58 shown in SEQ ID NO: 1 starting from position 27, 28, 29, 30, 31 or 32 and ending at position 960, 961, 962, 963, 964, 965, 966, 967, 968, 969, 9701, 971, 972, 973, 974, 975, 976, 977, 978, 979 or 980;

and may comprise or consist of a second fragment having at least 90% identity with an amino acid sequence of (i) App of *N. meningitidis* MC58 shown in SEQ ID NO: 2 starting from position 1057, 1058, 1059, 1060, 1061 or 1062 and ending at a position between 1170 and 1204 inclusive, and preferably at a position 1183, 1184, 1185, 1186, 1187, 1188, 1189, 1190 or 1191; or (ii) App of *N. meningitidis* MC58 shown in SEQ ID NO: 2 starting from position 1057, 1058, 1059, 1060, 1061 or 1062 and ending at a 1220, 1221, 1222, 1223, 1224, 1125, 1226, 1227, or 1228; or (iii) AusI of *N. meningitidis* MC58 shown in SEQ ID NO: 3 starting from position 969, 970, 971, 972, 973, 974, 975, 976, 977, 978, 979 or 980 and ending at a position between 1131 and 1177 inclusive, and preferably at a position 1157, 1158, 1159, 1160, 1161, 1162, 1163, 1164, or 1165; or (iv) AusI of *N. meningitidis* MC58 shown in SEQ ID NO: 3 starting from position 969, 970, 971, 972, 973, 974, 975, 976, 977, 978, 979 or 980 and ending at a position between 1194, 1195, 1196, 1197, 1198, 1199, 1200, 1201 or 1202.

In a particular embodiment, the above constructs may further comprise a mutation in the catalytic site as previously described to reduce or suppress the catalytic activity. The mutation may in particular intervene at the Serine in position 267, which may, for instance, be replaced with a Valine.

As a matter of non-limiting illustration, the first fragment may be e.g. the MC58 IgAIP protease sub-domain and may be fused to the alpha-peptide domain of e.g. App of a variant of the MC58 strain.

In some embodiments, the first fragment in the fusion polypeptide essentially consists of the protease domain or the protease sub-domain of IgAIP, mutated or not as described above, and is fused to the second fragment which essentially consists of the α-peptide domain and optionally, part of the β-domain of App or AusI.

A particular example of these embodiments is an IgA1P-App fusion polypeptide which essentially consists of the IgA1P protease sub-domain in which the Ser residue of the catalytic triad is optionally mutated by substitution with e.g., Valine, fused to the App α-peptide domain.

As a matter of example, the fusion polypeptide comprises or consists of the protease sub-domain or protease domain of MC58 IgA1P, optionally bearing a mutation in the catalytic triad, fused to the alpha-peptide domain of MC58 App or AusI. Accordingly, such an MC58 fusion polypeptide may comprise or consist of:

(i) a protease sub-domain of MC58 IgA1P comprising (having) the amino acid sequence shown in SEQ ID NO: 1, optionally bearing the S267V mutation,
  starting with the amino acid in position 27 or 28 and ending with the amino acid in position 966; or
  starting with the amino acid in position 27, 28, 29, 30, 31 or 32 and ending with the amino acid in position 963, 964, 965, 966, 967, 968, or 969; or
  starting with the amino acid in any one of positions 27 or 28 to 78, preferably 27 or 28 to 58, more preferably 27 or 28 to 38, and ending with the amino acid in any one of positions 960 to 975, preferably 965 to 970, e.g., in position 966; or (ii) a protease domain of MC58 IgA1P comprising (having) the amino acid sequence shown in SEQ ID NO: 1, optionally bearing the S267V mutation,
  starting with the amino acid in position 27 or 28 and ending with the amino acid in position 1005; or
  starting with the amino acid in position 27, 28, 29, 30, 31 or 32 and ending with the amino acid in position 1002, 1003, 1004, 1005, 1006, 1007 or 1008; or
  starting with the amino acid in any one of positions 27 or 28 to 78, preferably 27 or 28 to 58, more preferably 27 or 28 to 38, and ending with the amino acid in any one of positions 990 to 1015, preferably 1000 to 1010, e.g. in position 1005;

fused to:

(i) the alpha peptide domain of MC58 App comprising (having) the amino acid sequence shown in SEQ ID NO: 2 starting with the amino acid in any one of positions 1050 to 1070, preferably 1055 to 1065, e.g. in position 1055, 1056, 1057, 1058, 1059, 1060 or 1061 and ending with the amino acid in any one of positions 1160 to 1210, preferably 1170 to 1210, more preferably in position 1175 or 1187; or (ii) the alpha-peptide domain of MC58 AusI comprising (having) the amino acid sequence shown in SEQ ID NO: 3 starting with the amino acid in any one of positions 965 to 980, preferably 969 to 975, e.g., in position 974 and ending with the amino acid in any one of positions 1130 to 1180, preferably 1155 to 1165, e.g., in position 1161.

Another example of a fusion polypeptide may be a fusion polypeptide which may be described by reference to the MC58 amino acid sequences reported in SEQ ID NO: 1, 2 and/or 3 as comprising or consisting of:

(i) the protease sub-domain of a variant of MC58 IgA1P comprising (having) the amino acid sequence described by reference to the amino acid sequence of SEQ ID NO: 1, optionally bearing the S267V mutation,
  starting with the amino acid corresponding to the amino acid in position 27 or 28 and ending with the amino acid corresponding to the amino acid in position 966; or
  starting with the amino acid corresponding the amino acid in position 27, 28, 29, 30, 31 or 32 and ending with the amino acid corresponding the amino acid in position 963, 964, 965, 966, 967, 968, or 969; or
  starting with the amino acid corresponding the amino acid in any one of positions 27 or 28 to 78, preferably 27 or 28 to 58, more preferably 27 or 28 to 38, and ending with the amino acid corresponding the amino acid in any one of positions 960 to 975, preferably 965 to 970, e.g., in position 966; or
(ii) the protease domain of a variant of MC58 IgA1P comprising (having) an amino acid sequence described by reference to the amino acid sequence of SEQ ID NO: 1, optionally bearing the S267V mutation,
starting with the amino acid corresponding to the amino acid in position 27 or 28 and ending with the amino acid corresponding to the amino acid in position 1005; or
starting with the amino acid corresponding to the amino acid in position 27, 28, 29, 30, 31 or 32 and ending with the amino acid corresponding to the amino acid in position 1002, 1003, 1004, 1005, 1006, 1007 or 1008; or
starting with the amino acid corresponding to the amino acid in any one of positions 27 or 28 to 78, preferably 27 or 28 to 58, more preferably 27 or 28 to 38, and ending with the amino acid corresponding to the amino acid in any one of positions 990 to 1015, preferably 1000 to 1010, e.g. in position 1005;
fused to:
(i) the alpha-peptide domain of a variant of MC58 App comprising (having) an amino acid sequence described by reference to the amino acid sequence shown in SEQ ID NO: 2 starting with the amino acid corresponding to the amino acid in any one of positions 1050 to 1070, preferably 1055 to 1065, e.g. in position 1055, 1056, 1057, 1058, 1059, 1060 or 1061 and ending with the amino acid corresponding to the amino acid in any one of positions 1160 to 1210, preferably 1170 to 1210, more preferably in position 1175 or 1187; or
(ii) the alpha-peptide domain of a variant of MC58 AusI comprising (having) an amino acid sequence described by reference to the amino acid sequence shown in SEQ ID NO: 3 starting with the amino acid corresponding to the amino acid in any one of positions 965 to 980, preferably 969 to 975, e.g., in position 974 and ending with the amino acid corresponding to the amino acid in any one of positions 1130 to 1180, preferably 1155 to 1165, e.g., in position 1161.
Specific non-limiting examples include i.a.:
an MC58 fusion polypeptide comprising or consisting of a first fragment comprising (having) the amino acid sequence shown in SEQ ID NO: 1 starting with the amino acid in position 27 or 28 and ending with amino acid in position 966, optionally bearing the S267V mutation; fused to a second fragment comprising (having) the amino acid sequence shown in:
(i) SEQ ID NO: 2 starting with the amino acid in position 1061 and ending with the amino acid in position 1187; or
(ii) SEQ ID NO: 3 starting with the amino acid in position 974 and ending with the amino acid in position 1161.
A fusion polypeptide comprising or consisting of a first fragment comprising (having) an amino acid sequence described by reference to the amino acid sequence shown in SEQ ID NO: 1, optionally bearing a mutation corresponding to the S267V mutation, starting with the amino acid corresponding to the amino acid in position 27 or 28 and ending with the amino acid corresponding to the amino acid in position 966; fused to a second fragment comprising (having) an amino acid sequence described by reference to the amino acid sequence shown in:
(i) SEQ ID NO: 2 starting with the amino acid corresponding to the amino acid in position 1061 and ending with the amino acid corresponding to the amino acid in position 1187; or
(ii) SEQ ID NO: 3 starting with the amino acid corresponding to the amino acid in position 974 and ending with the amino acid corresponding to the amino acid in any one of positions ending with the amino acid in position 1161.

In some other embodiments, the first fragment in the fusion polypeptide essentially consists of the protease domain or the protease sub-domain of App, mutated or not as described above, and is fused to the second fragment which essentially consists of the α-peptide domain and optionally of part of the β-domain of IgA1P or AusI.

Still in some other embodiments, the first fragment in the fusion polypeptide essentially consists of the protease domain or the protease sub-domain of AusI, mutated or not as described above, and is fused to the second fragment which essentially consists of the α-peptide domain and optionally of part of the β-domain of App or IgA1P.

In some embodiments, the fusion polypeptide has first and second amino acid sequences, the C-terminus of the first sequence being fused to the N-terminus of the second sequence,
wherein the first sequence has at least 90% identity with the amino acid sequence of the IgA1P of *N. meningitidis* MC58 shown in SEQ ID NO: 1 starting from position 27, 28, 29, 30, 31 or 32 and ending at position 1002, 1003, 1004, 1005, 1006, 1007 or 1008; and
wherein the second sequence has at least 90% identity with the amino acid sequence of:
(i) App of *N. meningitidis* MC58 shown in SEQ ID NO: 2 starting from position 1057, 1058, 1059, 1060, 1061 or 1062 and ending at a position between 1170 and 1204 inclusive, preferably position 1187; or
(ii) AusI of *N. meningitidis* MC58 shown in SEQ ID NO: 3 starting from position 969, 970, 971, 972, 973, 974, 975, 976, 977, 978, 979 or 980 and ending at a position between 1131-1177 inclusive, preferably position 1161; or
(iii) App of *N. meningitidis* MC58 shown in SEQ ID NO: 2 starting from position 1057, 1058, 1059, 1060, 1061 or 1062 and ending at a position 1220, 1221, 1222, 1223, 1224, 1225 and 1226, preferably position 1224; or
(iv) AusI of *N. meningitidis* MC58 shown in SEQ ID NO: 3 starting from position 969, 970, 971, 972, 973, 974, 975, 976, 977, 978, 979 or 980 and ending at a position 1195, 1196, 1197, 1198, 1199, 1200, 1201, preferably position 1198.

According to another embodiment, an isolated peptide in accordance with the invention comprising or consisting of a first fragment fused to a second fragment may comprise or consist of a first fragment having at least 90% identity with an amino acid sequence of the App of *N. meningitidis* MC58 shown in SEQ ID NO: 2 starting from position 40, 41, 42, 43, 44, 45 or 46 and ending at position 1052, 1053, 1054, 1055, 1056, 1057, 1058, 1059 or 1060;
and may comprise or consist of a second fragment having at least 90% identity with an amino acid sequence of
(i) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 1114 and ending at a position selected from position 1500, 1501, 1502, 1503, 1504, 1505, 1506, 1507, 1508, 1509 and 1510; or (ii) AusI of *N. meningitidis* MC58 shown in SEQ ID NO: 3 starting from position 969, 970, 971, 972, 973, 974, 975, 976, 977, 978, 979 or 980 and ending at a position between 1131-1177 inclusive.

In some embodiments, the fusion polypeptide has first and second amino acid sequences, the C-terminus of the first sequence being fused to the N-terminus of the second sequence, wherein the first sequence has at least 90% identity with the amino acid sequence of the App of *N. meningitidis* MC58 shown in SEQ ID NO: 2 starting from position 40, 41, 43, 44, 45 or 46 and ending at position 1052, 1053, 1054, 1055, 1056, 1057, 1058, 1059 or 1060; and wherein the second sequence has at least 90% identity with the amino acid sequence of (i) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 114 and ending at a position selected from position 1500, 1501, 1502, 1503, 1504, 1505, 1506, 1507, 1508, 1509 and 1510; or (ii) AusI of *N. meningitidis* MC58 shown in SEQ ID NO: 3 starting from position 969, 970, 971, 972, 973, 974, 975, 976, 977, 978, 979 or 980 and ending at a position between 1131-1177 inclusive, preferably position 1161.

(iii) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 114 and ending at a position selected from position 1580, 1581, 1582, 1583, 1584, 1585, 1586, 1587, and 1588, preferably 1584; or (iv) AusI of *N. meningitidis* MC58 shown in SEQ ID NO: 3 starting from position 969, 970, 971, 972, 973, 974, 975, 976, 977, 978, 979 or 980 and ending at a position 1195, 1196, 1197, 1198, 1199, 1200, 1201, preferably position 1198.

According to another embodiment, an isolated peptide in accordance with the invention comprising or consisting of a first fragment fused to a second fragment may comprise or consist of a first fragment having at least 90% identity with an amino acid sequence of the AusI of *N. meningitidis* MC58 shown in SEQ ID NO: 3 starting from position 26, 27, 28, 29, 30 or 31 and ending at position 966, 967, 968, 969, 970, 971 or 972;

and may comprise or consist of a second fragment having at least 90% identity with an amino acid sequence of (i) App of *N. meningitidis* MC58 shown in SEQ ID NO: 2 starting from position 1057, 1058, 1059, 1060, 1061 or 1062 and ending at a position between 1170 and 1204 inclusive; or (ii) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 1114 and ending at a position selected from position 1500, 1501, 1502, 1503, 1504, 1505, 1506, 1507, 1508, 1509 and 1510.

In some embodiments, the fusion polypeptide has first and second amino acid sequences, the C-terminus of the first sequence being fused to the N-terminus of the second sequence, wherein the first sequence has at least 90% identity with the amino acid sequence of the AusI of *N. meningitidis* MC58 shown in SEQ ID NO: 3 starting from position 26, 27, 28, 29, 30 or 31 and ending at position 966, 967, 968, 969, 970, 971 or 972; and wherein the second sequence has at least 90% identity with the amino acid sequence of (i) App of *N. meningitidis* MC58 shown in SEQ ID NO: 2 starting from position 1057, 1058, 1059, 1060, 1061 or 1062 and ending at a position between 1170 and 1204 inclusive, preferably position 1187; or (ii) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 114 and ending at a position selected from position 1500, 1501, 1502, 1503, 1504, 1505, 1506, 1507, 1508, 1509 and 1510; or (iii) App of *N. meningitidis* MC58 shown in SEQ ID NO: 2 starting from position 1057, 1058, 1059, 1060, 1061 or 1062 and ending at a position 1220, 1221, 1222, 1223, 1224, 1225 and 1226, preferably position 1224; or (iv) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 114 and ending at a position selected from position 1580, 1581, 1582, 1583, 1584, 1585, 1586, 1587, and 1588, preferably 1584.

In some embodiments, the fusion polypeptide has first and second amino acid sequences, the C-terminus of the first sequence being fused to the N-terminus of the second sequence, wherein the first sequence has at least 90% identity with the amino acid sequence of the IgA1P of *N. meningitidis* MC58 shown in SEQ ID NO: 1 starting from position 27, 28, 29, 30, 31 or 32 and ending at position 960, 961, 962, 963, 964, 965, 966, 967, 968, 969, 9701, 971, 972, 973, 974, 975, 976, 977, 978, 979 or 980; and wherein the second sequence has at least 90% identity with the amino acid sequence of (i) App of *N. meningitidis* MC58 shown in SEQ ID NO: 2 starting from position 1057, 1058, 1059, 1060, 1061 or 1062 and ending at a position between 1170 and 1204 inclusive, preferably position 1187; or (ii) AusI of *N. meningitidis* MC58 shown in SEQ ID NO: 3 starting from position 969, 970, 971, 972, 973, 974, 975, 976, 977, 978, 979 or 980 and ending at a position between 1131 and 1177 inclusive, preferably position 1161; or (iii) App of *N. meningitidis* MC58 shown in SEQ ID NO: 2 starting from position 1057, 1058, 1059, 1060, 1061 or 1062 and ending at a position 1220, 1221, 1222, 1223, 1224, 1225 and 1226, preferably position 1224; or (iv) AusI of *N. meningitidis* MC58 shown in SEQ ID NO: 3 starting from position 969, 970, 971, 972, 973, 974, 975, 976, 977, 978, 979 or 980 and ending at a position 1195, 1196, 1197, 1198, 1199, 1200, 1201, preferably position 1198.

In some embodiments, the fusion polypeptide has first and second amino acid sequences, the C-terminus of the first sequence being fused to the N-terminus of the second sequence, wherein the first sequence has at least 90% identity with the amino acid sequence of the App of *N. meningitidis* MC58 shown in SEQ ID NO: 2 starting from position 40, 41, 43, 44, 45 or 46 and ending at position 950, 951, 952, 953, 954, 956, 957, 958, 959 or 960; and wherein the second sequence has at least 90% identity with the amino acid sequence of (i) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 114 and ending at a position selected from position 1500, 1501, 1502, 1503, 1504, 1505, 1506, 1507, 1508, 1509 and 1510; or (ii) AusI of *N. meningitidis* MC58 shown in SEQ ID NO: 3 starting from position 969, 970, 971, 972, 973, 974, 975, 976, 977, 978, 979 or 980 and ending at a position between 1131 and 1177 inclusive, preferably position 1161.

(iii) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 114 and ending at a position selected from position 1580, 1581, 1582, 1583, 1584, 1585, 1586, 1587, and 1588, preferably 1584; or (iv) AusI of *N. meningitidis* MC58 shown in SEQ ID NO: 3 starting from position 969, 970, 971, 972, 973, 974, 975, 976, 977, 978, 979 or 980 and ending at a position 1195, 1196, 1197, 1198, 1199, 1200, 1201, preferably position 1198.

In some embodiments, the fusion polypeptide has first and second amino acid sequences, the C-terminus of the first sequence being fused to the N-terminus of the second sequence, wherein the first sequence has at least 90% identity with the amino acid sequence of the AusI of *N. meningitidis* MC58 shown in SEQ ID NO: 3 starting from position 26, 27, 28, 29, 30 or 31 and ending at position 860, 861, 862, 863, 864, 865, 866, 867, 868, 869, 870, 871, 872 or 873; and wherein the second sequence has at least 90% identity with the amino acid sequence of (i) App of *N. meningitidis* MC58 shown in SEQ ID NO: 2 starting from position 1057, 1058, 1059, 1060, 1061 or 1062 and ending at position 1170-1204, preferably position 1187; or (ii) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 114 and ending at a position selected from position 1500, 1501, 1502, 1503, 1504, 1505, 1506, 1507, 1508, 1509 and 1510; or (iii) App of *N. meningitidis* MC58 shown in SEQ ID NO: 2 starting from position 1057, 1058, 1059, 1060, 1061 or 1062 and ending at a position 1220, 1221, 1222, 1223, 1224, 1225 and 1226, preferably 1224; or (iv) IgA1P of *N. meningitidis* MC58 shown in SEQ ID NO: 1 starting from position 1000, 1001, 1002, 1003, 1004, 1005, 1006, 1007, 1008, 1009, 1110, 1111, 1112, 1113 or 114 and ending at a position selected from position 1580, 1581, 1582, 1583, 1584, 1585, 1586, 1587, and 1588, preferably 1584

'At least 90% identity' naturally encompasses at least 91, 92, 93, 94, 95, 96, 97, 98, 99 and/or 100% identity.

The "fusion polypeptides" in accordance with the invention, in particular as described above may further comprise a mutation in the catalytic site as previously described to reduce or suppress the catalytic activity. The mutation may in particular intervene at the Serine position, which may, for instance, be replaced with a Valine.

Subtilisin-Like Serine Protease Auto-Transporter Antigen of *N. Meningitidis*: NalP WO 00/26375 relates to several virulence factors of *N. meningitidis* for use as a vaccinal agent. One of these factors is the outer membrane protein ORF047 of *N. meningitidis* strain ATCC13090 of serogroup B, also designated under the reference NMB1969 (Tettelin et al., Science (March 2000) 287: 1809). This protein has been further identified as an auto-transporter lipoprotein with subtilisin-like serine protease activity, by Turner et al., Infect. Immun. (2002) 70: 4447 and originally called AusP or AspA for "auto-transported serine protease A". Later on, in van Ulsen et al., Mol. Microbiol. (2003) 50 (3): 1017, this protein was called NalP for "*N. meningitidis* auto-transporter lipoprotease". The nalP gene has been shown to be subject to phase variation.

Although the terms "ORF047", "NMB1969", "AspA" and "NalP" may be used interchangeably, the term "NalP" has been selected for further use hereinafter.

Like all auto-transporters, NalP is produced as a precursor of about 112 kDa, comprising a cleavable signal peptide, a N-terminal passenger domain and a C-terminal, outer-membrane-based beta-domain, this latter comprising in sequence, a N-terminal translocator domain, an alpha-domain helix and a C-terminal beta-core composed of 12 beta-sheets. The precursor is transported to the outer membrane and the C-terminal domain remains surface-exposed while the N-ter passenger domain of about 70 kDa is processed and secreted (released into the bacterial environment) upon auto-cleavage due to the subtilisin-like serine protease activity of NalP. van Ulsen et al., Mol. Microbiol. (2003) 50 (3): 1017 has additionally shown that the lipidated form is an intermediate in the secretion process as the secreted 70 kDa form is not lipidated.

The domain structure of NalP is further described in Table 3 below by reference to NalP of strain MC58: SEQ ID NO: 4; numbering starts in amino acid position 1 with the Met initiation codon, followed by the peptide leader sequence; the mature protein being considered to start with the Cysteine residue in position 28. The N-terminal passenger domain of NalP is responsible for the subtilisin-like serine protease activity. The serine protease catalytic site is constituted by a triad [Asp/His/Ser respectively at positions 138, 157 and 426 in NalP of strain MC58]. The twelve beta-sheets in the form of a barrel constitute a hydrophilic pore filled by the alpha-domain in the form of an alpha-helix.

TABLE 3

Domain structure of *N. meningitidis* MC58 NalP (NMB1969)

| | | | NalP N-terminal domain = | NalP C-terminal domain = β domain | | |
|---|---|---|---|---|---|---|
| Catalytic triad | Signal sequence | Passenger domain = Protease domain | Translocator domain | α-peptide | β core = 12 β-sheets |
| 138D 157H 426S | 1-27 | 28-774 | 775-784 | 785-809 | 810-1082 |

It shall be understood that the domain definitions by reference to amino acid positions may vary slightly as it is not always possible to precisely define a domain to the exact amino acid. For example, the domains may be defined slightly differently by different workers or they may be defined differently in different strains of *N. meningitidis*. Thus, said domains may be defined according to the locations given herein, or according to said locations +/−1, 2, 3, 4, 5, 6, 7, 8, 9, 10 or more amino acids, i.e. 1, 2, 3, 4, 5, 6, 7, 8, 9, 10 or more amino acids N-terminal or C-terminal of said locations.

The same holds true for the location of the twelve beta-sheets of strain MC58 beta-core; however it is indicated that they are located approximately as follows:

1st β-sheet L817-E831; 2nd β-sheet E836-G853; 3rd 1-sheet T856-E871; 4th β-sheet A874-A891; 5th β-sheet G895-S913; 6th β-sheet H919-V937; 7th β-sheet D946-Q960; 8th β-sheet L977-P993; 9th β-sheet A998-D1009; 10th β-sheet T1039-G1052; 11th β-sheet W1055-S1066; 12th β-sheet Y1069-F1082.

The sequences of the nalP gene (ORF047) and NalP protein thereof were initially described in patent application WO 00/26375 (Sanofi Pasteur/INSERM). Full-length sequences were identified by analysis of the genome sequence of *N. meningitidis* serogroup B strain ATCC 13090, available in the database Pathoseq® of Incyte Pharmaceuticals.

nalP gene and NalP protein sequences of *N. meningitidis* strains MC58 (serogroup B), Z2491 (serogroup A) and FAM18 (serogroup C) are respectively disclosed in Tettelin et al., Science, March 2000, 287: 1809 or WO 00/66791; Parkhill et al., Nature (March 2000) 404: 502; and Bentley et al., PLoS Genet., 3, e23 (2007). MC58 NalP is also designated as NMB1969 and sequences thereof are available under accession number NP_003112 (version NP as submitted on Mar. 17, 2000). Z2491 NalP is also designated as NMA0478. FAM18 NalP is also designated as NMC1943.

For use in the present invention, the NalP antigen may be a NalP polypeptide comprising or essentially consisting of:

(A) a full-length mature *N. meningitidis* NalP protein; or (B) a fragment of a full-length mature *N. meningitidis* NalP protein (NalP fragment), which full-length mature *N. meningitidis* NalP protein comprises (a) a passenger domain comprising a subtilisin-like serine protease triad (Asp/His/Ser) and (b) a beta-domain comprising a translocator domain, an alpha-peptide and a beta-core composed of twelve beta-sheets; said NalP fragment comprising:
  (i) at the N-terminus, the NalP passenger domain;
  (ii) at the C-terminus, the beta-domain comprising the translocator domain, the alpha-peptide and at least one and no more than eleven NalP beta-sheets;

wherein said polypeptide does not comprise a full-length mature *N. meningitidis* NalP protein or (C) a mutant of said full-length mature *N. meningitidis* NalP protein (A) or said NalP fragment (B) which lacks or has reduced subtilisin-like serine protease activity and/or does not contain any cleavage site able to be cleaved by a subtilisin-like serine protease.

By "full-length mature NalP" is meant the NalP protein lacking the NalP signal peptide.

Accordingly, by "full-length mature NalP" is meant the full-length mature NalP comprising (having) (i) a naturally-occurring full-length mature amino acid sequence or (ii) a naturally-occurring full-length mature amino acid sequence lacking at most the first 50 N-terminus amino acids and/or at most the last 20 C-terminus amino acids or (iii) a naturally-occurring full-length mature amino acid sequence fused to the 1, 2 or 3 amino acids of the C-terminus of the signal sequence.

Advantageously, the full-length mature NalP is not lipidated. To that end, the full-length mature NalP may lack at least the cysteine residue in position 1 of the mature form (position 28, by reference to SEQ ID NO: 4).

An example of a useful full-length mature NalP protein is the full-length mature NalP protein of strain MC58. Accordingly, this MC58 NalP protein comprises (has) the amino acid sequence shown in SEQ ID NO: 4, starting with the amino acid in position 28, 29 or 30, preferably 29 or 30, and ending with the amino acid in position 1082. Other useful MC58 NalP proteins comprise (have) the amino acid sequence shown in SEQ ID NO: 4, starting with the amino acid in any one of the positions 28 to 78, preferably 28 to 58, more preferably 28 to 38, most preferably in position 28, 29 or 30, and ending with the amino acid in any one of the positions 1070 to 1082.

Other useful full-length mature NalP proteins include variants of MC58 NalP protein which may be described by reference to the MC58 amino acid sequence reported in SEQ ID NO: 4. These variants comprise (have) an amino acid sequence starting with an amino acid corresponding to the amino acid in position 28, 29 or 30, preferably 29 or 30, and ending with an amino acid corresponding to the amino acid in position 1082. Other useful variants of the MC58 NalP protein, still described by reference to the MC58 amino acid sequence reported in SEQ ID NO: 4, comprise (have) an amino acid sequence starting with an amino acid corresponding to the amino acid in any one of the positions 28 to 78, preferably 28 to 58, more preferably 28 to 38, and ending with an amino acid corresponding to the amino acid in any one of positions 1070 to 1082.

NalP is a protein with low solubility due to the presence of the beta-core and accordingly, recombinant expression and purification of full-length NalP may be difficult to achieve. This is the reason why, in a preferred embodiment, the NalP antigen may be produced as a truncated NalP, at least partially lacking the beta-core.

Accordingly, for use in the present invention, the NalP antigen may also be a NalP polypeptide comprising:

(1) a fragment of a full-length mature *N. meningitidis* NalP protein (NalP fragment), which full-length mature *N. meningitidis* NalP protein comprises (a) a passenger domain comprising a subtilisin-like serine protease triad (Asp/His/Ser) and (b) a beta-domain comprising a translocator domain, an alpha-peptide and a beta-core composed of twelve beta-sheets; said NalP fragment comprising:
  (i) at the N-terminus, the NalP passenger domain;
  (ii) at the C-terminus, the beta-domain comprising the translocator domain, the alpha-peptide and at least one and no more than eleven NalP beta-sheets;

wherein said polypeptide does not comprise a full-length mature *N. meningitidis* NalP protein or (2) a mutant of said NalP fragment which lacks or has reduced subtilisin-like serine protease activity and/or does not contain any cleavage site able to be cleaved by a subtilisin-like serine protease.

The term "fragment" of a reference sequence refers to a chain of contiguous nucleotides or amino acids that is shorter than the reference sequence.

Advantageously, the NalP polypeptide is the NalP fragment or the mutant of the NalP fragment, as described.

Although the mutated NalP for use in the composition of the invention and polypeptides of the present invention are more particularly exemplified herein by reference to the amino acid sequence of MC58 NalP protein (that naturally-occurs in *N. meningitidis* strain MC58), polypeptides of any naturally-occurring/allelic variant of *N. meningitidis* strain M982/B16B6/MC58 are also encompassed within the scope invention as well as any variant that may result from genetic engineering. By extension, the term variant is therefore applied to amino acid sequences, proteins or fragments thereof other than MC58 sequences, proteins or fragments thereof. Variations in amino acid sequence may be introduced by substitution, deletion or insertion of one or more codons into the nucleic acid sequence encoding the protein that results in a change in the amino acid sequence of the protein without substantially affecting the tri-dimensional structure and/or the biological and/or immunogenic properties. Typically, the variation may result for an amino acid substitution that may be conservative or non-conservative, preferably conservative. A conservative substitution is an amino acid substitution in which an amino acid is substituted for another amino acid with similar structural and/or chemical properties.

In what follows, variants and/or mutants are described by reference to the amino acid sequence of reference (SEQ ID NO: 4). Such a description by reference is based on the prerequisite of optimal sequence alignment in order to determine the amino acid in the variant sequence that corresponds to the amino acid defined as being in a specific position in the amino acid of reference.

The NalP passenger domain at the N-terminus of the NalP fragment may be the MC58 NalP passenger domain comprising (having) the amino acid sequence starting in position 28, 29 or 30 or in any one of position 28 to 78, preferably 28 to 58, more preferably 28 to 38, and ending in position 774 in SEQ ID NO: 4. It may also be a variant of the MC58 NalP passenger domain comprising (having) an amino acid sequence described by reference to the MC58 amino acid sequence reported in SEQ ID NO: 4, starting with an amino acid corresponding to the amino acid in position 28, 29 or 30 or in any one of the positions 28 to 78, preferably 28 to 58, more preferably 28 to 38, and ending with an amino acid corresponding to the amino acid in position 774. Preferably, an NalP passenger domain described above may start at position 29.

Advantageously, the NalP fragment comprises at the C-terminus at least one and no more than eight, six, four, or preferably two NalP beta sheets. In some embodiments, the NalP fragment comprises (i) the first beta-sheet; (ii) first and second beta-sheets; (iii) first, second and third beta-sheets; (iv) first, second, third and fourth beta-sheets; (v) first, second, third, fourth and fifth beta-sheets; (vi) first, second, third, fourth, fifth and sixth beta-sheets; (vii) first, second, third, fourth, fifth, sixth and seventh beta-sheets; or (viii) first, second, third, fourth, fifth, sixth, seventh, and eighth beta-sheets.

As a matter of example, a useful NalP fragment is the MC58 NalP fragment comprising at the C-terminus, two beta-sheets comprising (having) the amino acid sequence starting in any one of positions 815 to 820, e.g. in position 817 and ending in any one of positions 850 to 855, e.g. in position 853. Still as a matter of example, a useful NalP fragment is a variant of the MC58 NalP fragment comprising two beta-sheets comprising (having) an amino acid sequence described by reference to the MC58 amino acid sequence reported in SEQ ID NO: 4, starting with an amino acid corresponding to the amino acid in any one of the positions 815 to 820, e.g. in position 817, and ending with an amino acid corresponding to the amino acid in any one of positions 850 to 855, e.g. in position 853.

For use in the present invention, the NalP fragment advantageously comprises a C-ter truncated NalP C-terminal domain including the translocator domain, the alpha-peptide and as described above, at least one and no more than eleven NalP beta-sheets.

An example of a useful NalP fragment is a fragment of the full-length mature NalP protein of strain MC58. Accordingly, this MC58 NalP fragment comprises (has) the amino acid sequence shown in SEQ ID NO: 4, starting with the amino acid in position 28, 29 or 30 and ending with the amino acid in position 853. Other useful MC58 NalP fragments comprise (have) the amino acid sequence shown in SEQ ID NO: 4, starting with the amino acid in position 28, 29 or 30 or in any one of the positions 28 to 78, preferably 28 to 58, more preferably 28 to 38, and ending with the amino acid in any one of positions 840 to 860, preferably 850 to 855.

Other useful NalP fragments include variants of MC58 NalP fragments which may be described by reference to the MC58 amino acid sequence reported in SEQ ID NO: 4. These variants comprise (have) an amino acid sequence starting with an amino acid corresponding to the amino acid in position 28, 29 or 30 and ending with an amino acid corresponding to the amino acid in position 853. Other useful variants of the MC58 NalP fragment, still described by reference to the MC58 amino acid sequence reported in SEQ ID NO: 4, comprise (have) an amino acid sequence starting with an amino acid corresponding to the amino acid in position 28, 29 or 30 or in any one of the positions 28 to 78, preferably 28 to 58, more preferably 28 to 38, and ending with an amino acid corresponding to the amino acid in any one of positions 840 to 860, preferably 850 to 855.

As already mentioned above, in some embodiments, the full-length mature NalP protein or the NalP fragment is mutated so that it lacks or has reduced subtilisin-like serine protease activity and/or does not contain any cleavage site susceptible/able to be cleaved by a subtilisin-like serine protease i.a., NalP. As a result of the mutation, NalP remains in a precursor state, the N-terminal passenger domain not being cleaved from the C-terminal domain. For example, protease activity may be reduced by 10, 20, 30, 40, 50, 60, 70, 80, 90, 95, 96, 97, 98, 99 or 100% compared to the wild type sequence. Protease activity may be evaluated by assaying the ability to cleave auto-transporter proteins, for example by Western Blot as described in for example Roussel-Jazédé et al., Infect Immun. (2010) 78 (7): 3083; van Ulsen P, et al., Mol Microbiol. (November 2003) (3): 1017 and Serruto et al., PNAS February 2010 107 (8): 3770.

Preferably, the full-length mature NalP protein or the NalP fragment lacks subtilisin-like serine protease activity. In order to reduce or abolish the serine protease activity, any of the amino acids present in the catalytic triad may be mutated, advantageously by amino acid substitution. In a particular embodiment, one way to achieve that goal may be to substitute the Serine residue in the catalytic triad by any other amino acid, advantageously by Glycine, Threonine, Valine, Leucine, Isoleucine or Alanine, preferably by Valine or Alanine, and more preferably by Alanine.

The catalytic triad of MC58 NalP is composed of Asp138, His157 and Ser426 in SEQ ID NO: 4. Accordingly, the catalytic triad of variant of MC58 NalP is composed of amino acids corresponding to Asp138, His157 and Ser426 in the amino acid sequence of SEQ ID NO: 4; and accordingly, the mutation occurs at the position corresponding to Asp138, His157 or Ser426 of the amino acid sequence of SEQ ID NO: 4.

Examples of useful mutated full-length mature NalP protein include in particular any one of the MC58 NalP full-length mature NalP protein or variants thereof as described above, each being mutated so that it lacks or has reduced subtilisin-like serine protease activity and/or does not contain any cleavage site susceptible/able to be cleaved by a subtilisin-like serine protease.

Examples of useful mutated NalP fragment include in particular any one of the MC58 NalP fragments or variants thereof as described above, each being mutated so that it lacks or has reduced subtilisin-like serine protease activity and/or does not contain any cleavage site susceptible/able to be cleaved by a subtilisin-like serine protease.

According to a preferred embodiment, an isolated polypeptide according to the invention may be a polypeptide lacking protease activity, and wherein the NalP passenger domain portion of said polypeptide has an amino acid substitution at the position corresponding to Asp138, His157 or Ser426 of the amino acid sequence of SEQ ID NO:1.

According to a preferred embodiment, an isolated polypeptide according to the invention may be a polypeptide wherein the residue corresponding to Ser426 of SEQ ID NO: 1 is substituted by Ala.

According to a preferred embodiment, an isolated polypeptide according to the invention may be a NalP fragment comprising no more than two NalP beta sheets.

As a matter of non-limiting illustration, particular examples include:

The S426A mutated MC58 NalP protein which comprises (has) the amino acid sequence shown in SEQ ID NO: 4, starting with the amino acid in position 29 or 30 and ending with the amino acid in position 1082; and in which Serine 426 is substituted by Alanine.

A mutated variant of the S426A MC58 NalP protein which may be described as follows by reference to the MC58 amino acid sequence reported in SEQ ID NO: 4. This variant comprises (has) an amino acid sequence starting with an amino acid corresponding to the amino acid in position 29 or 30 and ending with an amino acid corresponding to the amino acid in position 1082 and in which the amino acid corresponding to the Serine 426 is substituted by Alanine.

The S426A mutated MC58 NalP fragment which comprises (has) the amino acid sequence shown in SEQ ID NO: 4, starting with the amino acid in position 29 or 30 and ending with the amino acid in position 853; and in which Serine 426 is substituted by Alanine; and, A mutated variant of the S426A MC58 NalP fragment which may be described as follows by reference to the MC58 amino acid sequence reported in SEQ ID NO: 4. This variant comprises (has) an amino acid sequence starting with an amino acid corresponding to the amino acid in position 28, 29 or 30 and ending with an amino acid corresponding to the amino acid in position 853 and in which the amino acid corresponding to the Serine 426 is substituted by Alanine.

In some embodiments, a NalP antigen may be a polypeptide comprising or consisting of a NalP fragment which essentially consists of the passenger domain, the translocator domain, the alpha-peptide and the first and second beta-sheets; wherein the Ser residue of the catalytic triad in the NalP passenger domain is optionally mutated by substitution.

According to a preferred embodiment, an isolated polypeptide according to the invention may be a fragment of full-length mature NalP protein of *N. meningitidis* MC58 or of a NalP variant having at least 95% identity with the NalP protein of *N. meningitidis* MC58.

In an embodiment, said NalP fragment comprises an amino acid sequence which has at least 95%, 96%, 97%, 98%, 99% or 100% amino acid sequence identity with the amino acid sequence of SEQ ID NO: 7.

According to a preferred embodiment, an isolated polypeptide according to the invention may be NalP fragment comprising the amino acid sequence of SEQ ID NO: 7.

In other words, a NalP antigen may be a polypeptide comprising or being:

A full-length mature MC58 NalP protein or a variant thereof, each of the protein or the variant thereof being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 4, starting with the amino acid in position 28 and ending with amino acid in position 1082.

A MC58 NalP fragment or a variant thereof, each of the fragment or the variant thereof being optionally mutated as described above, which comprises (has) an amino acid sequence having at least 80%, 85%, 90%, 95%, 96%, 97%, 98%, 99% or 100% identity with the MC58 amino acid sequence reported in SEQ ID NO: 4, starting with the amino acid in position 28, 29 or 30 and ending with amino acid in position 853.

TbpB of *N. meningitidis*

The human transferrin receptor of *N. meningitidis* is an outer-membrane complex composed of two subunits: the human transferrin-binding protein A (TbpA, also called Tbp1) and the human transferrin-binding protein B (TbpB also called Tbp2).

Two major human transferrin-binding protein B (TbpB) families have to date been documented in *N. meningitidis*, defining two isotypes within the species: strains of TbpB of isotype I are characterized by a tbpB gene of 1.8 kb, and those of isotype II are characterized by a tbpB gene of 2.1 kb. Herein after the term "isotype" is indifferently applied to the TbpB antigen and to the strain expressing the specific TbpB antigen. Strains of isotype I are essentially found within the ST-11 clonal complex, and those of isotype II, are spread over i.a. the ST-8, ST-18, ST-32 and ST-41/44 clonal complexes (Harrison et al., BMC Microbiol. 2008, 8: 66). The B16B6 (serogroup B) and FAM18 (serogroup C) strains are representatives of isotype I; the MC58, M982, BZ83 and 8680 serogroup B strains are representatives of isotype II.

A TbpB antigen of *N. meningitidis* is defined as being an antigen able to be recognized in an immunoassay (e.g., Western Blot) by an antiserum raised in a mammal against a purified full-length TbpB of *N. meningitidis* of either isotypes. For use in the present invention, it may be i.a., a full-length TbpB or an immunogenic fragment thereof; a full-length TbpB or a fragment thereof comprising the site for binding to human transferrin (hTf), which bears a mutation in the binding site so that it is unable to bind to hTf (Renauld-Mongenie et al., J. Bacteriol. (2004) 186 (3): 850); or TbpB chimeras such as the fusion product between (i) a first TbpB of a first strain or an immunogenic fragment thereof and (ii) a second TbpB of a second strain or an immunogenic fragment thereof; or a fusion product between a TbpB or an immunogenic fragment thereof and another protein of *N. meningitidis*.

Although for the purposes of the invention, a TbpB antigen of any isotype can be used without distinction, it is preferred to use at least a TbpB antigen of isotype II.

Still preferably, the composition of the invention may comprise both a TbpB antigen of isotype II and a TbpB antigen of isotype I.

The TbpB of *N. meningitidis*, as naturally produced by *N. meningitidis*, is a lipoprotein. For use in the composition of the invention, the TbpB antigen can be lipidated or not. Accordingly, the immunogenic or vaccinal composition/combination may comprise:
(i) a non-lipidated TbpB isotype II antigen;
(ii) a non-lipidated TbpB isotype II antigen and a lipidated TbpB isotype I antigen;
(iii) a lipidated TbpB isotype II antigen and a lipidated TbpB isotype I antigen;
(iv) a non-lipidated TbpB isotype II antigen and a non-lipidated TbpB isotype I antigen;
(v) a lipidated TbpB isotype II antigen and a non-lipidated TbpB isotype I antigen;
(vi) a non-lipidated TbpB isotype I antigen;
(vii) a lipidated TbpB isotype II antigen; or
(viii) a lipidated TbpB isotype I antigen.

According to an advantageous embodiment, when the immunogenic or vaccinal composition/combination comprises at least one TbpB antigen, this TbpB antigen is of isotype II antigen.

The open reading frame (ORF) or tbpB gene encoding the TbpB antigen of several strains of $N.$ $meningitidis$, and the amino acid sequence of the corresponding protein, are already known. For instance, the tbpB and TbpB precursor sequences of the $N.$ $meningitidis$ strains M982 (isotype II) and B16B6 (isotype I), were disclosed in Legrain et al., Gene (1993) 130 (1): 73. The amino acid sequence of TbpB of strain M982 is shown in SEQ ID NO: 5. The amino acid sequence of TbpB of strain B16B6 is shown in SEQ ID NO: 6 [as well as in patent EP 586 266, respectively designated under the names "Tbp2-2169" (Seq Id No 7-8 in EP 586 266) and "Tbp2-2394" (Seq Id No 1-2 in EP 586 266)]. M982 and B16B6 TbpB sequences (amino acid and nucleotides sequences) may be retrieved from the NCBI website, under the respective Genbank accession numbers Z15130.1 and Z15129.1. Those web pages refer to Tbp2, the previous term for TbpB. Both M982 and B16B6 TbpB sequences include a signal peptide from position 1 to 20, the mature form starting in position 21 with a Cysteine residue which is the residue onto which the lipid chain is attached, upon lipidation; which Cysteine residue is omitted when TbpB is recombinantly produced in a non-lipidated form.

Within the $N.$ $meningitidis$ species and even strain isotypes, the amino acid sequence of TbpB proteins may display a certain degree of variability from one strain to another, without this affecting the biological function. This is then referred to as an "allelic variant" to a protein of a specific (reference) strain, with an identical function.

Thus, it will be easily understood that the present invention is not limited to the use of a TbpB defined by a particular amino acid sequence. Although any reference to an amino acid sequence is made by way of non-limiting illustration, it is indicated that TbpB protein of isotype II or I may exhibit an amino acid sequence which shows at least 80%, 85%, 90%, 95% 96%, 97%, 98%, 99% or 100% identity with the amino acid sequence of respectively:
mature TbpB M982 shown in SEQ ID NO: 5, starting with the amino acid in position 21 and ending with amino acid in position 711, the percent identity being calculated upon local or global alignment; or
mature TbpB B16B6 shown in SEQ ID NO: 6, starting with the amino acid in position 21 and ending with amino acid in position 599, the percent identity being calculated upon local or global alignment.

In other words, it is indicated that for use in the present invention a TbpB antigen may be a polypeptide comprising or consisting of:

A full-length mature TbpB protein or a fragment thereof, which comprises (has) an amino acid sequence having at least 80%, 85%, 90%, 95%, 96%, 97%, 98%, 99% or 100% identity with the M982 amino acid sequence reported in SEQ ID NO: 5, starting with the amino acid in position 21 and ending with amino acid in position 711, the percent identity being calculated upon global or local alignment.

A full-length mature TbpB protein or a fragment thereof, which comprises (has) an amino acid sequence having at least 80%, 85%, 90%, 95%, 96%, 97%, 98%, 99% or 100% identity with the B16B6 amino acid sequence reported in SEQ ID NO: 6, starting with the amino acid in position 21 and ending with amino acid in position 599, the percent identity being calculated upon global or local alignment.

Preferably, the $N.$ $meningitidis$ TbpB isotype II antigen is a TbpB antigen of strain M982. Preferably also, the $N.$ $meningitidis$ TbpB isotype I antigen is a TbpB antigen of strain B16B6.

It is also indicated that annotated genome sequences of the meningococcal strains MC58 (serogroup B), Z2491 (serogroup A) and FAM18 (serogroup C) are respectively disclosed in Tettelin et al., Science, March 2000, 287: 1809 or WO 00/66791; Parkhill et al., Nature (March 2000) 404: 502; and Bentley et al., PLoS Genet., 3, e23 (2007). The tbpB/TbpB sequences of the MC58 strain disclosed in Tettelin et al. (above) or WO 00/66791 are designated under the reference number NMB0460; they are also available under accession number NP_273507 (version NP_273507.1 as submitted on Mar. 17, 2000).

The TbpB antigen, either lipidated or non-lipidated, may be recombinantly produced as a full-length protein. When the TbpB antigen is produced as a non-lipidated full-length protein, the cysteine residue in position 21 (position 1 at the N-terminal end of the mature form) may be absent.

When the TbpB antigen is produced as a lipidated full-length protein, for use in the present invention, it may conveniently be incorporated into liposomes, preferably cationic liposomes, optionally together with an $N.$ $meningitidis$ lipooligosaccharide (LOS) as described in WO 10/130896. A preferred LOS is described in WO 10/130898.

The TbpB antigen may be also produced as a truncated protein. Indeed, It has been already shown that the N-ter TbpB fragment and the C-ter TbpB fragment are each able to induce serum bactericidal activity (Rokbi et al., Infect. Immun. (2000) 68 (9): 4938). For use in the present invention, an example of an N-ter fragment of M982 TbpB has an amino acid sequence starting with the cysteine residue in position 21 or the leucine residue in position 22 and ends with the glutamic acid residue in position 371. An example of a C-ter fragment of M982 TbpB has an amino acid sequence starting with the asparagine residue in position 372 and ends with the glutamine residue in position 711. A truncated TbpB protein used in the present invention as the TbpB antigen is preferably a C-ter TbpB fragment.

Unless otherwise indicated, all the antigens/polypeptides/fragments I constructs/amino acid sequences are described throughout the specification from the N-terminus end to the C-terminus end. As a matter of example, a fragment described as consisting of the protease domain, the α-peptide domain and part of the beta-domain of the trypsin-like serine protease auto-transporter of $N.$ $meningitidis$ shall be understood as a fragment consisting of, from N-ter to C-ter, the protease domain, the α-peptide domain and part of the beta-domain, the C-ter of the protease domain being fused to the N-ter of the α-peptide domain, the C-ter of which being fused to the N-ter of 'part of the beta-domain'. Fusion is conveniently achieved by covalent peptidic bound (amide linkage CO—NH).

Any of the antigens for use in the composition according to the invention may be synthetized by any method well-known from the skilled person. Such methods include biological production methods by recombinant technology and means. In particular, nucleotide sequences encoding the *N. meningitidis* proteins and corresponding amino acid sequences thereof may be retrieved from a number of bioinformatics websites such as the site of the European Bioinformatics Institute or the National Center for Biotechnology Information (US). Any desired encoding sequences may be conceived and designed by bioinformatics according to methods and software known in the art, such as the software pack Vector NTI of Invitrogen; chemically synthetized de novo; and finally cloned into expression vectors available in the art. Methods of purification that can be used are also well-known from the skilled person.

In the context of the invention the term "about" as used herein when referring to a measurable value, such as an amount, duration or a number, such as the number of amino acids in an amino acid sequence, is meant to encompass variations of ±5%.

In the context of the invention the term "a" or "an" entity refers to one or more of that entity. For example "a polynucleotide", "an isolated peptide", "a fusion peptide", "an isolated polynucleotide" is understood to represent respectively at least one or more "polynucleotide", at least one or more "isolated peptide", at least one or more "fusion peptide", at least one or more "isolated polynucleotide".

In the context of the invention and throughout the specification, the terms such as "comprising", "having", "including" and "containing" are to be construed as open-ended terms (i.e., meaning "including, but not limited to,") unless otherwise noted. All reference to "comprising" or "having" also includes the embodiments "essentially consisting of", "consisting of" and "being". Terms such as the embodiments "essentially consisting of", "consisting of" and "being" have the meaning ascribed to them in most patent jurisdictions, preferably in the jurisdiction in question; e.g., they imply the exclusion of all, most or all but a negligible amount of other elements, or they allow for elements not explicitly recited, but exclude elements that are found in the prior art or that affect a basic or novel property.

Compositions

In a first embodiment, a composition of the invention may comprise at least two *Neisseria meningitidis* antigens selected from the group consisting of a trypsin-like serine protease auto-transporter antigen, a NalP antigen and a TbpB antigen, said antigens being as-above described.

According to one embodiment, a composition in accordance with the invention may comprise (i) a trypsin-like serine protease auto-transporter antigen and (ii) an NalP antigen and/or TbpB antigen.

Preferably, a TbpB antigen may be of isotype II.

More preferably, a composition comprising a TbpB antigen of isotype II may further comprise a TbpB antigen of isotype I.

According to one embodiment, a composition in accordance with the invention may comprise an additional *N. meningitidis* protein antigen.

According to one embodiment, a composition in accordance with the invention may be a bivalent composition comprising a trypsin-like serine protease auto-transporter antigen and an NalP antigen.

According to one embodiment, a composition in accordance with the invention may be a bivalent composition comprising a trypsin-like serine protease auto-transporter antigen and a TbpB antigen.

According to one embodiment, a composition in accordance with the invention may be a trivalent composition comprising (i) a trypsin-like serine protease auto-transporter antigen, (ii) an NalP antigen and (iii) a TbpB antigen.

According to one embodiment, a composition in accordance with the invention may be a trivalent composition comprising (i) a trypsin-like serine protease auto-transporter antigen, (ii) a TbpB antigen of isotype II and (iii) a TbpB antigen of isotype I.

According to one embodiment, a composition in accordance with the invention may be a quadrivalent composition comprising (i) an IgA1P antigen, (ii) an NalP antigen, (iii) a TbpB antigen of isotype II and (iv) a TbpB antigen of isotype I.

Preferably, the TbpB antigen of isotype II is the TbpB of strain M982.

Also preferably, the TbpB antigen of isotype I is the TbpB of strain B16B6.

In some embodiments the TbpB of isotype I is lipidated.

Preferably, an NalP antigen is of strain MC58. More preferably, an NalP antigen comprises the amino acid sequence SEQ ID NO:7.

According to one embodiment, a trypsin-like serine protease auto-transporter antigen of the composition of the invention may be the IgA1P antigen.

Preferably, an IgA1P antigen may be of strain MC58. More preferably, an IgAIP antigen may comprise an amino acid sequence selected from SEQ ID NO: 8, SEQ ID NO: 9 and SEQ ID NO: 10.

In some embodiments, a composition in accordance with the invention may further comprise a *N. meningitidis* LOS.

Preferably, the LOS is detoxified in liposomes.

In some embodiments of the invention, an immunogenic composition may comprise at least two antigens independently selected from:

(I) An IgA1P antigen comprising or consisting of:
  (a) An IgA1P fragment which essentially consists of:
    (i) the IgA1P protease domain in which the Ser residue of the catalytic triad is optionally mutated by substitution with e.g., Valine, the α-peptide domain and at least one and no more than eleven beta-sheets, preferably the first and second beta-sheets; or
    (ii) the IgA1P protease domain in which the Ser residue of the catalytic triad is optionally mutated by substitution with e.g., Valine; or
  (b) An IgA1P-App fusion polypeptide which essentially consists of the IgA1P protease sub-domain in which the Ser residue of the catalytic triad is optionally mutated by substitution with e.g., Valine, fused to the App α-peptide domain;

(II) A TbpB antigen, preferably non-lipidated, preferably of isotype II; and (III) A NalP antigen which comprises or consists of a NalP fragment which essentially consists of the NalP passenger domain, the translocator domain, the alpha-peptide and the first and second beta-sheets; wherein the Ser residue of the catalytic triad in the NalP passenger domain is optionally mutated by substitution with e.g., Alanine.

According to particular embodiments, an immunogenic composition of the invention can be bivalent, trivalent, quadrivalent or pentavalent. In bivalent, trivalent, quadrivalent and pentavalent compositions of the invention, the number of N. meningitidis protein antigens is respectively limited to two, three, four and five.

By «bivalent composition» is meant a composition in which there are only two protein antigens of N. meningitidis. One of these two proteins antigens is a trypsin-like serine protease auto-transporter (trypsine-like SPAT) and the second one can be selected from the group consisting of a NalP antigen and a TbpB antigen. Accordingly, in a bivalent composition of the invention, the N. meningitidis proteins consist of (i) the trypsin-like SPAT and the NalP antigen; or (ii) the trypsin-like SPAT and the TbpB antigen. In this latter alternative, the TbpB antigen is preferably of isotype II.

Examples of bivalent compositions include the following bivalent compositions:
An IgAIP antigen and a TbpB antigen, of isotype I or II, preferably of isotype II;
An App antigen and a TbpB antigen of isotype I or II, preferably of isotype II;
An AusI antigen and a TbpB antigen of isotype I or II, preferably of isotype II;
An IgAIP antigen and a NalP antigen;
An App antigen and a NalP antigen;
An AusI antigen and a NalP antigen; and
A NalP antigen and a TbpB antigen of isotype I or II, preferably of isotype II.

In a particular embodiment, a bivalent composition according to the invention comprises:
(I) An IgA1P antigen which comprises or consists of:
 (a) An IgA1P fragment which essentially consists of:
  (i) the IgA1P protease domain in which the Ser residue of the catalytic triad is optionally mutated by substitution with e.g., Valine, the α-peptide domain and at least one and no more than eleven beta-sheets, preferably the first and second beta-sheets; or
  (ii) the IgA1P protease domain in which the Ser residue of the catalytic triad is optionally mutated by substitution with e.g., Valine; or
 (b) An IgA1P-App fusion polypeptide which essentially consists of the IgAIP protease sub-domain in which the Ser residue of the catalytic triad is optionally mutated by substitution with e.g., Valine, fused to the App α-peptide domain; and
(II) A TbpB antigen, preferably non-lipidated, preferably of isotype II; or
A NalP antigen which comprises or consists of a NalP fragment which essentially consists of the NalP passenger domain, the translocator domain, the alpha-peptide and the first and second beta-sheets; wherein the Ser residue of the catalytic triad in the NalP passenger domain is optionally mutated by substitution with e.g., Alanine.

In another particular embodiment, a bivalent composition according to the invention comprises:
(I) A TbpB antigen, preferably non-lipidated, preferably of isotype II; and
(II) A NalP antigen which comprises a NalP fragment which essentially consists of the NalP passenger domain, the translocator domain, the alpha-peptide and the first and second beta-sheets; wherein the Ser residue of the catalytic triad in the NalP passenger domain is optionally mutated by substitution with e.g., Alanine.

According to a preferred embodiment, a bivalent composition in accordance with the invention may comprise:
an NalP antigen comprising a passenger domain and no more than two beta-sheets, preferably extending from position 30 to position 853 of SEQ ID NO: 4, with possibly more or less 1, 2, 3, 4, or 5 amino acids on each end, and more preferably with a mutation in position 426 (preferably S→A), and
a TbpB antigen, preferably non-lipidated, preferably of isotype II.

According to another preferred embodiment, a bivalent composition in accordance with the invention may comprise:
an IgA1P antigen comprising a passenger domain and no more than two beta sheets, preferably extending from position 28 to position 1584 of SEQ ID NO: 1, with possibly more or less 1, 2, 3, 4, or 5 amino acids on each end, and more preferably with a mutation in position 267 (preferably S→V), and
a TbpB antigen, preferably non-lipidated, preferably of isotype II.

According to another preferred embodiment, a bivalent composition in accordance with the invention may comprise:
an IgA1P antigen comprising a passenger domain and no more than two beta sheets, preferably extending from position 28 to position 1584 of SEQ ID NO: 1, with possibly more or less 1, 2, 3, 4, or 5 amino acids on each end, and more preferably with a mutation in position 267 (preferably S→V), and
an NalP antigen comprising a passenger domain and no more than two beta-sheets, preferably extending from position 30 to position 853 of SEQ ID NO: 4, with possibly more or less 1, 2, 3, 4, or 5 amino acids on each end, and more preferably with a mutation in position 426 (preferably S→A).

By «trivalent composition» is meant a composition in which there are only three protein antigens of N. meningitidis. One of these three proteins antigens is a trypsine-like serine protease auto-transporter (trypsine-like SPAT); the second and the third proteins antigens can be independently selected from the group consisting of a NalP antigen, a TbpB antigen of isotype I and a TbpB antigen of isotype II.

Accordingly, in a trivalent composition of the invention, the N. meningitidis proteins consist of the trypsine-like SPAT, the NalP antigen and the TbpB antigen, this latter being preferably of isotype II. Alternatively, in a trivalent composition of the invention, the N. meningitidis proteins consist of the trypsine-like SPAT, the TbpB antigen of isotype II and the TbpB antigen of isotype serotype I. In a further embodiment, in a trivalent composition of the invention, one of the three protein antigens is the trypsine-like SPAT; the second protein antigen is a NalP antigen or a TbpB antigen, this latter being preferably of isotype II; and the third protein antigen is a N. meningitidis protein antigen which is an additional protein antigen i.e., other than a trypsine-like SPAT, NalP and TbpB antigen.

In a specific embodiment, this additional protein antigen may be the factor H binding protein (fHBP) antigen of N. meningitidis. A fHBP antigen of N. meningitidis is defined as being an antigen able to be recognized in an immunoassay (e.g., Western Blot) by an antiserum raised in a mammal against a purified full-length fHBP of N. meningitidis. For use in the present invention, it may be i.a., a full-length fHBP, lipidated or not, mutated in the fHBP binding site or not, or an immunogenic fragment thereof; or fHBP chimeras such as the fusion product between (i) a first fHBP of a first strain or an immunogenic fragment thereof and (ii) a second fHBP of a second strain or an immunogenic fragment thereof; or a fusion product between a fHBP or an immunogenic fragment thereof and another protein of N. meningitidis.

The fHBP of strain MC58 is designated under the reference NMB1870. Sequences may be retrieved from the National Center for the Biotechnology Information (NCBI) web site at http://www.ncbi.nlm.nih.gov with the accession number NC_003112.2. NMB1870 is also known as GNA1870 or LP2086. Its vaccinal use is reported in i.a., Giuliani et al., PNAS, (July 2006) 103 (29): 10834; Giuliani et al., Infect. Immun. (February 2005) 73 (2): 1151; Fletcher et al., Infect. Immun. (2004) 72: 2088; and Masignani et al., J. Exp. Med. (March 2003) 197 (6): 789).

The fHBP antigen may thus comprise NMB1870, an allelic variant or a fragment thereof or any chimeric or fusion derivatives as mentioned above.

Examples of trivalent compositions include the following trivalent compositions:
  An IgA1P antigen, a TbpB antigen of isotype I and a NalP antigen;
  An IgA1P antigen, a TbpB antigen of isotype II and a NalP antigen;
  An IgA1P antigen, a TbpB antigen of isotype I and a TbpB antigen of isotype II;
  An IgA1P antigen, a TbpB antigen of isotype I and an fHBPfHBP antigen;
  An IgA1P antigen, a TbpB antigen of isotype II and an fHBPfHBP antigen;
  An IgA1P antigen, a NalP antigen and an fHBP antigen;
  An App antigen, a TbpB antigen of isotype I and a NalP antigen;
  An App antigen, a TbpB antigen of isotype II and a NalP antigen;
  An App antigen, a TbpB antigen of isotype I and a TbpB antigen of isotype II;
  An App antigen, a TbpB antigen of isotype I and an fHBP antigen;
  An App antigen, a TbpB antigen of isotype II and an fHBP antigen;
  An App antigen, a NalP antigen and an fHBP antigen;
  An AusI antigen, a TbpB antigen of isotype I and a NalP antigen;
  An AusI antigen, a TbpB antigen of isotype II and a NalP antigen;
  An AusI antigen, a TbpB antigen of isotype I and a TbpB antigen of isotype II;
  An AusI antigen, a TbpB antigen of isotype I and an fHBP antigen;
  An AusI antigen, a TbpB antigen of isotype II and an fHBP antigen; and
  An AusI antigen, a NalP antigen and an fHBP antigen;

In a particular embodiment, a trivalent composition according to the invention comprises:
(I) An IgA1P antigen which comprises or consists of:
  (a) an IgA1P fragment which essentially consists of:
    (i) the IgA1P protease domain in which the Ser residue of the catalytic triad is optionally mutated by substitution with e.g., Valine, the α-peptide domain and at least one and no more than eleven beta-sheets, preferably the first and second beta-sheets; or
    (ii) the IgA1P protease domain in which the Ser residue of the catalytic triad is optionally mutated by substitution with e.g., Valine; or
  (b) An IgA1P-App fusion polypeptide which essentially consists of the IgAIP protease sub-domain in which the Ser residue of the catalytic triad is optionally mutated by substitution with e.g., Valine, fused to the App α-peptide domain; AND
(II) A TbpB antigen, preferably non-lipidated, preferably of isotype II; AND
(III) A NalP antigen which comprises or consists of a NalP fragment which essentially consists of the NalP passenger domain, the translocator domain, the alpha-peptide and the first and second beta-sheets; wherein the Ser residue of the catalytic triad in the NalP passenger domain is optionally mutated by substitution with e.g., Alanine.

According to a preferred embodiment, a trivalent composition in accordance with the invention may comprise:
  an NalP antigen comprising a passenger domain and no more than two beta sheets, preferably extending from position 30 to position 853 of SEQ ID NO: 4, with possibly more or less 1, 2, 3, 4, or 5 amino acids on each end, and more preferably with a mutation in position 426 (preferably S→A), and
  an IgA1P antigen comprising a passenger domain and no more than two beta sheets, preferably extending from position 28 to position 1584 of SEQ ID NO: 1, with possibly more or less 1, 2, 3, 4, or 5 amino acids on each end, and more preferably with a mutation in position 267 (preferably S→V), and
  a TbpB antigen, preferably non-lipidated, preferably of isotype II.

According to another preferred embodiment, a trivalent composition in accordance with the invention may comprise:
  an NalP antigen comprising a passenger domain and no more than two beta sheets, preferably extending from position 30 to position 853 of SEQ ID NO: 4, with possibly more or less 1, 2, 3, 4, or 5 amino acids on each end, and more preferably with a mutation in position 426 (preferably S→A), and
  an IgA1P antigen comprising a protease domain, preferably extending from position 28 to position 1005 of SEQ ID NO: 1, with possibly more or less 1, 2, 3, 4, or 5 amino acids on each end, and more preferably with a mutation in position 267 (preferably S→V), and
  a TbpB antigen, preferably non-lipidated, preferably of isotype II.

According to another preferred embodiment, a trivalent composition in accordance with the invention may comprise:
  an NalP antigen comprising a passenger domain and no more than two beta sheets, preferably extending from position 30 to position 853 of SEQ ID NO: 4, with possibly more or less 1, 2, 3, 4, or 5 amino acids on each end, and more preferably with a mutation in position 426 (preferably S→A), and
  an IgA1P-App antigen comprising a protease sub-domain of IgA1P, preferably extending from position 28 to position 966 of SEQ ID NO: 1, with possibly more or less 1, 2, 3, 4, or 5 amino acids on each end, fused by its C-terminus to the N-terminus of an alpha-peptide of App, preferably extending from position 1061 to position 1187 of SEQ ID NO: 2, with possibly more or less 1, 2, 3, 4, or 5 amino acids on each end, and
  a TbpB antigen, preferably non-lipidated, preferably of isotype II.

By «quadrivalent composition» is meant a composition in which there are only four protein antigens of *N. meningitidis*. One of these four protein antigens is a trypsine-like serine protease auto-transporter (trypsine-like SPAT); the second and the third proteins antigens are a NalP antigen, a TbpB antigen, preferably of isotype II. The fourth protein antigen can be independently selected from a TbpB antigen of isotype I and any other additional *N. meningitidis* protein antigen which is not a trypsine-like SPAT, NalP and TbpB antigen. In a specific embodiment, this additional protein antigen may be the fHBP antigen of N. meningitidis.

Accordingly, in a quadrivalent composition of the invention, the N. meningitidis proteins consist of the trypsine-like SPAT, the NalP antigen, the TbpB antigen of isotype II and the TbpB of isotype I. Alternatively, in a quadrivalent composition of the invention, the N. meningitidis proteins consist of the trypsine-like SPAT, the TbpB antigen of isotype II and the TbpB antigen of isotype serotype I and any other additional N. meningitidis protein antigen which is not a trypsine-like SPAT, NalP and TbpB antigen. In a specific embodiment, this additional protein antigen may be the fHBP antigen of N. meningitidis.

Examples of quadrivalent compositions include the following quadrivalent compositions:
An IgA1P antigen, a TbpB antigen of isotype I, a TbpB antigen of isotype II and a NalP antigen;
An IgA1P antigen, a TbpB antigen of isotype I, a NalP antigen and an fHBP antigen;
An IgA1P antigen, a TbpB antigen of isotype II, a NalP antigen and an fHBP antigen;
An IgA1P antigen, a TbpB antigen of isotype I, a TbpB antigen of isotype II and an fHBP antigen;
An App antigen, a TbpB antigen of isotype I, a TbpB antigen of isotype II and a NalP antigen;
An App antigen, a TbpB antigen of isotype I, a NalP antigen and an fHBP antigen;
An App antigen, a TbpB antigen of isotype II, a NalP antigen and an fHBP antigen;
An App antigen, a TbpB antigen of isotype I, a TbpB antigen of isotype II and an fHBP antigen;
An AusI antigen, a TbpB antigen of isotype I, a TbpB antigen of isotype II and a NalP antigen;
An AusI antigen, a TbpB antigen of isotype I, a NalP antigen and an fHBP antigen;
An AusI antigen, a TbpB antigen of isotype II, a NalP antigen and an fHBP antigen;
An AusI antigen, a TbpB antigen of isotype I, a TbpB antigen of isotype II and an fHBP antigen.

In a particular embodiment, a quadrivalent composition according to the invention comprises:
(I) An IgA1P antigen which comprises or consists of:
(a) An IgA1P fragment which essentially consists of:
(i) the IgA1P protease domain in which the Ser residue of the catalytic triad is optionally mutated by substitution with e.g., Valine, the α-peptide domain and at least one and no more than eleven beta-sheets, preferably the first and second beta-sheets, or
(ii) the IgA1P protease domain in which the Ser residue of the catalytic triad is optionally mutated by substitution with e.g., Valine; or
(b) An IgA1P-App fusion polypeptide which essentially consists of the IgAlP protease sub-domain in which the Ser residue of the catalytic triad is optionally mutated by substitution with e.g., Valine, fused to the App α-peptide domain; AND
(II) A TbpB antigen of isotype I, preferably non-lipidated; and
(III) A TbpB antigen of isotype II, preferably non-lipidated; and
(IV) A NalP antigen which comprises or consists of a NalP fragment which essentially consists of the NalP passenger domain, the translocator domain, the alpha-peptide and the first and second beta-sheets; wherein the Ser residue of the catalytic triad in the NalP passenger domain is optionally mutated by substitution with e.g., Alanine.

According to a preferred embodiment, a quadrivalent composition in accordance with the invention may comprise:
an NalP antigen comprising a passenger domain and no more than two beta sheets, preferably extending from position 30 to position 853 of SEQ ID NO: 4, with possibly more or less 1, 2, 3, 4, or 5 amino acids on each end, and more preferably with a mutation in position 426 (preferably S→A), and
an IgA1P-App antigen comprising a protease sub-domain of IgA1P, preferably extending from position 28 to position 966 of SEQ ID NO: 1, with possibly more or less 1, 2, 3, 4, or 5 amino acids on each end, fused by its C-terminus to the N-terminus of an alpha-peptide of App, preferably extending from position 1061 to position 1187 of SEQ ID NO: 2, with possibly more or less 1, 2, 3, 4, or 5 amino acids on each end, and
a TbpB antigen, preferably non-lipidated, preferably of isotype II, and
a TbpB antigen, preferably lipidated, preferably of isotype I.

According to a preferred embodiment, a quadrivalent composition in accordance with the invention may comprise:
an NalP antigen comprising a passenger domain and no more than two beta sheets, preferably extending from position 30 to position 853 of SEQ ID NO: 4, with possibly more or less 1, 2, 3, 4, or 5 amino acids on each end, and more preferably with a mutation in position 426 (preferably S→A), and
an IgA1P-App antigen comprising a protease sub-domain of IgA1P, preferably extending from position 28 to position 966 of SEQ ID NO: 1, with possibly more or less 1, 2, 3, 4, or 5 amino acids on each end, fused by its C-terminus to the N-terminus of an alpha-peptide of App, preferably extending from position 1061 to position 1187 of SEQ ID NO: 2, with possibly more or less 1, 2, 3, 4, or 5 amino acids on each end, and
a TbpB antigen, preferably non-lipidated, preferably of isotype II, and
a TbpB antigen, preferably non-lipidated, preferably of isotype I.

By «pentavalent composition» is meant a composition in which there are only five protein antigens of N. meningitidis. One of these five proteins antigens is a trypsine-like serine protease auto-transporter (trypsine-like SPAT); the second, the third and fourth protein antigens are a NalP antigen, a TbpB antigen of isotype II and a TbpB antigen of isotype I, and the fifth protein antigen is any other additional N. meningitidis protein antigen which is not a trypsine-like SPAT, NalP and TbpB antigen. In a specific embodiment, this additional protein antigen may be the fHBP antigen of N. meningitidis.

Examples of pentavalent compositions include the following pentavalent compositions:
An IgA1P antigen, a TbpB antigen of isotype I, a TbpB antigen of isotype II, a NalP antigen and an fHBP antigen;
An App antigen, a TbpB antigen of isotype I, a TbpB antigen of isotype II, a NalP antigen and an fHBP antigen; and
An AusI antigen, a TbpB antigen of isotype I, a TbpB antigen of isotype II, a NalP antigen and an fHBP antigen.

The compositions according to the invention, such as the bivalent, trivalent, quadrivalent and pentavalent compositions described above, can comprise other components that are no protein antigen of *N. meningitidis*. As a matter of example, these compositions can comprise a lipooligosaccharide (LOS) of *N. meningitidis*, an adjuvant and/or an excipient.

LOS

A lipooligosaccharide (LOS) antigen of *N. meningitidis* may also be included in the immunogenic or vaccinal composition/combination of the invention. This is in particular advantageous when said composition/combination comprises a lipidated TbpB antigen, as lipidated TbpB antigen has been reported to have an adjuvant effect of the immune response induced by LOS (patent application WO2010130896).

LOS is a major constituent of the bacterial outer membrane and is anchored into the lipid outer layer of the membrane by its Lipid A moiety, the polysaccharide chains being exposed to the surface. The LOS structure varies depending on the *N. meningitidis* strain. Strains have been classified into several immunotypes (IT L1 to IT L13) based on their specific LOS structure, as a function of their reactivity with a series of antibodies that recognize various LOS epitopes (Achtman et al., J. Infect. Dis. (1992) 165: 53). As a direct consequence of this, the LOS from these *N. meningitidis* strains may by extension, also be referred to LOS of immunotype L1 to L13. The differences between immunotypes originate from variations in the composition and in the conformation of the oligosaccharide chains.

The conformation of the oligosaccharide chain is represented by formula I:

KDO
| α2-4
α chain R1-Glc$^{\beta1\text{-}4}$-Hep$^{\alpha1\text{-}5}$-KDO$^{\alpha2\text{-}6}$-Lipid A
| α1-3
β chain R2-Hep-R3
| α1-2
GlcNAc
γ chain wherein KDO is 3-deoxy-D-manno-2-octulosonic acid, Glc is glucose, Hep is heptose, GlcNAc is N-acetyl glucosamine, and wherein R1 and R2 are as shown in the table below:

TABLE 4

R1 and R2 substituents of LOS of immunotype (IT) L1 to L13

| IT | α chain (including the substituent R1) | R1 | R2 |
|---|---|---|---|
| L1 | NeuNAcα2-6Galα1-4Galβ1-4Glcβ1-4 | PEA-3 | — |
| L2 | NeuNAcα2-3Galβ1-4GlcNAcβ1-3Galβ1-4Glcβ1-4 | Glcα(1-3)** | PEA-6 or PEA-7 |
| L3 | NeuNAcα2-3Galβ1-4GlcNAcβ1-3Galβ1-4Glcβ1-4 | PEA-3 | — |
| L4 | NeuNAcα2-3Galβ1-4GlcNAcβ1-3Galβ1-4Glcβ1-4 | — | PEA-6 |
| L5 | NeuNAcα2-3Galβ1-4GlcNAcβ1-3Galβ1-4Glcβ1-4Glcβ1-4 | Glcα(1-3) | — |
| L6 | GlcNAcβ1-3Galβ1-4Glcβ1-4 | — | PEA-6 or PEA-7 |
| L7 | Galβ1-4GlcNAcβ1-3Galβ1-4Glcβ1-4 | PEA-3 | — |
| L8 | Galβ1-4Glcβ1-4 | PEA-3 | — |
| L9 | Galβ1-4GlcNAcβ1-3Galβ1-4Glcβ1-4 | — | PEA-6 |
| L10 | n.d. | n.d. | n.d. |

TABLE 4-continued

R1 and R2 substituents of LOS of immunotype (IT) L1 to L13

| IT | α chain (including the substituent R1) | R1 | R2 |
|---|---|---|---|
| L11 | Glcβ1-4Glcβ1-4 | PEA-3 | PEA-6 |
| L12 | n.d. | n.d. | n.d. |
| L13 | n.d. | n.d. | n.d |

**when R2 is a glucose residue, R2 is commonly called β chain.
n.d.: not determined.
PEA: phosphoethanolamine;
PEA-3: PEA substituent transferred at O-3 position of Glcp;
PEA-6: PEA substituent transferred at O-6 position of Hep;
PEA-7: PEA substituent transferred at O-7 position of Hep.

The structure of LOS of immunotypes 1 to 11 is also reported in particular in WO 10/130898.

For use in the composition of the invention, the LOS may be of any immunotype e.g. L2 or L3, optionally modified by genetic engineering as described in U.S. Pat. No. 5,705,161 or WO 04/014417 or WO 01/022994, so that the LOS does not bear the Galβ1-4GlcNAcβ1-3 Galβ1-4Glcβ1-4 carbohydrate unit or lacto-N-neotetraose unit which constitutes an epitope which can potentially cross-react with human erythrocytes. Accordingly, it is possible to envisage using a LOS from a strain of immunotype L2 or L3 in which a gene involved in the biosynthesis of the alpha chain has been inactivated by mutation, so as to obtain an incomplete LNnT structure. Such mutations are proposed in patent application WO 04/014417. This involves extinguishing, by mutation, the IgtB, IgtE (or IgtH), IgtA or IgtA and IgtC genes. Thus, it appears to be possible and advantageous to use an LOS originating from an *N. meningitidis* strain of immunotype L2 or L3 mutated as described in WO 04/014417.

Alternatively, it may be also advisable to use an LOS which does not possess this lacto-N-neotetraose unit. It may therefore be particularly advantageous to use a LOS of immunotype L6 or L8, preferably L6, or an L6 LOS as described in WO 10/130898, modified by genetic engineering i.a., to bear an additional phospho-ethanolamine group.

LOS is a toxic compound that may be first detoxified before use in mammals. Various detoxification methods are reported in the art, including chemical, enzymatic, genetic methods e.g., as respectively described in U.S. Pat. No. 6,531,131, U.S. Pat. No. 6,482,807 and U.S. Pat. No. 6,887,483. Detoxification may also be achieved by association of LOS with a peptide analog of polymixin B as described in WO 06/108586 or by incorporation of LOS into a delivery structure (e.g., liposomes) as described in U.S. Pat. No. 5,888,519. Advantageously, the LOS may be incorporated into liposomes which may be anionic or cationic, preferably cationic e.g. involving a cationic lipid such as ethyl-PC as described in e.g. U.S. Pat. No. 5,698,721, U.S. Pat. No. 5,902,802 or U.S. Pat. No. 5,651,981. A detoxification method including the production of LOS incorporated into cationic liposomes is described in WO 10/130896.

LOS of *N. meningitidis* such as those described above, may act as a vaccinal antigen and may also have an adjuvant effect on the immune response induced by the protein antigens. Accordingly, when LOS is used in a composition of the invention, there may be no need to add an additional adjuvant such as those cited below. In a particular embodiment, LOS in liposomes is added to any of the bivalent, trivalent, quadrivalent or pentavalent compositions described above, i.a., when one of the protein antigens is a lipidated TbpB antigen.

Accordingly, in a particular embodiment, a composition of the invention comprising a *N. meningitidis* LOS (e.g., formulated in LOS-liposomes) as described hereinabove, advantageously comprises at least one first lipidated TbpB antigen of either isotype I or II, preferably isotype I. When such a composition comprises a second Tbp, this TbpB may be lipidated or not, and is of the isotype differing from that of the first lipidated B. For the purposes of the present invention, the LOS may be obtained by conventional means. In particular, it can be extracted from a bacterial culture, and then purified according to conventional methods. Many methods of production are described in the literature. By way of example, mention is made, i.e., of Westphal & Jann, (1965) Meth. Carbohydr. Chem. 5: 83; Gu & Tsai, 1993, Infect. Immun. 61 (5): 1873; Wu et al., 1987, Anal. Biochem. 160: 281 and U.S. Pat. No. 6,531,131. A LOS preparation can be quantified according to well-known procedures. Assaying of KDO by high performance anion exchange chromatography (HPAEC-PAD) is a method which is most particularly suitable.

Adjuvants

In a particular embodiment of the invention, the immunogenic composition further comprises one or several adjuvant(s).

The term "adjuvant" as used herein denotes a product which, added to the content of an immunogenic composition, in particular to a vaccine, increases the intensity of the immune reaction induced in the mammalian host to which said composition is administered. An adjuvant may in particular increase the quantity/quality of specific antibodies e.g. bactericidal antibodies, which said host is capable of producing after administration of said composition and thus increases the efficiency of the immune response.

The adjuvant (s) that can be used in the context of the invention include adjuvants promoting a Th1 and/or Th2 immune response. Accordingly, for use in the composition of the invention, an adjuvant may be a Th1, Th2 or Th1/Th2 adjuvant. The meaning given to "Th1, Th2 or Th1/Th2 adjuvant" shall be the meaning commonly acknowledged by the scientific community. A Th1 adjuvant promotes an immune response characterized by the predominant production of IFN-γ and/or IL-2 cytokines. A Th2 adjuvant promotes an immune response characterized by the predominant production of e.g., IL-4, IL-5, IL-6 and/or IL-10 cytokines. A Th1/Th2 adjuvant favours a balanced cytokine production (balanced immune response).

Examples of adjuvants promoting a Th1-type immune response include but are not limited to agonists of Toll-like receptors (TLRs), in particular to agonists of TLR4, which may be formulated or not. Typical formulation of a TLR agonist such as a TLR4 agonist, include oil-in-water emulsions. LPS derivatives like 3-De-O-acylated Monophosphoryl Lipid A (3D-MPL) described in WO 94/00153 or a 3D-MPL derivative named RC-529 described in U.S. Pat. No. 6,113,918 are well known TLR4 agonists; Other TLR4 agonists which share structural similarity with monophosphoryl lipid A, referred to as aminoalkyl glucosaminide phosphates (AGPs), are described in U.S. Pat. No. 6,113,918, U.S. Pat. No. 6,303,347, and WO 98/50399. Other synthetic TLR4 agonists are described in US 2003/0153532. Among these synthetic agonists, reference is made of a chemical compound named as E6020 and referenced in the Chemical Abstract Services (CAS) registry as CAS Number 287180-63-6 as particularly suitable Th1-adjuvant in the context of the invention. The chemical formula of the disodic salt is $C_{83}H_{63}N_4O_{19}P_2$, $_2Na$ and the developed chemical formula is as follows:

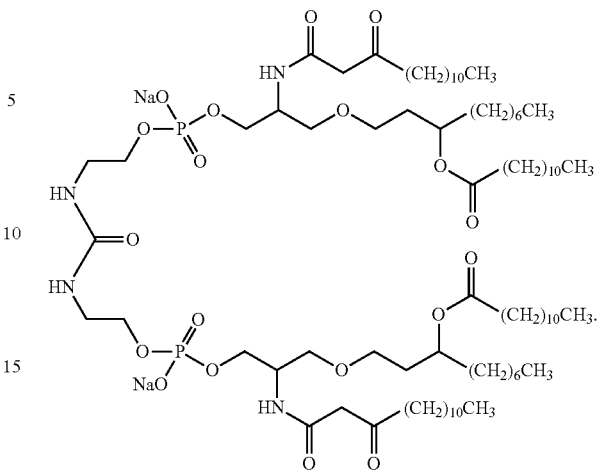

The R configuration (R,R,R,R) of the four asymetric carbons is preferred. The synthesis process is described in WO2007/005583. E6020 is preferably formulated in an oil-in-water emulsion and more particularly formulated in an oil-in-water emulsion (such as the one described in WO 07/006939), according to the process as described in the patent application WO 2007/080308.

Examples of adjuvants promoting a Th2-type immune response include but are not limited to aluminium salts and especially aluminium oxy hydroxide (also called for sake of brevity aluminium hydroxide) or aluminum hydroxy phosphate (also called for sake of brevity aluminum phosphate). When an aluminium salt is used, the protein antigens may advantageously be adsorbed onto the aluminium salt.

Excipients

In a composition of the invention, the active ingredients i.a., the protein antigens, may be formulated together with a pharmaceutically-acceptable excipient such as a pharmaceutically acceptable diluent or carrier. In a particular embodiment, the composition of the invention may comprise a buffer and/or an isotonic agent such as sodium chloride or sugars e.g. sucrose; and/or a stabilizing agent such as histidine.

An immunogenic composition according to the invention is useful for inducing an immune response in a mammal, in particular humans, against *N. meningitidis* of any serogroup, in particular against serogroup B. This immune response includes in particular, a bactericidal immune response wherein bactericidal antibodies are induced against *N. meningitidis*. By "bactericidal antibody" is meant antibodies able to kill the bacteria in the presence of complement (which is a component of the humoral immune system of mammals). The antibodies produced as part of the immune response upon administration of the immunogenic composition may be identified as "bactericidal antibodies" in a serum bactericidal assay using an appropriate source of complement, according to methods known in the art.

An immunogenic composition according to the invention is particularly useful for inducing an immune response i.a., a bactericidal immune response, against *N. meningitidis* strains of (i) the clonal complexes of the hyper-invasive lineage (invasive clonal complexes); (ii) the clonal complexes wherein strains of serogroup B are prevalent (highly represented), those complexes being or not prevalent worldwide, advantageously prevalent worldwide; and/or (iii) clonal complexes ST8, ST11, ST18, ST32, ST41/44, ST162 and/or ST269. The immunogenic composition is more particularly useful against *N. meningitidis* strains of serogroup B belonging to clonal complexes, such as the ST8, ST11, ST18, ST32, ST41/44, ST162 and/or ST269 complex(es). The immunogenic composition may be characterized by strain coverage of at least 70%. In other words, it may induce a bactericidal immune response against at least 70%, 75%, 80%, 85%, 90%, 95% or 100% of *N. meningitidis* strains of the clonal complexes specified above, in particular the ST8, ST11, ST18, ST32, ST41/44, ST162 and/or ST269 complex(es).

Strain coverage may be determined as described in the experimental part of the specification, involving in particular (i) the selection of a collection of strains representative of the most important clonal complexes e.g. including ST8, ST11, ST18, ST32, ST41/44, ST162 and/or ST269 complex (es) and (i) the achievement of an SBA assay against each of the strains of the collection, such as described in the experimental part. Briefly, the whole test consist in administering the composition to a mammal, one or several times at appropriate interval; collecting the sera that may optionally be pooled (within a group of mammals submitted to identical administration); culturing the strains of the collection; and testing the individual sera or pooled serum and/or dilutions thereof against each strain in an SBA assay, such as the one described in the experimental part. The percentage of coverage is determined on the basis of the number of strains responding positively—that is, against which the bactericidal titer of e.g., the pooled serum, meets (e.g., equals or is superior to) the threshold value considered as indicative of a positive surrogate of protection—over the total number of strains tested. Alternatively, the bactericidal titer of individual sera within a group of mammals as defined above, may be determined and the geometric mean titer (GMT) established. In that case, the strain is considered to respond positively when the GMT meets (e.g., equals or is superior to) the threshold value considered as indicative of a positive surrogate of protection.

According to an embodiment, the invention relates to a composition comprising a combination of antigens as above-described together with a pharmaceutically acceptable diluent or carrier.

According to another embodiment, the invention relates to a combination of antigens as above-described or a composition as above-described, for use as a vaccine, and more preferably for use for the prevention and/or treatment of *N. meningitidis* B infection.

According to another embodiment, the invention relates to a vaccine composition comprising a combination of antigens as above-described, or a composition as above-described.

According to an embodiment, the invention relates to an immunogenic composition comprising a combination of antigens as above-described.

An immunogenic composition according to the invention may be used as a pharmaceutical composition, in a prophylactic or therapeutic manner. Typically, it may be used as a vaccine composition for protecting against *N. meningitidis* infections e.g., for treating or preventing *N. meningitidis* infections. *N. meningitidis* induces a large range of infections from asymptomatic carriage to invasive diseases e.g., *meningitidis* and/or septicemia. Typically, the immunogenic or pharmaceutical composition of the invention comprises a therapeutically or prophylactically effective amount of each of the protein antigens. A therapeutically and/or prophylactically effective amount of a protein antigen may vary according to factors such as the disease state, age, sex, and weight of the individual, and the ability of the protein antigen, to elicit a desired therapeutic and/or prophylactic result.

The composition according to the invention may be administered as a dose wherein the amount of each of the protein antigens depends on various conditions including e.g., the weight, the age and the immune status of the recipient. As a matter of guidance, it is indicated that a dose of the composition of the invention may comprise a therapeutically and/or prophylactically effective amount of each of the protein antigen, which may be from 10 µg to 1 mg, e.g. about 50 µg per protein antigen included in the composition of the invention.

'Prevention' refers to prophylactic treatment, wherein a composition of the invention is administered to an individual with no symptoms of meningitis and/or septicaemia and/or no detectable *N. meningitidis* infection. Said prophylactic treatment is preferably administered with the aim of preventing or reducing future *N. meningitidis* infection.

Within the meaning of the invention, the terms "for preventing or for prevention" intend to mean, with reference to an *N. meningitidis* infection, a reduction of risk of occurrence of said infection and/or symptoms associated with said infection.

'Treatment' includes both therapeutic treatment and prophylactic or preventative treatment, wherein the object is to prevent or slow down the infection or symptoms of disease. Those in need of treatment include those already with the disorder as well as those prone to have the disorder or those in whom the disorder is to be prevented. The terms 'therapy', 'therapeutic', 'treatment' or 'treating' include reducing, alleviating or inhibiting or eliminating the symptoms or progress of a disease, as well as treatment intended to reduce, alleviate, inhibit or eliminate said symptoms or progress.

A further object of the invention is to provide a method of inducing an immune response, in particular a bactericidal immune response, against *N. meningitidis*, in particular against *N. meningitidis* of serogroup B, which comprises administering to an individual in need an immunogenic composition according to the invention. Still within the scope of the invention, it is provided a method of treating or preventing a *N. meningitidis* infection, in particular against *N. meningitidis* of serogroup B, which comprises administering to a patient in need a composition according to the invention.

In order to achieve the desirable effect, the composition of the invention may be administered as a primary dose, in a primary immunisation schedule, one or several times, e.g., two or three times, at appropriate intervals defined in terms of week or advantageously, month. In a particular embodiment, the interval between the primary doses may be not less than one or two months, depending on the conditions of the subject receiving the doses. If needed, the primary doses may possibly be followed by a booster dose of the composition of the invention, which may be administered e.g., from at least 6 months, preferably at least one year to two-five years, after the last primary dose.

The composition according to the invention may be administered by any conventional routes in use in the vaccine field e.g. by parenteral route such as the subcutaneous or intramuscular route. In a particular embodiment, the composition is suitable for injection and formulated accordingly. It may be in a liquid form or in a solid form that, before administration, may be extemporaneously suspended in a pharmaceutically-acceptable diluent.

Also provided, is a combination of antigens of the invention in the manufacture of a medicament for the preventive or therapeutic treatment of a *N. meningitidis* infection, e.g. an infection of *N. meningitidis* of serogroup B, such as meningitis.

Also provided, is a combination of antigens or composition of the invention for use in a method of inducing an immune response to *N. meningitidis*, in particular *N. meningitidis* of serogroup B. Also provided, is a combination of antigens or composition of the invention for use in a method of preventing or treating a *N. meningitidis* infection, e.g. an infection of *N. meningitidis* of serogroup B, such as meningitis. In some embodiments, said method comprises administering said combination of antigens or composition to a subject, in particular a subject in need thereof. According to one embodiment, a method of the invention may comprise the step of observing a preventing and/or a treating effect with regard to a *N. meningitidis* infection.

Also provided is a method of inducing an immune response to *N. meningitidis*, in particular *N. meningitidis* of serogroup B, which comprises administering a combination of antigens or composition of the invention to an individual in need thereof. Also provided is a method of preventing or treating of meningitis, in particular *N. meningitidis* infection, e.g. an infection of *N. meningitidis* of serogroup B, such as meningitis, which comprises administering a combination of antigens or composition of the invention to an individual in need thereof.

The invention will be further illustrated by the following figures, sequences and experimental part.

BRIEF DESCRIPTION OF THE FIGURES

FIG. 1 is a graph showing cross-SBA results generated with M982 His-TbpB. SBA results are expressed in term of fold-increase. SE=surface exposure of TbpB as assessed by FACS using an antiserum against the injected protein.

FIG. 4 is a graph showing cross-SBA results generated with a bivalent composition comprising M982 His-TbpB+MC58 NalP SP509 construct. SBA results are expressed in term of fold-increase. SE=surface exposure of the injected proteins as assessed by FACS using an antiserum against the combination of injected proteins.

FIG. 5 is a graph showing cross-SBA results generated with a bivalent composition comprising MC58 NalP SP509 construct+MC58 IgAlP SP503 construct. SBA results are expressed in term of fold-increase.

FIG. 7 is a graph showing cross-SBA results generated with a trivalent composition comprising M982 His-TbpB+MC58 NalP SP509 construct+MC58 IgAlP SP503 construct. SBA results are expressed in term of fold-increase. SE=surface exposure of the injected proteins as assessed by FACS using an antiserum against the combination of injected proteins.

BRIEF DESCRIPTION OF THE SEQUENCE LISTING

Figure 2:
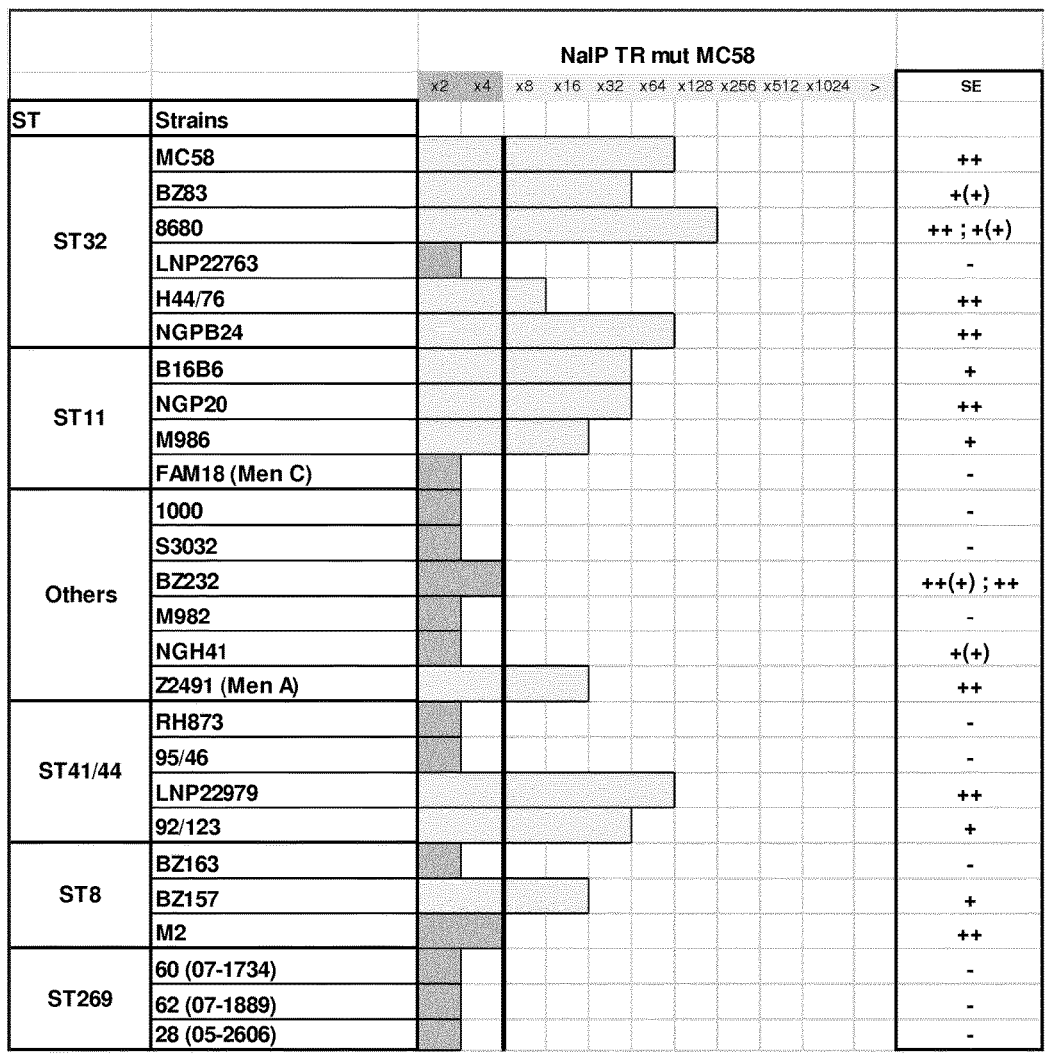
FIG. 2 is a graph showing cross-SBA results generated with MC58 NalP SP509 construct. SBA results are expressed in term of fold-increase. SE=surface exposure of NalP as assessed by FACS using an antiserum against the injected protein.
Figure 3:
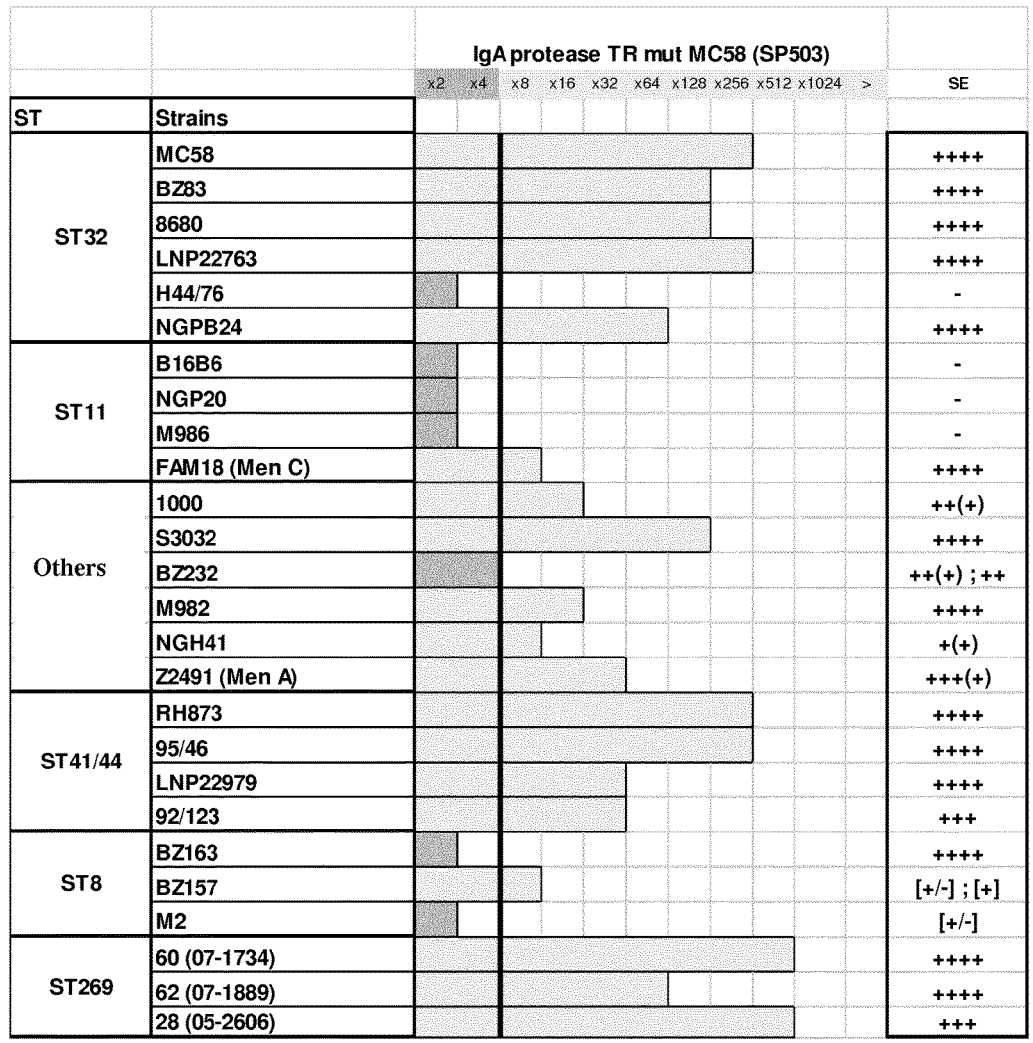
FIG. 3 is a graph showing cross-SBA results generated with MC58 IgA1P SP503 construct. SBA results are expressed in term of fold-increase. SE=surface exposure of IgA1P as assessed by FACS using an antiserum against the injected protein.
Figure 6:
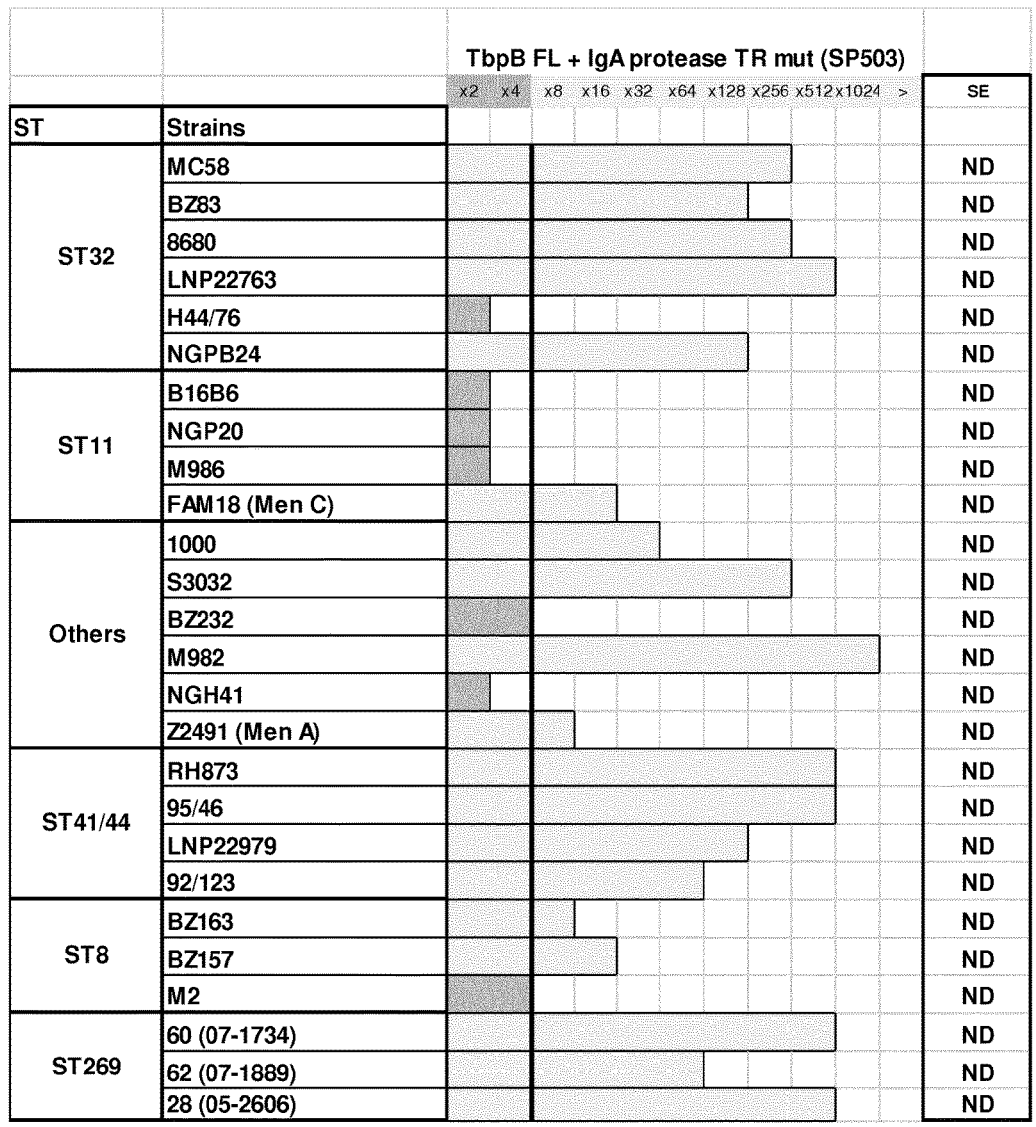
FIG. 6 is a graph showing cross-SBA results generated with a bivalent composition comprising M982 His-TbpB+MC58 IgA1P SP503 construct. SBA results are expressed in term of fold-increase.
Figure 8:
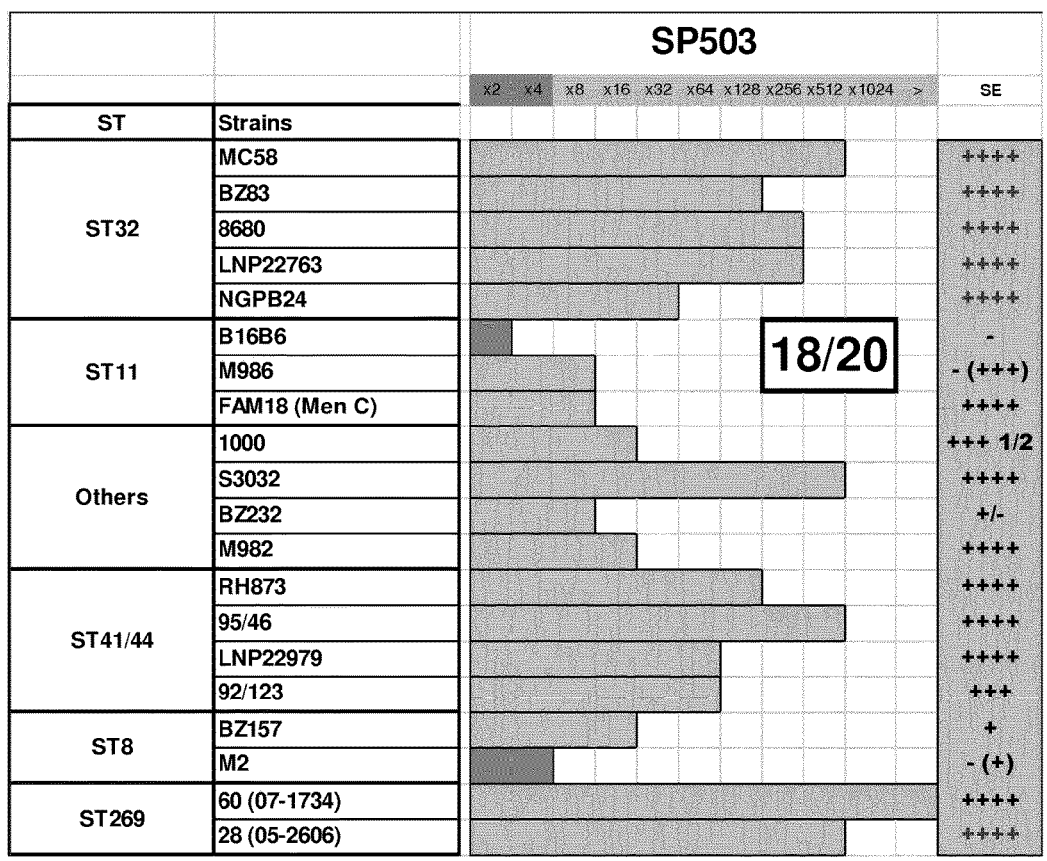
FIG. 8 is a graph showing cross-SBA results generated with MC58 IgA1P SP503 construct. SBA results are expressed in term of fold-increase. SE=surface exposure of IgA1P as assessed by FACS using an antiserum against the injected protein.
Figure 9:
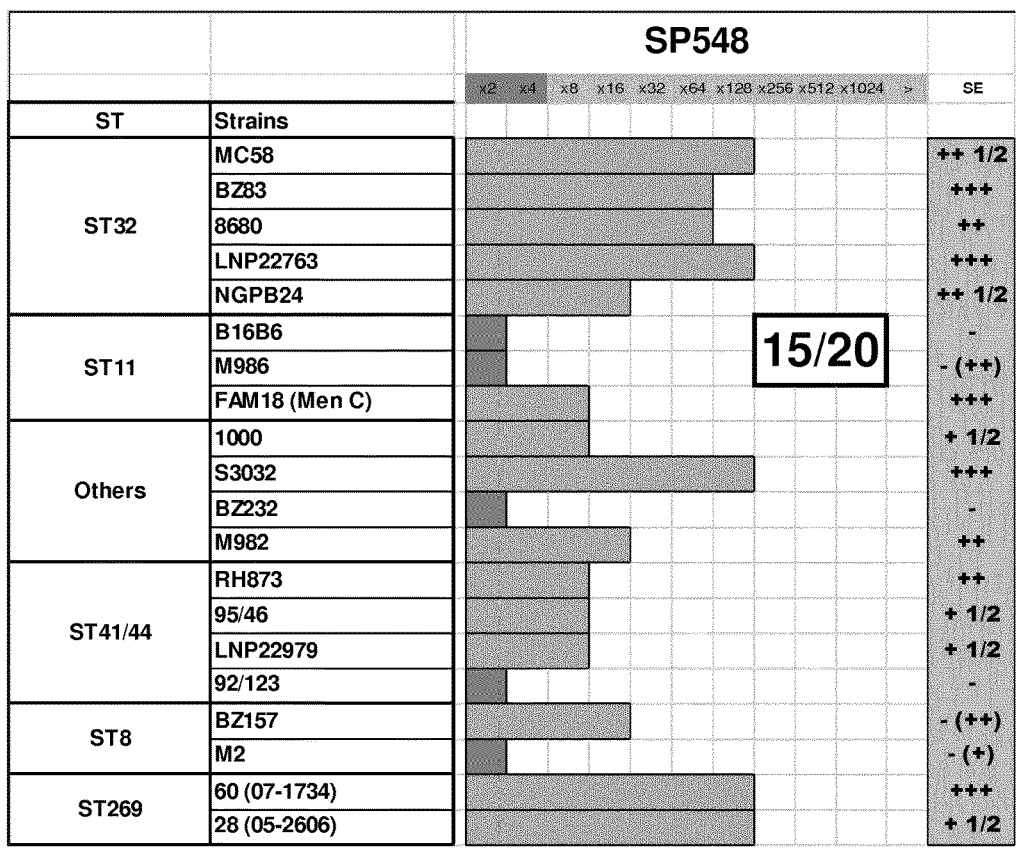
FIG. 9 is a graph showing cross-SBA results generated with MC58 IgA1P SP548 construct. SBA results are expressed in term of fold-increase. SE=surface exposure of IgA1P as assessed by FACS using an antiserum against the injected protein.
Figure 10:
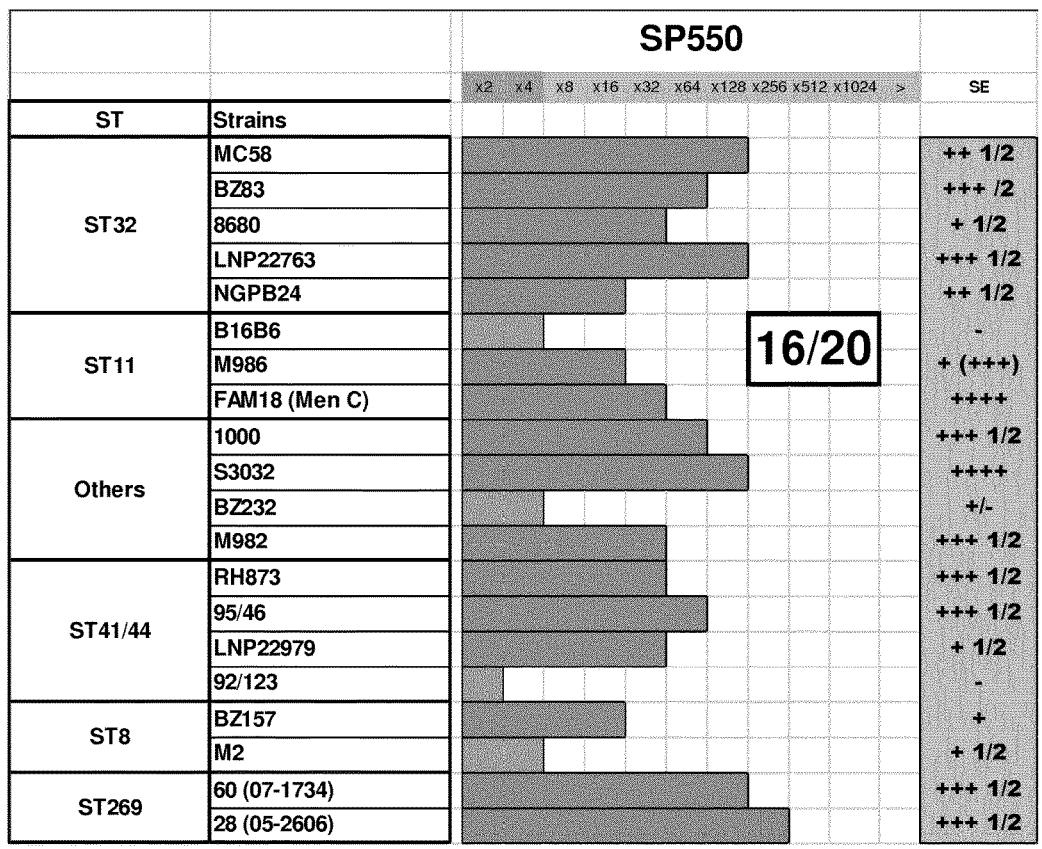
FIG. 10 is a graph showing cross-SBA results generated with MC58 IgA1P-App fusion construct SP550. SBA results are expressed in term of fold-increase. SE=surface exposure of injected proteins as assessed by FACS using an antiserum against the injected protein.
Figure 11:
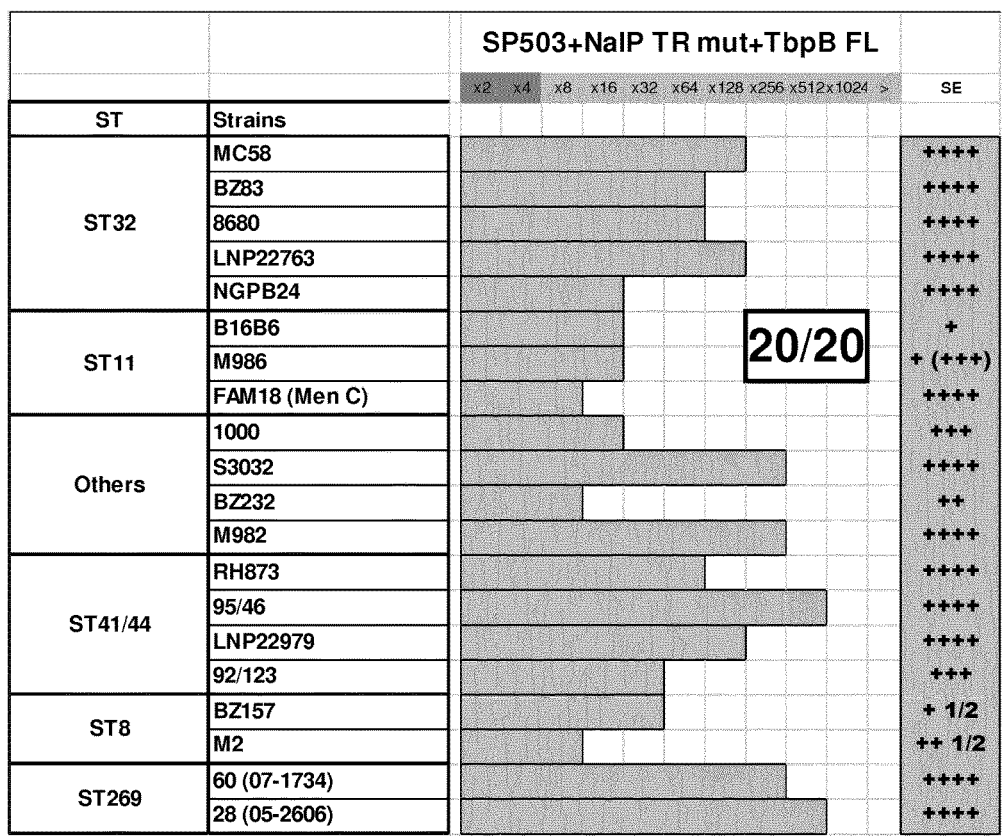
FIG. 11 is a graph showing cross-SBA results generated with a trivalent composition comprising MC58 IgA1P SP503 construct+MC58 NalP SP509 construct+M982 TbpB. SBA results are expressed in term of fold-increase. SE=surface exposure of the injected proteins as assessed by FACS using an antiserum against the combination of injected proteins.
Figure 12:
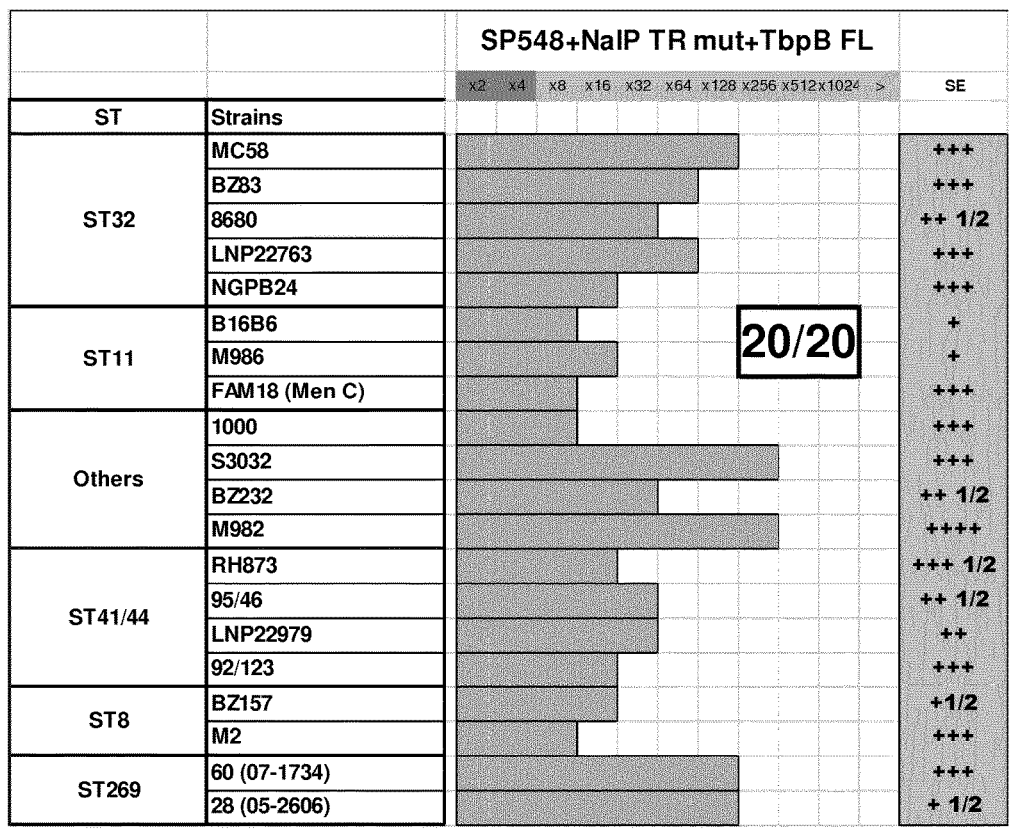
FIG. 12 is a graph showing cross-SBA results generated with a trivalent composition comprising MC58 IgA1P SP548 construct+MC58 NalP SP509 construct+M982 TbpB. SBA results are expressed in term of fold-increase. SE=surface exposure of the injected proteins as assessed by FACS using an antiserum against the combination of injected proteins.
Figure 13:
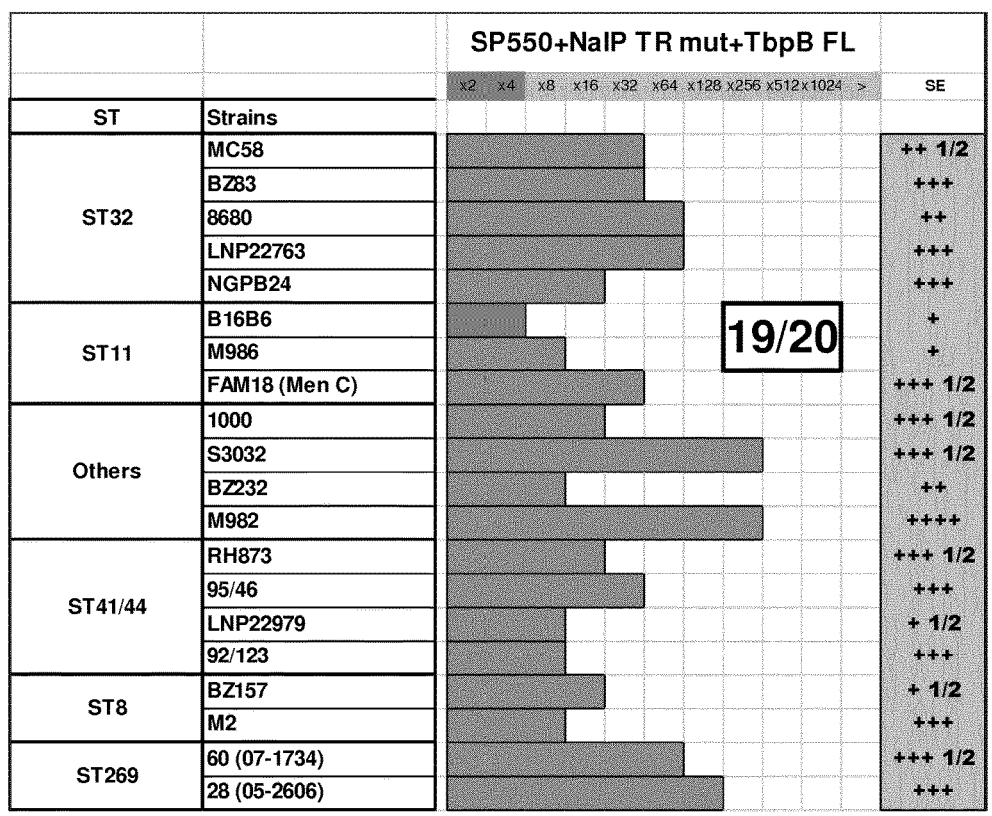
FIG. 13 is a graph showing cross-SBA results generated with a trivalent composition comprising MC58 IgA1P-App fusion construct SP550+MC58 NalP SP509 construct+M982 TbpB. SBA results are expressed in term of fold-increase. SE=surface exposure of the injected proteins as assessed by FACS using an antiserum against the combination of injected proteins.

SEQ ID No:

1 IgA1P from *N meningitidis* strain MC58 amino acid sequence

2 App from *N meningitidis* strain MC58 amino acid sequence

3 AusI from *N meningitidis* strain MC58 amino acid sequence

4 NalP from *N meningitidis* strain MC58 amino acid sequence

5 TbpB from *N meningitidis* strain M982 amino acid sequence

6 TbpB from *N meningitidis* strain B16B6 amino acid sequence

7 NalP construct SP509 amino acid sequence, without the His-tag

8 IgA1P construct SP503 amino acid sequence, without the His-tag

9 IgA1P construct SP548 amino acid sequence, without the His-tag

10 MC58 IgA1P-App fusion construct SP550 amino acid sequence, without the

His-tag

EXAMPLES

A—Materials & Methods

Non-His-tag Proteins

M982 TbpB

Preparation of *E. coli* BL21 (D3) pSP314

The expression strain is the *E. coli* BL21 (DE3) strain containing the pSP314 plasmid. This plasmid derives from plasmid pET28 (Novagen). The sequence encoding TbpB from strain M982 without the peptide signal sequence and the first cysteine residue of the mature protein (but with an initiation codon), is placed under the control of the T7 promoter (from pET28). This plasmid contains also a kanamycin resistant gene and a plasmid stability element.

Culture *E. coli* BL21 (D3) pSP314

Preculture at a 3 L Scale

A working seed vial of *E. coli* BL21 (D3) pSP314 was thawed and used to inoculate shake flasks containing a classical *E. coli* culture medium comprising salts and yeast extract at an inoculation rate of 0.5 ml inoculum/500 ml medium in 2 L flasks. Incubation was pursued overnight at 37° C.

Culture in 30 L Fermentor

The preculture is transferred to a 30 L fermentor containing a classical *E. coli* culture medium comprising salts and yeast extract at a 5% inoculation rate to a final volume of 20 L. The culture is pursued overnight (16 hrs; pH 7.0; 37° C.: pO2: 30%; speed: 200 rpm to max). At O.D. 600 nm 25-35, IPTG (isopropyl β-D-1-thiogalactopyranoside) is added for 3 hrs to a final concentration of 1 mM. Then the temperature is decreased to 10° C. and the bacteria are harvested by centrifugation (20 min; 7 000 g). Cell pellets are frozen at −20° C. and then stored at −35° C.

Preparation of a Cell Extract Before Purification

Frozen cell pellets are thawed at +5° C. during 16-96 hrs and resuspended in a lysis buffer Tris 50 mM pH 9 (ratio 150 g of wet cell weight per liter of buffer) by mechanical mixing with an ultraturrax at 13 000-16 000 rpm. $MgCl_2$ at a final concentration of 1 mM and benzonase (endonuclease) at 30 UI/g of wet cells are added to the suspension before cell disruption.

Cell disruption is performed at 5° C. by high pressure homogenization (PANDA 2K, Niro Soavi) under 1300 bars. The bacterial lysate is clarified by centrifugation at 13 000 g during 2 hrs. The supernatant is finally filtrated on a 0.45 μm Durapore membrane (Millipore).

Purification

A small scale lot was produced using three purification steps including (i) a first capture step by anion exchange chromatography (AEX), (ii) an intermediate step by hydrophobic chromatography (HIC) and (iii) a final step by ultrafiltration on a 30 kDa membrane using an Ultracel cassette from Millipore. The purity of TbpB small scale lot was about 87%.

A pilot scale lot was produced using four main purification steps including (i) a first capture step by anion exchange chromatography (AEX), (ii) an intermediate step by hydrophobic chromatography (HIC); (iii) a concentration step on a 10 kDa membrane using Ultracel cassette from Millipore and (iv) a size exclusion chromatography (SEC). The purity of TbpB pilot scale lot was superior to 90%.

Purification of the Small Scale Lot

First Capture Chromatography: Anion Exchange Chromatography

The clarified lysate in Tris 50 mM, pH 9 obtained from cell disruption was applied onto a Capto Q gel (GE HealthCare) packed in a 1.8 L BPG column from GE Healthcare (3.8 mg of total protein/L of gel) previously equilibrated with Tris 50 mM, pH 9. The chromatography was performed at a flow rate of 300 cm/hr. The column was washed with Tris 50 mM, pH 9 and the protein was eluted by step with 4 CV of Tris 50 mM, NaCl 150 mM, pH 9.

Recovered fractions were analysed by SDS-PAGE (M982 TbpB as produced≈72 kDa) and those containing M982 TbpB were pooled and stored at 5° C. before further purification.

Intermediate Chromatography: Hydrophobic Chromatography

The 0.22 μm filtrate was adjusted to 1 M ammonium sulfate, and to pH 7.5 by HCl addition and then filtered on 0.45 μm filter.

The 0.45 μm filtrate was divided in two fractions and processed in two runs onto a 80 ml Phenyl Sepharose High Sub 6 Fast flow gel (GE HealthCare) packed into an XK16 column from GE Healthcare and previously equilibrated with phosphate 50 mM, ammonium sulfate 1 M, pH 7.5. The chromatography was performed at a flow rate of 300 cm/hr. The collected flow-through (TbpB is not retained on the column) of the two runs were pooled and stored at 5° C. before further purification.

Concentration/Diafiltration Step:

The HIC Flow-through was submitted to ultrafiltration on a 30 kDa Ultracel membrane using a Pellicon 3 cassette (Millipore) for buffer exchange against PBS and product concentration. For further use, the preparation was concentrated at 1.3 mg/ml M982 TbpB in PBS.

Purification of the Pilot Scale Lot

First Capture Chromatography: Anion Exchange Chromatography

The clarified lysate in Tris 50 mM, pH 9 obtained from cell disruption was applied onto a Capto Q gel (GE HealthCare) packed into a 3.8 L axichrom column from GE Healthcare (18 mg of total protein/ml of gel) and previously equilibrated with Tris 50 mM, pH 9. The chromatography was performed at a flow rate of 300 cm/hr. The column was washed with Tris 50 mM, pH 9 and the protein was eluted by steps with 4 CV of Tris 50 mM, NaCl 150 mM, pH 9.

Recovered fractions were analysed by SDS-PAGE (M982 TbpB=72 kDa) and those containing M982 TbpB were pooled, filtered onto a 0.22 μm 1900 $cm^2$ Optical XL4 filter (Durapore, Millipore) and stored at 5° C. before further purification.

Intermediate Chromatography: Hydrophobic Chromatography

The 0.22 μm filtrate was adjusted at 1 M Ammonium sulfate, and at pH 7.5 by HCl addition and then filtered on 0.22 μm filter.

The 0.22 μm Q eluate was loaded onto a Phenyl Sepharose High Sub 6 Fast flow gel (GE HealthCare) gel (Axichrom from GE Healthcare) packed into a 0.6 L BPG column, previously equilibrated with Tris 50 mM, ammonium Sulfate 1 M, pH 7.5. The chromatography was performed at a flow rate of 300 cm/hr. The collected flow-through (TbpB is not retained on the column) was filtrated onto a 0.22 μm 1900 cm² Optical XL4 filter (Durapore, Millipore) before further purification.

Polishing Step for the Pilot Scale Lot: Size Exclusion Chromatography (SEC)

The 0.22 μm filtrate was submitted to a concentration/diafiltration step by tangential flow filtration on 10 kDa Ultracel membrane using three 0.1 m² Pellicon 3 cassettes (Millipore) for buffer exchange and product concentration before the final SEC.

The cassettes were first conditioned in buffer Tris 50 mM, NaCl 100 mM, pH 7.5. A polarization step with the HIC flow-through was then performed during 10 min. The product was then pre-concentrated and diafiltered against 10 diavolumes of Tris 50 mM, NaCl 100 mM, pH 7.5. Then, the product was concentrated to the minimum working volume (0.4 L) and the membranes were rinsed with the diafiltration buffer. The final retentate collected was <350 ml (<7% of the SEC column volume).

After concentration, the product was applied on a SEC column using a Superdex 75 sorbent. The product was loaded on the column (<7% of the column volume on a 4.9 L BPG column) at a flow rate of 30 cm/h in a Tris 50 mM, NaCl 100 mM, pH 7.5 buffer. During elution, fractions were collected and each fractions analyzed by SDS PAGE. Fractions containing poor level of 20 kDa impurities were pooled.

The pooled fractions were diluted in Tris 50 mM, NaCl 100 mM, pH 7.5 to a concentration of 2 mg/ml and stabilized in 10% sucrose and stored at −70° C. For use, the thawed solution is diluted to a final concentration of 1 mg/ml in Tris 50 mM, NaCl 100 mM, pH 7.5, sucrose 5%.

B16B6 TbpB

The expression strain is the *E. coli* BL21 strain containing the pTG9216 plasmid. This plasmid contains in particular a kanamycin-selectable marker and the polynucleotide encoding the mature TbpB from *N. meningitidis* B16B6 fused to the *E. coli* RlpB (real lipoprotein B) signal sequence and placed under the control of the arabinose promoter (araB). As a result of this, the expressed TbpB is lipidated.

The expression strain is cultured as described in WO 10/130896 for the preparation of M982 TbpB. LPS is extracted and cell lysis is performed as described in WO 10/130896. After lysis, membranes are washed in Tris-HCl 50 mM, Urea 1 M; then in Tris-HCl 50 mM, EDTA 25 mM; and finally in Tris-HCl 50 mM. Membranes are solubilized to extract B16B6 TbpB as described in WO 10/130896.

B16B6 TbpB is purified by two successive anion exchange chromatographies followed by a cation exchange chromatography as described in WO 10/130896. Eluted fractions recovered from each chromatography are analysed by SDS-PAGE (B16B6 TbpB=68 kDa) and those containing B16B6 TbpB are pooled.

Dialysis and concentration of the pooled fractions recovered from the last chromatography are achieved as described in WO 10/130896. Purified B16B6 TbpB is finally treated by adsorption on Bio-Beads™ SM-2 in order to remove the excess Elugent™ detergent (surfactant constituted of alkyl glucosides which could destabilize the LPS L8 liposomes) as described in WO 10/130896.

B16B6 TbpB is stored in PBS merthiolate 0.001% at −80° C.

Preparation and Purification of His-Tag Protein Constructs

M982 His-TbpB

The sequence encoding the mature TbpB protein from strain M982 was produced from the tbpB sequence available from the database Entrez Gene du NCBI (National Center for the Biotechnology Information) at http://www.ncbi.nlm-.nih.gov under the accession number Z15130 corresponding to the M982 tbp locus. The sequence encoding the mature protein [without the peptide signal sequence and the first amino acid (Cys); starting with Leu in position 2] was placed in a pET28 plasmid (Novagen), in frame with and immediately downstream a His-tag encoding sequence, under the control of the T7 promoter. The M982 His-TbpB expression plasmid contains a kanamycin resistant gene and a plasmid stability element.

*E. coli* BL21 (DE3) transformed with this plasmid was cultured at 37° C. in Luria-Bertani medium complemented with 50 μg/ml kanamycine. The expression of M982 His-TbpB was induced by adding 1 mM IPTG. The expression was pursued for 3 hrs.

Bacteria were harvested by centrifugation and pellets are washed with Tris 20 mM, NaCl 300 mM, pH 8.0. The bacterial suspension was centrifuged (6 000 g 15 min) and pellets were resuspended in Tris 20 mM, NaCl 300 mM, pH 8.0, complemented with lysozyme (100 pg/ml) MgCl2 1 mM and Triton X100 0.1%. Incubation was pursued 15 min at 4° C. under mild stirring.

One Unit/ml of benzonase was added. Incubation was pursued 15 min at 4° C. under mild stirring. The suspension was then centrifuged at 30 000 g for 20 min at 4° C. The supernatant was recovered.

The supernatant was loaded at a flow rate of 2 ml/min on a His-trap column FF previously equilibrated with buffer A (Tris 20 mM, NaCl 300 mM pH 8.0). The column was then submitted to a linear imidazole gradient from 0 to 250 mM. M982 His-TbpB was eluted in fractions at about 250 mM imidazole. Fractions were pooled and dialyzed against PBS for 48 hrs and dialyzed against Tris 20 mM, NaCl 300 mM, pH 8.0. The dialysate is diluted 5-fold with a solution of Tris 20 mM, NaCl 300 mM and imidazole 20 mM. The diluted dialysate was then submitted to second purification step identical to the previous one. Fractions eluted at 250 mM imidazole are recovered, pooled and extensively dialysed against PBS. The dialysate was diluted with PBS 10% glycerol to a protein concentration of about 1 mg/ml.

B16B6 His-TbpB (also Called SP544)

The sequence encoding the mature TbpB protein from strain B16B6 was produced from the tbpB sequence available from the database Entrez Gene du NCBI (National Center for the Biotechnology Information) at http://www.ncbi.nlm.nih.gov under the accession number Z15129 corresponding to the B16B6 tbp locus. The sequence encoding the mature protein [without the peptide signal sequence and the first amino acid (Cys); starting with Leu in position 2] was placed in a pET28b plasmid (Novagen), in frame and immediately downstream a His-tag encoding sequence, under the control of the T7 promoter to give plasmid pSP544 (which also contains a kanamycin resistant gene and a plasmid stability element).

BL21 (DE3) *E. coli* strain transformed with plasmid pSP544 is cultured at 37° C. during 20 hrs in Auto Induction Medium (Formedium™) supplemented with kanamycin 30 μg/ml.

Cells are harvested by centrifugation at 5 000 g, 15 min, 4° C. Pellets corresponding to 6 L of cultures are resuspended in 240 mL of lysis buffer Tris 50 mM pH7.5, NaCl 300 mM, β-mercaptoethanol 5 mM, MgCl2 2 mM, leupeptine 1 mM, pepstatine 1 mM, CHAPS 0.1%, urea 0.5 M. The suspensions are incubated 1 hr at room temperature under shaking. Cells are disrupted by 4 cycles at Pin 1100 bars and Pout 110 bars. Benzonase is added at 1 mM and incubation is pursued 1 hour at 4° C. under shaking. Soluble and insoluble proteins are separated by centrifugation at 46,000 g, 30 min at 4° C.

Purification is performed onto affinity resin Ni-Sepharose 6 Fast Flow 6 ml (Amersham GE Healthcare) in column XK16 (Amersham GE Healthcare). Soluble fraction from lysis is loaded on Ni-Sepharose equilibrated in Buffer A (Tris 50 mM, pH 7.5, NaCl 300 mM, CHAPS 0.1%, urea 0.5 M, β-mercaptoethanol 1 mM). Steps of 30 column volumes (CV) were performed at 2% of buffer B (Tris 50 mM pH 7.5, NaCl 300 mM, CHAPS 0.1%, urea 0.5 M, β-mercaptoethanol 1 mM, imidazole 1 M, followed by a linear gradient up to 100% of buffer B (30 CV).

Fractions eluted from the column are analysed by SDS-PAGE and those containing SP544 (MW≈64.3 kDa) are pooled and submitted to size-exclusion chromatography.

Ni-Sepharose pool is loaded on an S-200 preparative gel filtration column and eluted in Tris-HCl 50 mM, pH 7.5, NaCl 150 mM, β-mercaptoethanol 1 mM. Fractions eluted from the column are analysed by SDS-PAGE and those containing SP544 (MW≈64.3 kDa) are pooled and dialyzed against Tris-HCl 50 mM, pH 7.5, NaCl 10 mM, 1-mercaptoethanol 1 mM. The dialysate is then submitted to ion-exchange chromatography.

The dialysate is loaded on 4 mL of an anion exchange (ANX) resin previously equilibrated in buffer Tris-HCl 50 mM pH 7.5, NaCl 10 mM, β-mercaptoethanol 1 mM. Elution with 30 column volumes is performed at 0 to 50% of buffer B (Tris-HCl 50 mM pH 7.5, NaCl 1 M, β-mercaptoethanol 1 mM).

Fractions eluted from the column are analysed by SDS-PAGE and those containing SP544 (MW=64.3 kDa) are pooled and dialysed against Tris-HCl 50 mM, pH 7.5, NaCl 10 mM, β-mercaptoethanol 1 mM, glycerol 10% (v/v). The dialysate is concentrated 4-fold on Amicon 3 kDa MWCO (Molecular Weight Cut Off) device to give an SP544 solution at 0.52 mg/mL that is stored at −80° C.

Recombinant Expression of MC58 NalP SP509 Construct

The expression strain is the *E. coli* BL21 (DE3) strain containing the pSP509 plasmid. This plasmid derives from vector pET28 (Novagen). The sequence encoding a truncated and mutated NalP from strain MC58 (NalP TR mut; also called SP509) is placed under the control of the T7 promoter (from pET28). This plasmid contains also a kanamycin resistant gene and a plasmid stability element.

The sequence encoding the NalP TR mut (SP509) was produced from the nalP gene (NMB1969) of the *N. meningitidis* MC58 genome available from the Entrez Gene database of the NCBI (National Center for the Biotechnology Information) at http://www.ncbi.nlm.nih.gov under the accession number NC_003112. The NalP TR mut (SP509) starts with Glycine 30 and ends with Glycine 853 (amino acid numbering is based on the complete amino acid sequence of NMB1969) and with insertion of the Ser 426 Ala mutation generated by overlap PCR extension. A His-tag is added at the N-ter end, without spacer. The amino acid sequence of SP509 without the his-tag is shown in SEQ ID NO: 7.

*E. coli* BL21 (DE3) strain (Novagen) was transformed with pSP509 according to the supplier recommendations.

BL21 (DE3) *E. coli* strain transformed by plasmid pSP509 is seeded at a ratio 1:500 in Luria Bertani broth (LB) medium supplemented with kanamycin 30 pg/ml and cultured at 37° C. under stirring (220 rpm) up to a O.D.600 nm of from 0.6 to 0.8. The IPTG is added at 1 mM final and induction is pursued 3 hrs at 37° C. Bacterial cells are harvested by centrifugation and pellets stored at −20° C.

Recombinant Expression of MC58 IgA1 Protease SP503, SP548 and SP550 Constructs

The sequences encoding IgA1P SP503, SP548 and SP550 were produced from the iga gene (NMB0700) and the app gene (NMB1985) of the *N. meningitidis* MC58 genome available from the Entrez Gene data-base of the NCBI (National Center for the Biotechnology Information) at http://www.ncbi.nlm.nih.gjov under the accession number NC_003112.

The sequences and the expression plasmids containing them (respectively pSP503, pSP548 and pSP550) were conceived and designed by bioinformatics using the software pack Vector NTI (Invitrogen).

Each of pSP503, pSP548 and pSP550 derives from vector pET28 (Novagen). The respective encoding sequence is placed under the control of the T7 promoter (from pET28). This vector also contains a kanamycin resistant gene and a plasmid stability element.

SP503 starts with Alanine 28 and ends with Alanine 1584 (amino acid numbering is based on the complete IgA1P amino acid sequence NMB0700) and comprises the Ser 267 Val mutation. A His-tag is added at the N-ter end, separated from Ala 28 by a spacer constituted with four glycines and one serine (N-ter to C-ter). The amino acid sequence of SP503 without the his-tag is shown in SEQ ID NO: 8.

SP548 starts with Alanine 28 and ends with Alanine 1005 (amino acid numbering is based on the complete IgA1P amino acid sequence NMB0700) and comprises the Ser 267 Val mutation. A His-tag is added at the C-ter end, without spacer. The amino acid sequence of SP548 without the his-tag is shown in SEQ ID NO: 9

SP550 consists from N-ter to C-ter in (i) the IgA1P sequence exhibiting the Ser 267 Val mutation, starting with Alanine 28, ending with Glutamic acid 966 (amino acid numbering is based on the complete IgA1P amino acid sequence NMB0700) fused to (ii) the App sequence starting with Glutamine 1061 and ending with Alanine 1187 (amino acid numbering is based on the complete App amino acid sequence NMB 1985). A His-tag is added at the C-ter end, without spacer. The amino acid sequence of SP550 without the his-tag is shown in SEQ ID NO: 10

*E. coli* BL21 (DE3) strain (Novagen) was transformed with each of pSP503, pSP548 and pSP550 according to the supplier recommendations.

Transformed BL21 (DE3) *E. coli* strains are seeded at a ratio 1:500 in LB medium supplemented with kanamycin 30 pg/ml and cultured about at 37° C. under stirring (220 rpm) up to a O.D.600 nm of from 0.6 to 0.8. The IPTG is added at 1 mM final and induction is pursued 3 hrs at 37° C. Bacterial cells are harvested by centrifugation and pellets stored at −20° C.

Preparation of MC58 NalP SP509 and IgA1P, SP503, SP548 and SP550 Extracts for Purification on an IMAC Column.

The bacterial pellets corresponding to 500 ml of culture are gently washed in PBS and bacterial suspensions are centrifuged. Pellets are resuspended in PBS (SP509, SP503, SP550) or Tris HCl 50 mM (SP548); each buffer being complemented with lysosyme 100 µl/ml, MgCl2 1 mM, Triton X100 0.1%. Incubation is achieved at 4° C. 15 min under mild stirring.

Benzonase is added at about 1 unit/ml. Suspension are further incubated at 4° C. 15-30 min. For SP509 and SP548, the suspensions are then gently sonicated 1 min in ice and stirred 20 min at 4° C.

Suspensions are centrifuged 20 min at 30 000 g, 4° C. Pellets are resuspended in PBS (SP509, SP503, SP550) or Tris HCl 50 mM (SP548); each buffer being complemented with Triton X100 0.1% and urea 2 M. The suspensions are incubated for 1 hr at 4° C. under mild stirring and centrifuged 20 min at 30 000 g 4° C.

The SP509 pellets are resuspended in Tris-HCl 20 mM, NaCl 300 mM, Guanidine 6 M and DTT (dithiothreitol) 5 mM, pH 8.0. The suspensions are incubated for 1 hr and centrifuged 20 min at 30 000 g 4° C. Supernatants are recovered.

The SP503, SP548 and SP550 pellets are resuspended in Tris-HCl 50 mM, NaCl 300 mM, Urea 8 M, pH 9.0. The suspensions are incubated at 4° C. overnight under mild stirring and then centrifuged 20-30 min at 30 000 g 4° C. Supernatants are recovered.

Purification of MC58 NalP SP509

The supernatant is recovered and applied onto an IMAC column (HPLC Biorad Biologic) previously (i) washed with 6 column volumes of water and (ii) equilibrated with 3 column volumes of Buffer A (Tris-HCl 20 mM, NaCl 300 mM, Guanidine 6 M, DTT 1 mM, pH 8.0). 6 column volumes of Buffer A are added. Purification program once the supernatant is applied on the column, is as follows: 6 CV 100% buffer A; 3 CV gradient 100% buffer A→92%+0% buffer B (buffer A+250 mM imidazole)→8%; 6 CV 92% buffer A+8% buffer B; 6 CV gradient 92% buffer A→0%+ 8% buffer B→100%; 3 CV 100% buffer B.

Fractions containing SP509 eluted at about 20 mM imidazole are pooled and dialysed overnight against PBS urea 4 M to remove guanidine. SP509 solution is kept at −80° C.

Before use, SP509 in PBS urea 4 M is extemporaneously dialysed against PBS arginine 0.5 M for renaturation.

Purification of MC58 IgA1P SP503, SP548 and SP550

The supernatant is diluted vol./vol. to a final concentration of Tris 50 mM, NaCl 300 mM Urea 4 M, Zwittergent 3.14 1%, pH 9.0.

An IMAC column is prepared with 50 ml of a chelating gel charged with nickel. The column is equilibrated with buffer A (Tris-HCl 50 mM, NaCl 300 mM, Urea 4 M, pH 9.0) at a flow rate of 2 ml/min. This flow rate is applied to the following purification steps.

About 100-150 ml of the SP503, 548 or 550 solution to be purified are applied onto the equilibrated column.

About 3 column volumes of Buffer A are added. Then 3 column volumes of a gradient is applied to: 100 to 80% buffer A +20% buffer B (Buffer A +250 mM Imidazole). This is followed by (i) 3 column volumes of 80% buffer A +20% buffer B; and then (ii) 4 column volumes of buffer B.

The SP503 fractions eluted at 50 mM imidazole are pooled and dialysed overnight against PBS urea 4 M and stored at −80° C. After dialysis against 4 M urea, about 19 mg of SP503 are recovered (about 0.3 mg/ml). Before use, SP503 is renatured by extensive dialysis against Tris-HCl 20 mM, NaCl 150 mM, Arginine 0.5 M, pH 8.0. The final SP503 concentration is about 0.40 mg/ml.

The SP548 and SP550 fractions each elute at 250 mM imidazole. Fractions are pooled and dialysed overnight against Tris HCl 20 mM, NaCl 150 mM, urea 4 M, pH 8.0.

After dialysis against 4 M urea, about 50 mg of SP548 are recovered (about 3.40 mg/ml). The concentration is decreased to about 0.4 mg/mL. SP548 is renatured by extensive dialysis against Tris-HCl 20 mM, NaCl 150 mM, Arginine 0.5 M, pH 8.0 and stored at −80° C. (0.50 mg/ml).

After dialysis against 4 M urea, about 50 mg of SP550 are recovered (about 3.15 mg/ml). The concentration is decreased to about 0.7 mg/ml. SP550 is renatured by extensive dialysis against Tris-HCl 20 mM, NaCl 150 mM, Arginine 0.5 M, pH 8 and stored at −80° C. (0.75 mg/ml).

AF04 Adjuvant

AF04 is constituted with (i) an oil-in-water emulsion as described in WO 07/006939 and (ii) the Eisai product ER 804057 (also known as E6020, described in U.S. Pat. No. 7,683,200) which is a TLR4-agonist. AF04 in PBS is more particularly described in Examples 1 and 2 of WO 07/080308.

Liposomes

Liposomes LPS L8

LPS L8 and liposomes LPS L8 are produced as described in WO 10/130896. The final liposome LPS L8 preparation for use in the third experiment (see below) contains 108 µg/ml LPS L8, 4.7 mg/ml EDOPC and 2.20 mg/ml DOPE in Tris 10 mM, NaCl 150 mM, merthiolate 0.001%, pH 7.2.

Empty Liposomes (Liposomes without LPS L8)

Empty liposomes are prepared as liposomes LPS L8 with the proviso that the volume of LPS L8 at 1 mg/ml in Tris 10 mM, octyl β-D-glucopyranoside (OG) 100 mM (added to the EDOPC:DOPE suspension) is replaced by an identical volume of Tris 10 mM, OG 100 mM. The final empty liposome preparation for use in the third experiment (see below) contains 4.7 mg/ml EDOPC and 2.51 mg/ml DOPE in Tris 10 mM, NaCl 150 mM, merthiolate 0.001%, pH 7.2.

Immunogenicity. Bactericidal Activity & Flow Cytometry Analysis

Bacterial Strains and Growth Conditions

A set of 36 wild-type serogroup B *N. meningitidis* strains isolated from geographically distinct locations at different dates of isolation and representing diverse MLST clonal complexes were selected for this study. They are listed in Table 5. The majority of the strains were kindly provided by Drs D. A Caugant (NIPH, Norway), D. Martin (EZR, New-Zealand), M. K Taha (IP, Paris), M. A. Diggle (SHLM-PRL, Scotland), L. Saarinen (NPHI, Finland).

MenB strains were grown overnight at 37° C. with 10% $CO_2$ on Brain Heart Infusion (BHI) agar (Difco) plates. Then, the bacteria were harvested from plates and inoculated into BHI broth (Difco) alone or supplemented with or without 30 µM desferal which is a chelator of divalent cations. Cultures were analysed after 2.5 hrs that correspond to an early exponential growth phase.

TABLE 5

| Clonal complex | Strain | Origin | | |
|---|---|---|---|---|
| | | Year | Country | Source |
| ST32 | MC58 | 1983 | UK | C |
| | BZ83 | 1984 | NL | C |
| | 8680 | 1987 | Chile | C |
| | LNP22763 | — | FR | T |
| | LNP20443 | 2003 | FR | T |
| | NG144/82 | 1982 | NO | C |
| | H44/76 | | | |
| | NGPB24 | 1984 | NO | C |

TABLE 5-continued

| Clonal complex | Strain | Origin Year | Country | Source |
|---|---|---|---|---|
| ST11 | B16B6 | — | | |
| | NGP20 | | | |
| | M986 | 1967 | | Coll.S.Pasteur |
| | FAM18 (Men C) | | | |
| ST18 | EG327 | 1985 | DE | C |
| | 1000 | 1988 | Russia | C |
| Others | S3032 | 1973 | USA | S |
| | BZ232 | 1964 | NL | C |
| | M982 | — | USA | S |
| | NGH41 | | | |
| | Z2491 (Men A) | | | |
| ST41/44 | RH873 | — | USA | S |
| | 95/46 | 1995 | NZ | M |
| | LNP22979 | | FR | T |
| | LNP23015 | 2005 | FR | T |
| | 90/94 | 2005 | UK | C |
| | 92/123 | 1992 | NZ | M |
| | BZ138 | 1982 | NL | C |
| | M101/93 | 1993 | Iceland | C |

TABLE 5-continued

| Clonal complex | Strain | Origin Year | Country | Source |
|---|---|---|---|---|
| ST8 | BZ163 | | | |
| | BZ157 | 1973 | NL | C |
| | M2 | | Marocco | C |
| ST269 | 60 (07-1734) | 2007 | Scotland | D |
| | 62 (07-1889) | | | |
| | 28 (05-2606) | 2005 | Scotland | D |
| | 30 (05-2751) | 2005 | Scotland | D |
| | 22 (05-1524) | 2005 | UK | D |
| | NGF26 | 1988 | NO | C |

C: Dr D. A. Caugeant, NIPH, Norway; D: Dr M. A. Diggle, SHLMPRL, Scotland; M: Dr D. Martin, ESR New-Zealand; S: Dr L. Saarinen, NPHI, Finland; T: Dr M. K. Taha, I P, Paris: S Pasteur: Sanofi Pasteur.

The following Table 6 describes more precisely the strains listed, in particular with regard to the IgA1P, TbpB and NalP expression.

TABLE 6

IgA1P, TbpB and NalP expression in the strains used in heterologous SBA assay

| ST complex | Strains | IgA1P Gene type | % | TbpB Isotype | % | NalP Phase variation | % | Immunotype |
|---|---|---|---|---|---|---|---|---|
| 32 | MC58 | 1 | 100% | II | 82% | ON | 100% | L3 |
| | BZ83 | 1 | 100% | II | 69% | ON | 99% | L3 |
| | 8680 | nd | nd | II | 63% | ON | nd | L8 |
| | LNP22763 | nd | nd | II | 73% | OFF | | L3 |
| | LNP20443 | | | II | 76% | ON | | L3 |
| | NG144/82 | | | II | | ON | | L3 |
| | H44/76 | 1 | 79% | II | 66% | ON | nd | L3 |
| | NGPB24 | nd | nd | II | 67% | ON | nd | L3 |
| 11 | B16B6 | 1 | 79% | I | 33% | ON | 96% | L2 |
| | NGP20 | 1 | nd | I | 33% | ON | nd | |
| | M986 | 1 | 79% | I | 33% | ON | nd | L4-like |
| | FAM18 (MenC) | 1 | 79% | | | | | nd |
| Others | S3032 | 1 | 96% | II | 78% | OFF | | L3 |
| | BZ232 | 2 | nd | II | 85% | ON | nd | L2 |
| | M982 | 1 | 79% | II | 100% | OFF | | L3 |
| | NGH41 | 2 | 72% | II | 79% | ON | nd | |
| | Z2491 (MenA) | 1 | 95% | II | 70% | ON | 99% | |
| 18 | EG327 | | | II | | Absent | | nd |
| | 1000 | 2 | 72% | II | 68% | Absent | | nd |
| 41/44 | RH873 | 2 | nd | II | 77% | OFF | | L8 |
| | 95/46 | nd | nd | II | 83% | OFF | | L3 |
| | LNP22979 | nd | nd | II | 75% | ON | 96% | L3 |
| | LNP23015 | | | II | 75% | ON | | L3 |
| | 90/94 | | | II | 76% | ON | | nd |
| | 92/123 | nd | nd | II | 68% | ON | nd | L1 |
| | BZ138 | | | II | 81% | ON | | L3 |
| | M101/93 | | | II | 76% | ON | | L1 |
| 8 | BZ163 | nd | nd | II | 82% | OFF | | |
| | BZ157 | 1 | 79% | II | 78% | ON | 96% | L2 |
| | M2 | 2 | nd | II | 71% | ON | nd | L4 |
| 269 | 60 (07-1734) | nd | nd | II | 76% | OFF | | L1 |
| | 62 (07-1889) | 1 | 94% | II | 80% | Absent | | |
| | 28 (05-2606) | 2 | 94% | I | 37% | OFF | | L1 |
| | 30 (05-2751) | | | II | | 80% OFF | | nd |
| | 22 (05-1524) | | | II | | OFF | | nd |
| | NGF26 | | | II | 75% | present | | L3 |

%: Gene identity percentage by comparison with either the MC58 gene (igaP, nalP) or the M982 tbpB.
nd: non-determined Production of Mouse or Rabbit Antisera To obtain specific immune sera, outbred CD1 mice or rabbits were immunized 3 times on days 0, 21 and 35 (mouse) or 42 (rabbit), by subcutaneous (mouse) or intramuscular (rabbit) route, with 10 pg/mouse or rabbit of the antigen of interest under a volume of 0.2 ml, in the presence of various adjuvants.

When more than one antigen were concomitantly administered, the two or three antigens were respectively administered as bivalent or trivalent preparation.

Blood samples were collected on day 42 (mouse) or 56 (rabbit). Blood samples were collected in Vacutainer vials containing a coagulation activator and a serum separator gel (BD, Meylan France). Tubes were centrifuged for 20 min at 2600 g in order to separate serum from cells. Sera were transferred into Nunc tubes and de-complemented by heat-inactivation for 30 min at 56° C. They were stored at −20° C. until the assays were performed.

IgG Purification from Rabbit Antisera

IgGs were purified on an Hi Trap rProtein A FF column (GE Healthcare) using the AKTAdesign™ system chromatography, according to the supplier recommendations.

Serum Bactericidal Activity Assay $N.$ meningitidis strains were grown overnight at 37° C. with 10% $CO_2$ on BHI agar (Difco) plates. The bacteria were then harvested from the plates and inoculated into BHI broth (Difco) alone or supplemented with 30 pM desferal which is a chelator of divalent cations so that TbpB be expressed. The cultures were analyzed after 2.5 hours, which corresponds to early exponential growth phase. The bactericidal activity of specific mouse sera was evaluated using as complement source pooled baby rabbit serum as described earlier with slight modifications (Rokbi et al., Clin. Diagnostic Lab. Immunol. (September 1997) 4 (5): 522). Briefly, 50 µl of two-fold serial dilutions of IgG solutions or serum were added to 96-well microtiter plates (Nunc) and incubated with 25 µl of a meningococci suspension adjusted to $4 \times 10^3$ CFU/ml and 25 µl of baby rabbit complement. After 1 hr of incubation at 37° C., 50 µl of the mixture from each well was plated onto MHA plates. The plates were incubated overnight at 37° C. in 10% $CO_2$. The bactericidal titer of each serum or IgG preparation was expressed as the inverse of the last dilution of serum at which ≥50% killing was observed compared to the complement control.

The SBA assay is commonly acknowledged as a surrogate of protection for $N.$ meningitidis vaccines. When the SBA titer is superior or equal to 16 in homologous SBA assay, or superior or equal to 8 in heterologous SBA, protection is considered to be met.

Flow Cytometry Analysis

The ability of polyclonal antisera elicited by the recombinant proteins to bind to the surface of live MenB strains was determined using a flow cytometric detection of indirect fluorescence assay. A culture sample was centrifuged and washed once with 1×PBS (Eurobio). The final pellet was resuspended in PBS with 1% of bovine serum albumin (BSA, Eurobio) at a density of $10^8$ CFU/ml. To 20 µl of bacteria, 20 µl of dilutions of pooled serum were added in 96 deep-well plate (Ritter). For each pool of serum, several dilutions were tested on a range going from 1/5 to over 1/2000. The plate was incubated for 1h at 37° C. with shaking. The bacteria were centrifuged, washed once with PBS 1% BSA and resuspended with 100 µl of goat anti-mouse IgG (H and L chains) conjugated to fluorescein isothiocyanate (FITC) (Southern Biotech) diluted 100-fold. The plate was incubated for 30 minutes at 37° C. with shaking in the dark. The bacteria were washed twice with PBS 1% BSA and fixed with 0.3% formaldehyde in PBS buffer overnight at +4° C. in the dark. The bacteria were centrifuged, the formaldehyde solution was discarded and the bacteria were finally washed once and dissolved in PBS 1% BSA. The fluorescent staining of bacteria was analysed on a Cytomics FC500 flow cytometer (Beckman Coulter). The fluorescent signal obtained for bacteria incubated with the polyclonal antisera or purified IgGs thereof specific for proteins injected with adjuvant was compared to the signal obtained for bacteria incubated with the antisera of mice injected with buffer+adjuvant.

B—Results

Mouse antisera raised against one or several antigens were individually assayed for serum bactericidal activity (SBA) against the homologous strain or as a pool against a panel of heterologous strains. In addition, pools of sera were assessed for their ability to recognize the targeted protein at the surface of live bacterial cells using flow cytometry (FACS analysis).

In a first experiment, three monovalent preparations comprising each the M982 His-TbpB, the MC58 NalP SP509 and the MC58 IgA1P SP503 administered as a single product were compared to:

(A) three bivalent preparations comprising:
  (i) M982 His-TbpB and MC58 NalP SP509;
  (ii) MC58 NalP SP509 and MC58 IgA1P SP503;
  (iii) M982 His-TbpB and MC58 IgA1P SP503: and
(B) a trivalent preparation comprising M982 His-TbpB, MC58 NalP SP509 and MC58 IgAIP SP503.

All of these proteins were produced as described above. Monovalent, bivalent and trivalent compositions (10 pg per protein in 200 µl per injection) were prepared in PBS pH 7.0, 2.5% squalene, 4 µg TLA4E (AF04).

Two negative controls were added: PBS with or without the adjuvant AF04 (2.5% squalene, 4 µg TLA4E).

SBA Against Strain MC58

Groups of 10-15 mice were immunized as described above with one of the monovalent, bivalent or trivalent compositions. Sera were collected as described above and individually assayed in the SBA test against strain MC58 grown 2.5 hrs in the presence of Desferal. Results were as shown in the following table 7, expressed in terms of (i) geometric mean titers (GMTs); (ii) percentage of responders exhibiting an antiserum with an SBA titer superior or equal to 16; and (iii) fold increase of the geometrical mean titers compared to the corresponding buffer.

TABLE 7

| | SBA MC58 BHI 2h30 + Desferal | |
|---|---|---|
| | GMT & % of responders ≥ 16 | Fold increase of GMT compared to the corresponding buffer |
| MC58 NalP SP509 | 168.9 (93%) | 16.9 |
| MC58 IgA1P SP503 | 348.4 (100%) | 30.8 |
| M982 His-TbpB + MC58 NalP SP509 | 90.5 (95%) | 8.0 |
| MC58 NalP SP509 + MC58 IgA1P SP503 | 461.4 (100%) | 40.8 |
| M982 His-TbpB + MC58 IgA1P SP503 | 430.5 (100%) | 38.0 |
| M982 His-TbpB + MC58 NalP SP509 + MC58 IgA1P SP503 | 776.0 (100%) | 68.7 |
| Control AF04 | 11.3 (60%) | |
| Control PBS | 11.3 | |

The monovalent M982 His-TbpB induced a strong SBA activity against the homologous strain (not shown in Table 7). The monovalent NalP SP509 and IgA1P SP503 both induced high SBA titers against the homologous strain MC58.

SBA titers against MC58 (GMTs) induced by bivalent compositions were similar to those obtained with the respective monovalent compositions, indicating that no negative interference occurred when the antigens were mixed. Additionally, the percentage of outbred CD1 murine responders was >90%; which is considered as a very positive result.

The highest GMT was obtained with the trivalent composition.

Heterologous SBA and Flow Cytometry Analysis

The pools of sera raised to the constructs were assessed for bactericidal activity against a panel of 26 strains including the homologous strains MC58 and M982, and representative of the major epidemiological clusters (ST32, ST11, ST41/44, ST8 and ST269). SBA results were expressed in term of fold-increase (FI) of the geometric mean titers compared to the negative control including the AF04 adjuvant. It is considered that cross-bactericidal activity is met when the fold-increase is superior or equal to 8. Surface Exposure (SE) is expressed in terms of detection level ranging from [—] to [++++] depending on the highest dilution of the pooled antisera at which surface exposure is detected: [—] at a dilution <1/20e; [+] at a 1/20e dilution: [++] at a 1/200e dilution; [+++] at a 1/2000e dilution; and [++++] at a dilution >1/2000e.

Results are shown in FIGS. 1-7 (in which ST, SBA and SE respectively mean clonal complex, serum bactericidal activity and surface exposure) and partially summarized in Table 8 below:

TABLE 8

| | Coverage: percentage of strains killed (fold increase superior or equal to 8) over 26 |
|---|---|
| M982 His-TbpB | 27% |
| MC58 NalP SP509 | 46% |
| MC58 IgA1P SP503 | 73% |
| M982 TbpB + MC58 NalP SP509 | 62% |
| MC58 NalP SP509 + MC58 IgA1P SP503 | 92% |
| M982 His-TbpB + MC58 IgA1P SP503 | 73% |
| M982 His-TbpB + MC58 NalP SP509 + MC58 IgA1P SP503 | 85% |

The compositions of the invention give satisfactory immune responses. A coverage superior or equal to 85% is considered as being very satisfactory.

In a second experiment, three monovalent preparations comprising each a different MC58 IgA1P construct (SP503, SP548 or SP550) administered as a single product were compared with trivalent preparations comprising (i) MC58 IgA1P SP503 or SP548, or MC58 IgA1P-App fusion construct SP550; (ii) MC58 NalP SP509; and (iii) M982 TbpB.

Two negative controls were added: PBS with or without the adjuvant AF04 (2.5% squalene, 4 µg TLA4E).

M982 TbpB was recombinantly expressed from E. coli BL21 (DE3) transformed with pSP314, purified from the small scale lot and formulated in PBS as described above. Monovalent composition for injection is prepared at 10 µg/dose (200 µl) in PBS, 2.5% squalene, 4 pg TLA4E (AF04).

SP509, SP503, SP548 and SP550 were produced as described above. Monovalent SP509, SP503, SP548 and SP550 compositions as well as trivalent compositions (10 pg per protein in 200 µl per injection) were prepared in Tris 20 mM, NaCl 150 mM, Arginine 0.5 M, pH 8.0, 2.5% squalene, 4 pg TLA4E (AF04).

Homologous SBA

Groups of 10-15 mice were immunized as described above with one of the monovalent or trivalent compositions. Sera were collected as described above and individually assayed in the SBA assay against the homologous strain MC58 or strain M982 (strain MC58 is M982-like) grown 2.5 hrs in the presence of Desferal. Results were as shown in the following table 9, expressed in terms of (i) geometrical means titers (GMTs); (ii) percentage of responders exhibiting an antiserum with an SBA titer superior or equal to 16; and (iii) fold increase of the geometrical mean titers compared to the corresponding buffer.

TABLE 9

| | SBA MC58 BHI 2h30 + Desferal | | SBA M982 BHI 2h30 + Desferal | |
|---|---|---|---|---|
| | GMT & % of responders ≥ 16 | Fold increase of GMT compared to the corresponding buffer | GMT & % of responders ≥ 16 | Fold increase of GMT compared to the corresponding buffer |
| MC58 IgA1P SP503 | 362 (100%) | X 157 | 80.6 (100%) | X 27 |
| MC58 IgA1P SP548 | 256 (100%) | X 111 | 59.7 (100%) | X 20 |
| MC58 IgA1P-App fusion construct SP550 | 256 (100%) | X 111 | 111.4 (100%) | X 37 |
| MC58 IgA1P SP503 + MC58 NalP SP509 + M982 TbpB | 276.5 (100%) | X 120 | 789.6 (100%) | X 263 |
| MC58 IgA1P SP548 + MC58 NalP SP509 + M982 TbpB | 238.9 (100%) | X 104 | 1024.0 (100%) | X 341 |
| MC58 IgA1P-App fusion construct SP550 + MC58 NalP SP509 + M982 TbpB | 168.9 (100%) | X 65 | 724.1 (100%) | X 241 |
| Control AF04 | 2.3 (0%) | | 3.0 | |
| Control PBS | 2.5 (0%) | | 4.0 | |

Results shown in Table 9 reveal that:

Monovalent MC58 IgA1P SP503 or SP548 and MC58 IgA1P-App fusion construct SP550 compositions induce similar SBA titers (GMTs) against the MC58 strain as well as trivalent compositions containing each of them; and SBA titers against the M982 strain induced by any of the trivalent compositions are significantly superior to those induced by the monovalent composition (about 10-fold).

Heterologous SBA and Flow cytometry (FACS) Analysis

The pools of sera raised to the constructs were assayed for bactericidal activity against a panel of 20 strains including the homologous strains MC58 and M982. SBA results were expressed in term of fold-increase of the geometrical mean titers compared to the negative control including the AF04 adjuvant. It is considered that cross-bactericidal activity is met when the fold-increase is superior or equal to 8. The ability of the pools of sera to bind to the bacterial surface was also examined. Surface Exposure (SE) is expressed in terms of detection level ranging from [—] to [++++] depending on the highest dilution of the specific pooled antisera at which surface exposure is detected: [—] at a dilution <1/20e; [+] at a 1/20e dilution: [++] at a 1/200e dilution; [+++] at a 1/2000e dilution; and [++++] at a dilution >1/2000e.

Results are shown in FIGS. 8-13 (in which ST, SBA and SE respectively mean clonal complex, serum bactericidal activity and surface exposure) and partially summarized in Table 10 below:

TABLE 10

| | Coverage: number of strains killed (fold increase superior or equal to 8) over 20 | Percentage of strains detected by FACS* over 20 |
|---|---|---|
| MC58 IgA1P SP503 | 18/20 (90%) | 80% |
| MC58 IgA1P SP548 | 15/20 (75%) | 70% |
| MC58 IgA1P-App fusion construct SP550 | 16/20 (80%) | 85% |
| MC58 IgA1P SP503 + MC58 NalP SP509 + M982 TbpB | 20/20 (100%) | 100% |
| MC58 IgA1P SP548 + MC58 NalP SP509 + M982 TbpB | 20/20 (100%) | 100% |
| MC58 IgA1P-App fusion construct SP550 + MC58 NalP SP509 + M982 TbpB | 19/20 (95%) | 100% |

*using an antiserum against the injected protein, or the combination of injected proteins, as appropriate.

In a third experiment, three quadrivalent compositions were assayed for cross-SBA. They were as follows:

Composition/group A:
M982 TbpB+MC58 NalP SP509+MC58 IgA1P-App fusion construct SP550+B16B6 TbpB lipidated+liposomes LPS L8 [negative control: liposomes without LPS (empty liposomes)]

Composition/group B:
M982 TbpB+MC58 NalP SP509+MC58 IgA1P-App fusion construct SP550+B16B6 His-TbpB+AF04 [negative control: AF04 in PBS]

Composition/group C:
M982 TbpB+MC58 NalP SP509+MC58 IgA1P-App fusion construct SP550+B16B6 His-TbpB+empty liposomes [negative control: liposomes without LPS (empty liposomes)].

The primary objective of the experiment was to evaluate the adjuvant effect of L8 LPS formulated in liposomes, co-injected with the lipidated B16B6 TbpB produced as described above, on the antibody responses raised against M982 TbpB, MC58 NalP SP509 and MC58 IgA1P-App fusion construct SP550. This adjuvant effect of LPS liposomes was also compared to the adjuvant effect of the adjuvant formulation AF04.

The second objective was to compare the vaccine coverage measured by cross-SBA generated by compositions A, B and C.

M982 TbpB was recombinantly expressed from *E. coli* BL21 (DE3) transformed with pSP314, purified from the pilot scale lot and formulated in Tris 50 mM, NaCl 100 mM, sucrose 5%, pH 7.5, as described above. MC58 IgA1P-App fusion construct SP550, MC58 NalP SP509, B16B6 TbpB and B16B6 His-TbpB were produced as described above.

Compositions contained 10 pg of each protein and (i) 40 pg of liposomes under a volume of 500 µl or AF04 (2.5% squalene, 10 µg TLA4E/dose). The dilution buffer for liposomes was Tris 10 mM, NaCl 150 mM, merthiolate 0.001%, pH 7.2.

Rabbits were immunized intramuscularly (2 sites; 2×250 µl) at DO, D21 and D42. Sera are collected at D56 and IgGs purified as described above. Purified IgGs are used in the SBA test described above against a panel of 30 strains. SBA results were expressed in term of fold-increase (FI) of the geometric mean titers compared to that the appropriate negative control. It is considered that cross-bactericidal activity is met when the fold-increase is superior or equal to 8. The ability of the IgGs purified from the pooled antisera to bind to the bacterial surface was also examined. Surface Exposure (SE) is expressed in terms of detection level ranging from [—] to [++++] depending on the highest dilution of the specific purified IgGs at which surface exposure is detected: [—] at a dilution <1/20e; [+] at a 1/20e dilution: [++] at a 1/200e dilution; [+++] at a 1/2000e dilution; and [++++] at a dilution >1/2000e.

Figure 14:
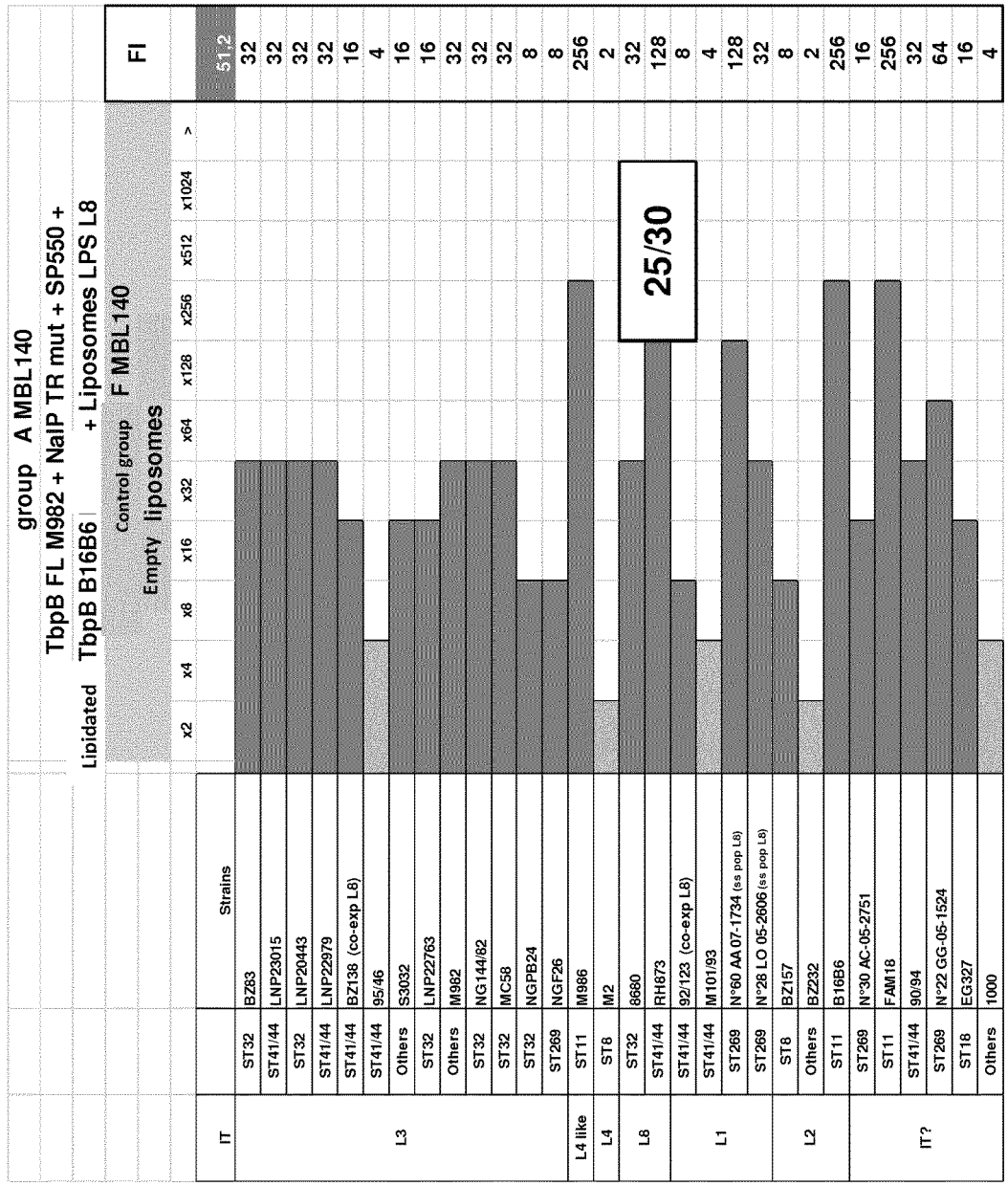
FIG. 14 is a graph showing cross-SBA results generated with a quadrivalent composition comprising M982 TbpB+MC58 NalP SP509+MC58 IgA1P-App fusion construct SP550+B16B6 TbpB lipidated+liposomes LPS L8. SBA results are expressed in term of fold-increase (FI).
Figure 15:
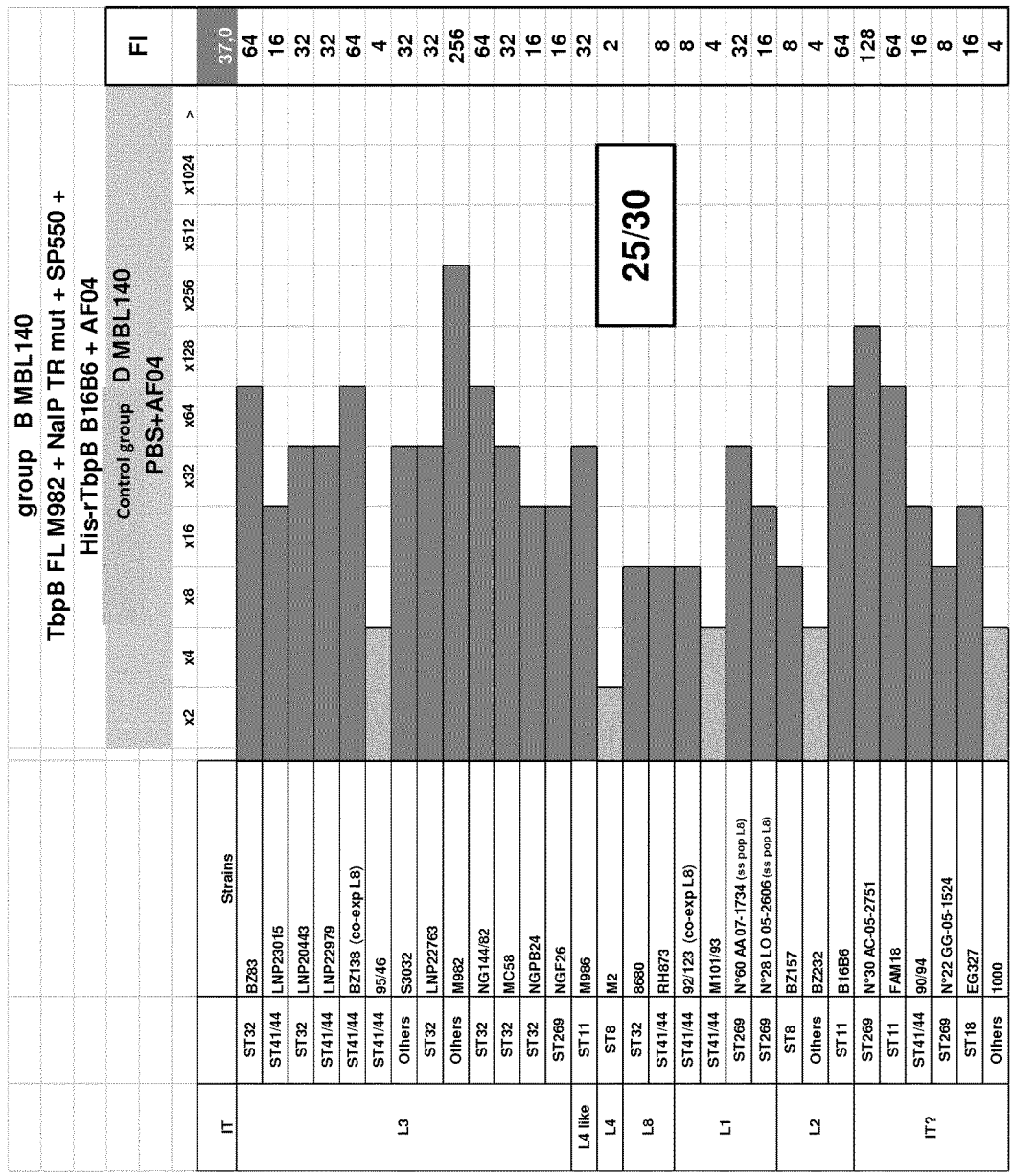
FIG. 15 is a graph showing cross-SBA results generated with a quadrivalent composition comprising M982 TbpB+MC58 NalP SP509+MC58 IgA1P-App fusion construct SP550+B16B6 His-TbpB+AF04. SBA results are expressed in term of fold-increase (FI).
Figure 16:
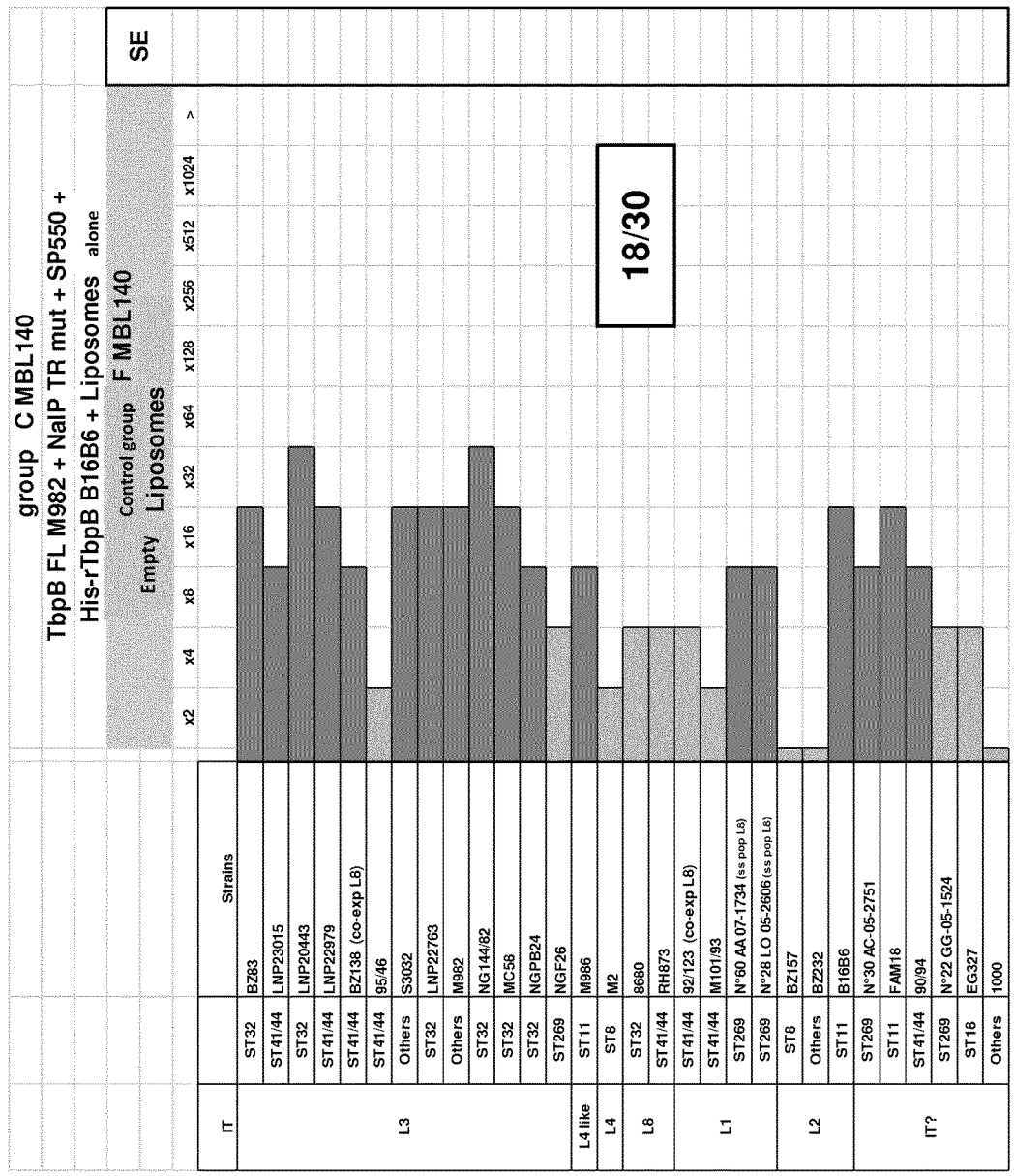
FIG. 16 is a graph showing cross-SBA results generated with a quadrivalent composition comprising M982 TbpB+MC58 NalP SP509+MC58 IgA1P-App fusion construct SP550+B16B6 His-TbpB+empty liposomes. SBA results are expressed in term of fold-increase

Results are shown in FIGS. 14-16 in which IT, ST, SBA and FI respectively mean immunotype, clonal complex, and serum bactericidal activity and (SBA) fold-increase of the geometric mean titers compared to the negative control. In summary, an identical coverage is observed with multivalent compositions comprising either liposomes LPS L8 or AF04 (25/30 strains). Empty liposomes are not as effective as liposomes LPS L8. LPS L8 added in the liposomal formulation in the presence of a lipidated TbpB is as efficient as AF04.

REFERENCES

Giuliani et al., PNAS (2006) 103 (29): 10834
Smith et al., J. Mol. Biol. (1981) 147: 195
Altschul et al., (1990) J. Mol. Biol., 215: 403
Lomholt et al., Mol. Microb. (1995) 15 (3): 495
Vitovski & Sayers, Infect. Immun. (2007) 75 (6): 2875
Ulsen & Tommassen, FEMS Microbiol. Rev. (2006) 30 (2): 292
WO 90/11367
Tettelin et al., Science (March 2000) 287: 1809
Gripstra et al., Res. in Microbiol. (2013) 164: 562
Pohlner et al., Nature (1987) 325: 458
van Ulsen et al., FEMS Immunol Med. Microb. (2001) 32: 53
Serruto et al., Mol. Microb. (2003) 48 (2): 323
van Ulsen et al., Microbes & Infection (2006) 8: 2088
Turner et al., Infect. Immun. (2006) 74 (5): 2957
Henderson et al., Microbiol. Mol. Biol. Rev. (2004) 68 (4): 692
Vitovski et al., (1999) FASEB J. 13: 331
WO 00/26375
Turner et al., Infect. Immun. (2002) 70: 4447
van Ulsen et al., Mol. Microbiol. (2003) 50 (3): 1017
WO 00/66791
Parkhill et al., Nature (March 2000) 404: 502
Bentley et al., PLoS Genet., 3, e23 (2007)
Roussel-Jazédé et al., Infect Immun. (2010) 78 (7): 3083
Serruto et al., PNAS February 2010 107 (8): 3770
Harrison et al., BMC Microbiol. 2008, 8: 66
Renauld-Mongenie et al., J. Bacteriol. (2004) 186 (3): 850
Legrain et al., Gene (1993) 130 (1): 73
EP 586 266
WO 10/130896
WO 10/130898
Rokbi et al., Infect. Immun. (2000) 68 (9): 4938
Giuliani et al., PNAS, (July 2006) 103 (29): 10834
Giuliani et al., Infect. Immun. (February 2005) 73 (2): 1151
Fletcher et al., Infect. Immun. (2004) 72: 2088
Masignani et al., J. Exp. Med. (March 2003) 197 (6): 789
Achtman et al., J. Infect. Dis. (1992) 165: 53
U.S. Pat. No. 5,705,161
WO 04/014417

WO 01/022994
U.S. Pat. No. 6,531,131
U.S. Pat. No. 6,482,807
U.S. Pat. No. 6,887,483
WO 06/108586
U.S. Pat. No. 5,888,519
U.S. Pat. No. 5,698,721
U.S. Pat. No. 5,902,802
U.S. Pat. No. 5,651,981
WO 10/130896
Westphal & Jann, (1965) Meth. Carbohydr. Chem. 5: 83
Gu & Tsai, 1993, Infect. Immun. 61 (5): 1873

Wu et al., 1987, Anal. Biochem. 160: 281
WO 94/00153
U.S. Pat. No. 6,113,918
U.S. Pat. No. 6,303,347
WO 98/50399
US 2003/0153532
WO2007/005583
WO 07/006939
U.S. Pat. No. 7,683,200
WO 07/080308
Rokbi et al., Clin. Diagnostic Lab. (1997) 4 (5): 522

---

The invention claimed is:

1. A composition comprising at least two *Neisseria meningitidis* antigens selected from a group consisting of a trypsin-like serine protease auto-transporter antigen, an NalP antigen, and a TbpB antigen,
wherein said trypsin-like serine protease auto-transporter antigen is in the form of a polypeptide selected from the polypeptides consisting of
(I) a mutant of a full-length mature *N. meningitidis* trypsin-like serine protease auto-transporter that lacks or has reduced trypsin-like serine protease activity and/or does not contain any cleavage site able/susceptible to be cleaved by a trypsin-like serine protease;
(II) (a) a fragment of a full-length mature trypsin-like serine protease auto-transporter of *N. meningitidis*, said fragment consisting of
(i) a protease domain of a trypsin-like serine protease auto-transporter of *N. meningitidis*;
(ii) a protease domain and all or part of an α-peptide domain of a trypsin-like serine protease auto-transporter of *N. meningitidis*; or
(iii) a protease domain, an α-peptide domain and a part of a β-domain comprising at least one and no more than eleven β-sheets of a trypsin-like serine protease auto-transporter of *N. meningitidis*; or
(b) a mutant of said fragment (II)(a) that lacks or has reduced trypsin-like serine protease activity and/or does not contain any cleavage site able/susceptible to be cleaved by a trypsin-like serine protease; and (III) a fusion polypeptide comprising a first fragment fused to a second fragment, wherein said first fragment consists of a protease domain or a protease sub-domain of a first full-length mature trypsin-like serine protease auto-transporter of *N. meningitidis*, or a mutant of a protease domain or a protease sub-domain of a first trypsin-like serine protease auto-transporter of *N. meningitidis* which lacks or has reduced trypsin-like serine protease activity and/or does not contain any cleavage site able/susceptible to be cleaved by a trypsin-like serine protease, and said second fragment consists of an $\alpha$-peptide domain, and optionally a part of a $\beta$-domain, of a second full-length mature trypsin-like serine protease auto-transporter of *N. meningitidis;* wherein the first and second trypsin-like serine protease auto-transporters are different;

wherein the C-terminus of the first fragment is fused to the N-terminus of the second fragment; and wherein said polypeptide does not comprise the said full-length mature trypsin-like serine protease auto-transporter of *N. meningitidis,* wherein said NalP antigen is in the form of a polypeptide comprising (I) a fragment of a full-length mature *N. meningitidis* NalP protein which full-length mature *N. meningitidis* NalP protein comprises (a) a passenger domain comprising a subtilisin-like serine protease triad and (b) a beta-domain comprising a translocator domain, an alpha-peptide and a beta-core composed of twelve beta-sheets; said NalP fragment comprising (i) at the N-terminus, the NalP passenger domain;

(ii) at the C-terminus, the beta-domain comprising the translocator domain, the alpha-peptide and at least one and no more than eleven beta-sheets;

wherein said polypeptide does not comprise a full-length mature *N. meningitidis* NalP protein; or (II) a mutant of said NalP fragment (I) which lacks or has reduced subtilisin-like serine protease activity and/or does not contain any cleavage site able to be cleaved by a subtilisin-like serine protease;

and wherein said TbpB antigen is devoid of a signal peptide sequence and of the cysteine residue following this signal peptide sequence in the full-length TbpB of *N. meningitidis.*

2. A composition according to claim 1, which comprises (i) the trypsin-like serine protease auto-transporter antigen and (ii) the NalP antigen and/or TbpB antigen.

3. A composition according to claim 1, wherein the TbpB antigen is of isotype II.

4. A composition according to claim 3, which further comprises the TbpB antigen of isotype I.

5. A composition according to claim 1, which further comprises an additional *N. meningitidis* protein antigen.

6. A composition according to claim 2, which is a bivalent composition comprising the trypsin-like serine protease auto-transporter antigen and the NalP antigen.

7. A composition according to claim 2, which is a bivalent composition comprising the trypsin-like serine protease auto-transporter antigen and the TbpB antigen.

8. A composition according to claim 2, which is a trivalent composition comprising (i) the trypsin-like serine protease auto-transporter antigen, (ii) the NalP antigen and (iii) the TbpB antigen.

9. A composition according to claim 4, which is a trivalent composition comprising (i) the trypsin-like serine protease auto-transporter antigen, (ii) the TbpB antigen of isotype II and (iii) the TbpB antigen of isotype I.

10. A composition according to claim 4, which is a quadrivalent composition comprising (i) the IgA1P antigen, (ii) the NalP antigen, (iii) the TbpB antigen of isotype II and (iv) the TbpB antigen of isotype I.

11. A composition according to claim 3, wherein the TbpB antigen of isotype II is the TbpB of strain M982.

12. A composition according to claim 4, wherein the TbpB antigen of isotype I is the TbpB of strain B16B6.

13. A composition according to claim 4, wherein the TbpB antigen of isotype I is lipidated.

14. A composition according to claim 1, wherein the NalP antigen is of strain MC58.

15. A composition according to claim 14, wherein the NalP antigen comprises the amino acid sequence SEQ ID NO: 7.

16. A composition according to claim 1, wherein the trypsin-like serine protease auto-transporter antigen is the IgA1P antigen.

17. A composition according to claim 16, wherein the IgA1P antigen is of strain MC58.

18. A composition according to claim 17, wherein the IgA1P antigen comprises an amino acid sequence selected from SEQ ID NO: 8 and SEQ ID NO: 9.

19. A composition according to claim 1, wherein the trypsin-like serine protease auto-transporter antigen is a fusion polypeptide comprising or consisting of:

a first fragment fused to a second fragment:

(1) said first fragment consisting of:

a protease domain or a protease sub-domain of a first full-length mature trypsin-like serine protease auto-transporter of *N. meningitidis*, or a mutant of a protease domain or a protease sub-domain of a first trypsin-like serine protease auto-transporter of *N. meningitidis* which lacks or has reduced trypsin-like serine protease activity and/or does not contain any cleavage site able/susceptible to be cleaved by a trypsin-like serine protease, (2) said second fragment consisting of:

an $\alpha$-peptide domain, and optionally a part of a $\beta$-domain, of a second full-length mature trypsin-like serine protease auto-transporter of *N. meningitidis;* wherein the first and second trypsin-like serine protease auto-transporters are different;

wherein the C-terminus of the first fragment is fused to the N-terminus of the second fragment; and wherein said polypeptide does not comprise the said full-length mature trypsin-like serine protease auto-transporter of *N. meningitidis.*

20. A composition according to claim 19, wherein the trypsin-like serine protease auto-transporter antigen comprises an amino acid sequence consisting in SEQ ID NO: 10.

21. A composition according to claim 1, which further comprises a *N. meningitidis* LOS.

22. A composition according to claim 21, wherein the LOS is detoxified in liposomes.

23. A composition according to claim 9, wherein the TbpB antigen of isotype II is the TbpB of strain M982.

24. A composition according to claim 10, wherein the TbpB antigen of isotype II is the TbpB of strain M982.

25. A composition according to claim 9, wherein the TbpB antigen of isotype I is the TbpB of strain B16B6.

26. A composition according to claim 10, wherein the TbpB antigen of isotype I is the TbpB of strain B16B6.

27. A composition according to claim 9, wherein the TbpB antigen of isotype I is lipidated.

28. A composition according to claim 10 wherein the TbpB antigen of isotype I is lipidated.

29. A composition according to claim 12, wherein the TbpB antigen of isotype I is lipidated.

30. A composition according to claim 8, wherein the NalP antigen is of strain MC58.

31. A composition according to claim 10, wherein the NalP antigen is of strain MC58.

* * * * *